(12) United States Patent
Kawakami et al.

(10) Patent No.: US 9,960,369 B2
(45) Date of Patent: *May 1, 2018

(54) COMPOUND, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Atsugi-shi, Kanagawa-ken (JP)

(72) Inventors: Sachiko Kawakami, Kanagawa (JP); Hiromi Seo, Kanagawa (JP); Tatsuyoshi Takahashi, Kanagawa (JP); Satoshi Seo, Kanagawa (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 269 days.

This patent is subject to a terminal disclaimer.

(21) Appl. No.: 14/699,731

(22) Filed: Apr. 29, 2015

(65) Prior Publication Data
US 2015/0318495 A1   Nov. 5, 2015

(30) Foreign Application Priority Data
May 2, 2014 (JP) .................................. 2014-095159

(51) Int. Cl.
*H01L 51/00* (2006.01)
*H01L 27/32* (2006.01)
(Continued)

(52) U.S. Cl.
CPC ........ *H01L 51/0073* (2013.01); *C07D 405/10* (2013.01); *H01L 27/3244* (2013.01);
(Continued)

(58) Field of Classification Search
CPC .............. C07D 405/10; H01L 51/0073; H01L 51/0072
(Continued)

(56) References Cited

U.S. PATENT DOCUMENTS 6,723,445 B2   4/2004   Li et al.
7,355,340 B2   4/2008   Shitagaki et al.
(Continued)

FOREIGN PATENT DOCUMENTS

JP   2007-189001 A   7/2007
WO   WO-2003/058667   7/2003

*Primary Examiner* — Michael M Dollinger
(74) *Attorney, Agent, or Firm* — Fish & Richardson P.C.

(57) ABSTRACT

To provide a novel compound which can be used as a host material in which a light-emitting substance is dispersed. To provide a light-emitting element having a long lifetime. A compound represented by General Formula (G0). In the formula, $A^1$ represents a dibenzo[f,h]quinoxalinyl group, $A^2$ represents a benzo[b]naphtho[2,3-d]furanyl group, and Ar represents an arylene group having 6 to 25 carbon atoms. The dibenzo[f,h]quinoxalinyl group, the benzo[b]naphtho[2,3-d]furanyl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

$$A^1\text{-Ar-}A^2 \quad (G0)$$

18 Claims, 16 Drawing Sheets

(51) Int. Cl.
*H04R 1/02* (2006.01)
*H04R 1/08* (2006.01)
*C07D 405/10* (2006.01)
*H01L 51/50* (2006.01)
*H01L 51/52* (2006.01)

(52) U.S. Cl.
CPC ...... *H01L 51/0052* (2013.01); *H01L 51/0072* (2013.01); *H01L 51/5072* (2013.01); *H04R 1/028* (2013.01); *H04R 1/083* (2013.01); *H01L 51/0058* (2013.01); *H01L 51/5016* (2013.01); *H01L 51/5028* (2013.01); *H01L 51/5237* (2013.01)

(58) Field of Classification Search
USPC ........................................................ 428/690
See application file for complete search history.

(56) References Cited

U.S. PATENT DOCUMENTS

| | | | |
|---|---|---|---|
| 7,601,435 B2 | 10/2009 | Shitagaki et al. | |
| 7,927,720 B2 | 4/2011 | Nomura et al. | |
| 7,931,974 B2 | 4/2011 | Egawa et al. | |
| 8,119,259 B2 | 2/2012 | Kadoma et al. | |
| 8,178,216 B2 | 5/2012 | Nomura et al. | |
| 8,231,984 B2 | 7/2012 | Shitagaki et al. | |
| 8,252,433 B2 | 8/2012 | Egawa et al. | |
| 8,314,101 B2 | 11/2012 | Kadoma et al. | |
| 2007/0247063 A1* | 10/2007 | Murase | C07D 209/86 313/504 |
| 2009/0026922 A1 | 1/2009 | Iwaki et al. | |
| 2009/0153041 A1 | 6/2009 | Kawakami et al. | |
| 2009/0184633 A1 | 7/2009 | Kadoma et al. | |
| 2011/0210316 A1 | 9/2011 | Kadoma et al. | |
| 2012/0138914 A1 | 6/2012 | Kawamura et al. | |
| 2012/0165556 A1 | 6/2012 | Suzuki et al. | |
| 2012/0193613 A1 | 8/2012 | Kadoma et al. | |
| 2012/0197020 A1 | 8/2012 | Osaka et al. | |
| 2012/0286257 A1 | 11/2012 | Shitagaki et al. | |
| 2012/0313506 A1 | 12/2012 | Egawa et al. | |
| 2013/0009543 A1 | 1/2013 | Kadoma et al. | |
| 2013/0048971 A1 | 2/2013 | Kitano et al. | |
| 2013/0060033 A1 | 3/2013 | Seo et al. | |
| 2013/0075704 A1 | 3/2013 | Takasu et al. | |
| 2013/0082591 A1 | 4/2013 | Seo et al. | |
| 2013/0112954 A1 | 5/2013 | Osaka et al. | |
| 2014/0124764 A1 | 5/2014 | Kitano et al. | |
| 2015/0014649 A1* | 1/2015 | Ma | H01L 51/0054 257/40 |
| 2015/0060813 A1 | 3/2015 | Kawakami et al. | |
| 2015/0194609 A1* | 7/2015 | Nishide | C07D 405/14 257/40 |
| 2016/0079546 A1* | 3/2016 | Park | H01L 51/0073 257/40 |
| 2016/0190451 A1* | 6/2016 | Ogawa | H01L 51/0072 257/40 |
| 2016/0214942 A1* | 7/2016 | Parham | C07D 401/14 |

* cited by examiner

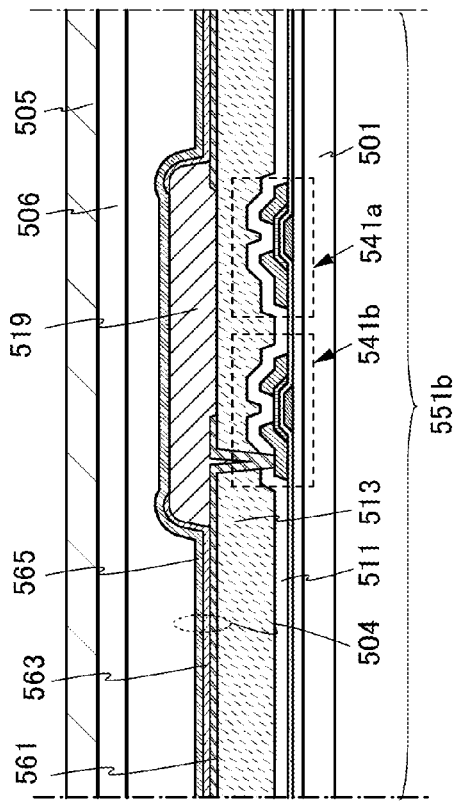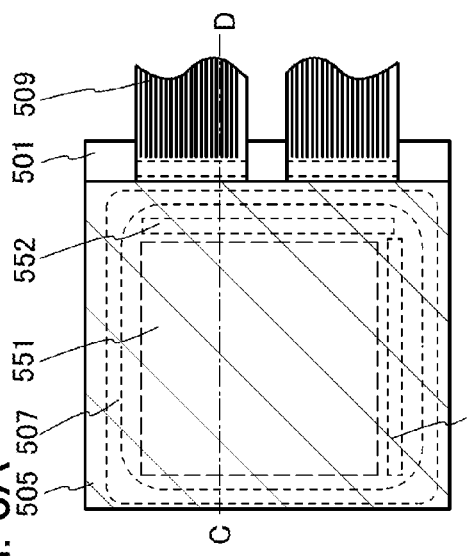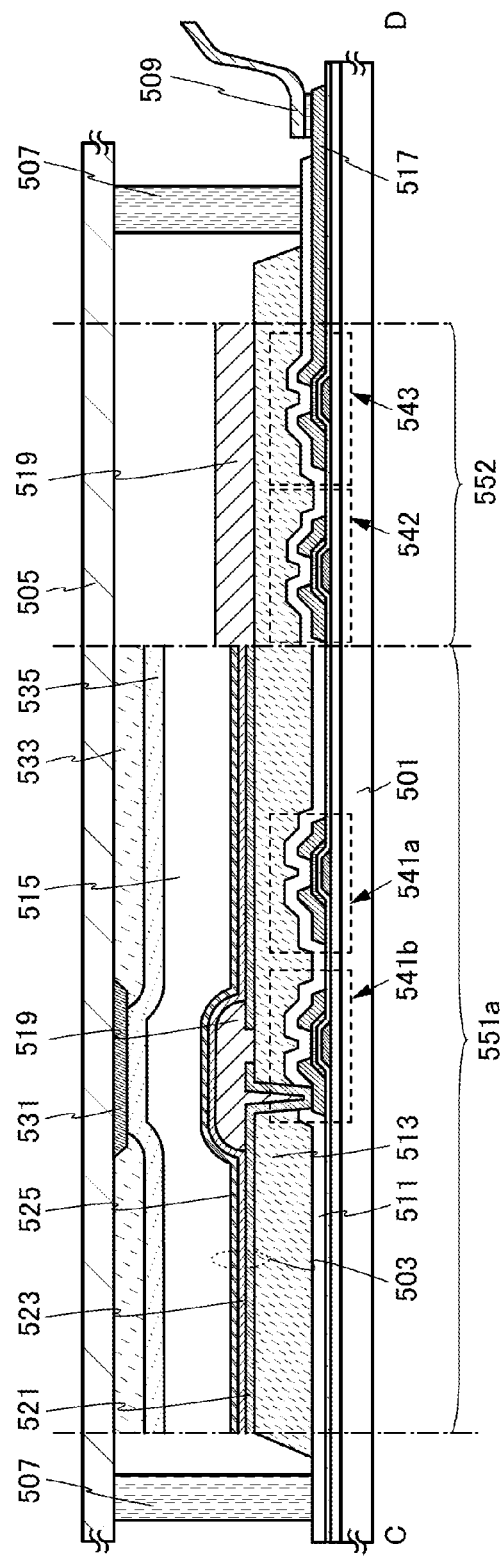

COMPOUND, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a compound, a light-emitting element utilizing electroluminescence (EL) (the light-emitting element is also referred to as an EL element), a light-emitting device, an electronic device, and a lighting device.

Note that one embodiment of the present invention is not limited to the above technical field. One embodiment of the invention disclosed in this specification and the like relates to an object, a method, and a manufacturing method. Moreover, one embodiment of the present invention relates to a process, a machine, manufacture, or a composition of matter. Specifically, examples of the technical field of one embodiment of the present invention disclosed in this specification include a semiconductor device, a display device, a light-emitting device, a power storage device, a memory device, an electronic device, a lighting device, a method for driving any of them, and a method for manufacturing any of them.

2. Description of the Related Art

In recent years, a light-emitting element using an organic compound as a light-emitting substance (the light-emitting element is also referred to as an organic EL element) has been actively researched and developed. In a basic structure of the light-emitting element, a layer containing a light-emitting substance is provided between a pair of electrodes. Voltage application to this element causes the light-emitting substance to emit light.

The light-emitting element is a self-luminous element and thus has advantages over a liquid crystal display, such as high visibility of the pixels and no need of backlight, and is considered to be suitable as a flat panel display element. Another major advantage of the light-emitting element is that it can be fabricated to be thin and lightweight. Besides, the light-emitting element has an advantage of quite high response speed.

Since the light-emitting element can be formed in a film form, planar light emission can be provided; thus, a large-area element can be easily formed. This feature is difficult to obtain with point light sources typified by incandescent lamps and LEDs or linear light sources typified by fluorescent lamps. Thus, the light-emitting element also has great potential as a planar light source applicable to a lighting device and the like.

In the case of a light-emitting element in which a layer containing an organic compound used as a light-emitting substance is provided between a pair of electrodes, by applying a voltage to the element, electrons from a cathode and holes from an anode are injected into the layer containing the organic compound and thus a current flows. The injected electrons and holes then lead the organic compound to its excited state, so that light emission is provided from the excited organic compound.

The excited state formed by an organic compound can be a singlet excited state or a triplet excited state. Light emission from the singlet excited state (S*) is called fluorescence, and light emission from the triplet excited state (T*) is called phosphorescence. The statistical generation ratio thereof in the light-emitting element is considered to be $S^*:T^*=1:3$.

At room temperature, a compound capable of converting a singlet excited state into light emission (hereinafter, referred to as a fluorescent compound) exhibits only light emission from the singlet excited state (fluorescence), and light emission from the triplet excited state (phosphorescence) cannot be observed. Accordingly, the internal quantum efficiency (the ratio of the number of generated photons to the number of injected carriers) of a light-emitting element including a fluorescent compound is assumed to have a theoretical limit of 25%, on the basis of $S^*:T^*=1:3$.

In contrast, a compound capable of converting a triplet excited state into light emission (hereinafter, referred to as a phosphorescent compound) exhibits light emission from the triplet excited state (phosphorescence). Furthermore, since intersystem crossing (i.e., transition from a singlet excited state to a triplet excited state) easily occurs in a phosphorescent compound, the internal quantum efficiency can be theoretically increased to 100%. That is, higher emission efficiency can be achieved than using a fluorescent compound. For this reason, light-emitting elements using a phosphorescent compound have been under active development recently so that high-efficiency light-emitting elements can be achieved.

When a light-emitting layer of a light-emitting element is formed using the phosphorescent compound described above, in order to inhibit concentration quenching or quenching due to triplet-triplet annihilation of the phosphorescent compound, the light-emitting layer is usually formed such that the phosphorescent compound is dispersed in a matrix of another compound. Here, the compound serving as the matrix is called host material, and the compound dispersed in the matrix, such as a phosphorescent compound, is called guest material.

When a phosphorescent compound is a guest material, a host material needs to have higher triplet excitation energy (energy difference between a ground state and a triplet excited state) than the phosphorescent compound.

Furthermore, since singlet excitation energy (energy difference between a ground state and a singlet excited state) is higher than triplet excitation energy, a substance that has high triplet excitation energy also has high singlet excitation energy. Thus, the above substance that has high triplet excitation energy is also effective in a light-emitting element using a fluorescent compound as a light-emitting substance.

Studies have been conducted on compounds having dibenzo[f,h]quinoxaline rings, which are examples of the host material used when a phosphorescent compound is a guest material (e.g., see Patent Documents 1 and 2).

REFERENCE

Patent Document

[Patent Document 1] PCT International Publication No. 03/058667
[Patent Document 2] Japanese Published Patent Application No. 2007-189001

SUMMARY OF THE INVENTION

In improving element characteristics of a light-emitting element, there are many problems which depend on a substance. Therefore, improvement in an element structure, development of a substance, and the like have been carried out in order to solve the problems. Development of light-emitting elements leaves room for improvement in terms of emission efficiency, reliability, cost, and the like.

For practical use of a display or lighting which uses a light-emitting element, a long lifetime of the light-emitting element has been required.

In view of the above, an object of one embodiment of the present invention is to provide a novel compound. An object of one embodiment of the present invention is to provide a novel compound which can be used in a light-emitting element as a host material in which a light-emitting substance is dispersed. An object of one embodiment of the present invention is to provide a novel compound that enables a light-emitting element to have high reliability. An object of one embodiment of the present invention is to provide a compound whose film quality is high. An object of one embodiment of the present invention is to provide a compound with high heat resistance.

An object of one embodiment of the present invention is to provide a light-emitting element with high emission efficiency. An object of one embodiment of the present invention is to provide a light-emitting element with a low drive voltage. An object of one embodiment of the present invention is to provide a light-emitting element having a long lifetime. An object of one embodiment of the present invention is to provide a light-emitting element with high heat resistance. An object of one embodiment of the present invention is to provide a novel light-emitting element.

An object of one embodiment of the present invention is to provide a highly reliable light-emitting device, a highly reliable electronic device, or a highly reliable lighting device using the light-emitting element. An object of one embodiment of the present invention is to provide a light-emitting device, an electronic device, or a lighting device with low power consumption using the light-emitting element.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a compound represented by General Formula (G0).

$$A^1\text{-Ar-}A^2 \tag{G0}$$

In General Formula (G0), $A^1$ represents a dibenzo[f,h]quinoxalinyl group, $A^2$ represents a benzo[b]naphtho[2,3-d]furanyl group, and Ar represents an arylene group having 6 to 25 carbon atoms. The dibenzo[f,h]quinoxalinyl group, the benzo[b]naphtho[2,3-d]furanyl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

One embodiment of the present invention is a compound represented by General Formula (G1).

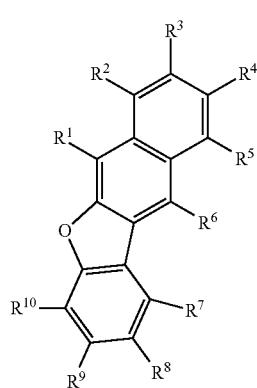

(G1)

$$A\text{—}Ar\text{——} \tag{G1-1}$$

In General Formula (G1), one of $R^7$ to $R^{10}$ represents a substituent represented by General Formula (G1-1); $R^1$ to $R^6$ and the others of $R^7$ to $R^{10}$ separately represent any one of hydrogen, an alkyl group having 1 to 6 carbon atoms, a cycloalkyl group having 3 to 6 carbon atoms, and an aryl group having 6 to 13 carbon atoms; A represents a dibenzo[f,h]quinoxalinyl group; and Ar represents an arylene group having 6 to 25 carbon atoms. The dibenzo[f,h]quinoxalinyl group, the aryl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

One embodiment of the present invention is a compound represented by General Formula (G2).

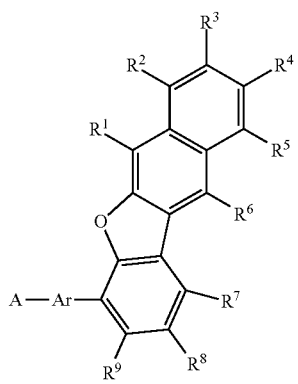

(G2)

In General Formula (G2), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms; A represents a dibenzo[f,h]quinoxalinyl group; and Ar represents an arylene group having 6 to 25 carbon atoms. The dibenzo[f,h]quinoxalinyl group, the aryl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

One embodiment of the present invention is a compound represented by General Formula (G3).

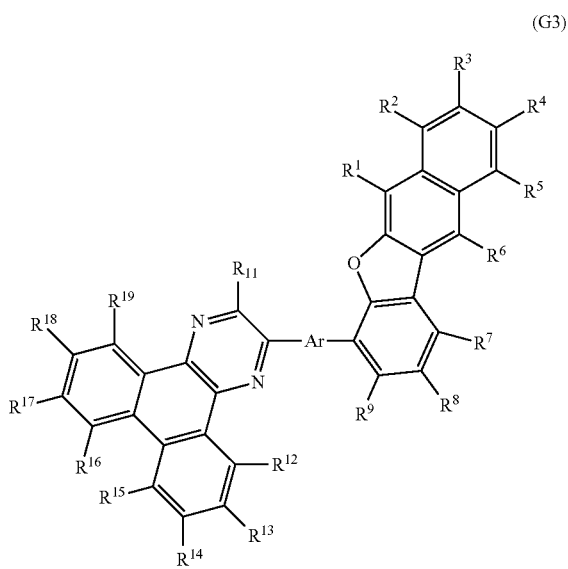

(G3)

In General Formula (G3), $R^1$ to $R^9$ and $R^{11}$ to $R^{19}$ separately represent any one of hydrogen, an alkyl group having 1 to 6 carbon atoms, a cycloalkyl group having 3 to 6 carbon atoms, and an aryl group having 6 to 13 carbon atoms, and Ar represents an arylene group having 6 to 25 carbon atoms. The aryl group and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

One embodiment of the present invention is a light-emitting element having any of the compounds with the above structures between a pair of electrodes.

One embodiment of the present invention is a light-emitting element which includes a layer containing a compound between a pair of electrodes and in which the compound has a dibenzo[f,h]quinoxaline skeleton and a benzo[b]naphtho[2,3-d]furan skeleton.

One embodiment of the present invention is a light-emitting element which includes a layer containing a compound between a pair of electrodes and in which the compound is a compound where a dibenzo[f,h]quinoxaline skeleton and a benzo[b]naphtho[2,3-d]furan skeleton are bonded through an arylene skeleton.

One embodiment of the present invention is a light-emitting device including the above-described light-emitting element in a light-emitting portion. For example, a light-emitting device of one embodiment of the present invention may include the above light-emitting element and a transistor or a substrate. One embodiment of the present invention is an electronic device including the light-emitting device in a display portion. For example, an electronic device of one embodiment of the present invention may include the above light-emitting device and a microphone, a speaker, or an external connection terminal. One embodiment of the present invention is a lighting device including the light-emitting device in a light-emitting portion. For example, a lighting device of one embodiment of the present invention may include the above light-emitting device and a support, a housing, or a cover.

Note that the light-emitting device in this specification includes, in its category, a display device using a light-emitting element. Furthermore, the light-emitting device may be included in a module in which a light-emitting element is provided with a connector such as an anisotropic conductive film or a tape carrier package (TCP), a module in which a printed wiring board is provided at the end of a TCP, and a module in which an integrated circuit (IC) is directly mounted on a light-emitting element by a chip on glass (COG) method. The light-emitting device may be included in lighting equipment or the like.

A compound represented by General Formula (G4), which is used in synthesis of the compound of one embodiment of the present invention, is also one embodiment of the present invention.

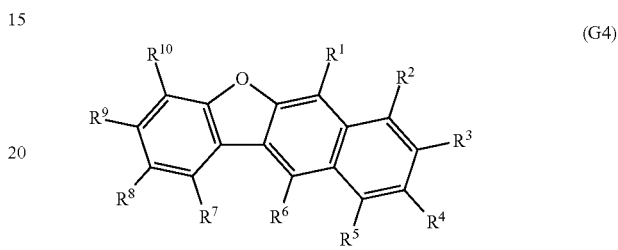

(G4)

In General Formula (G4), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms, and $R^{10}$ represents any one of chlorine, boron, iodine, a boronic acid group, and an organoboron group. The aryl group is unsubstituted or substituted by any one of an alkyl group having 1 to 6 carbon atoms, a cycloalkyl group having 3 to 6 carbon atoms, and an aryl group having 6 to 13 carbon atoms.

A compound represented by Structural Formula (201), which is used in synthesis of the compound of one embodiment of the present invention, is also one embodiment of the present invention.

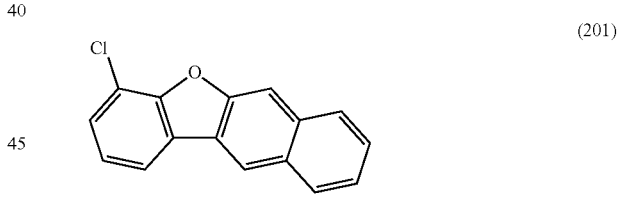

(201)

One embodiment of the present invention makes it possible to provide a novel compound. One embodiment of the present invention makes it possible to provide a novel compound which can be used in a light-emitting element as a host material in which a light-emitting substance is dispersed. One embodiment of the present invention makes it possible to provide a novel compound that enables a light-emitting element to have high reliability. One embodiment of the present invention makes it possible to provide a compound whose film quality is high. One embodiment of the present invention makes it possible to provide a compound with high heat resistance.

One embodiment of the present invention makes it possible to provide a light-emitting element with high emission efficiency. One embodiment of the present invention makes it possible to provide a light-emitting element with a low drive voltage. One embodiment of the present invention makes it possible to provide a light-emitting element having a long lifetime. One embodiment of the present invention makes it possible to provide a light-emitting element with high heat resistance. One embodiment of the present invention makes it possible to provide a novel light-emitting element.

One embodiment of the present invention makes it possible to provide a highly reliable light-emitting device, a highly reliable electronic device, or a highly reliable lighting device using the light-emitting element. One embodiment of the present invention makes it possible to provide a light-emitting device, an electronic device, or a lighting device with low power consumption using the light-emitting element.

Note that the description of these effects does not disturb the existence of other effects. One embodiment of the present invention does not necessarily achieve all the above effects. Other effects will be apparent from and can be derived from the description of the specification, the drawings, the claims, and the like.

BRIEF DESCRIPTION OF THE DRAWINGS

FIGS. 3A to 3C illustrate examples of a light-emitting device of one embodiment of the present invention.

DETAILED DESCRIPTION OF THE INVENTION

Figure 1A:
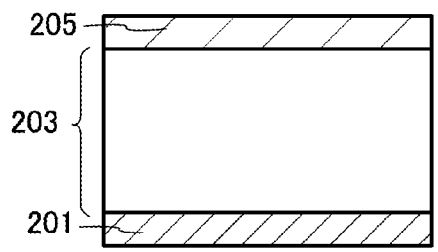
FIGS. 1A to 1D each illustrate an example of a light-emitting element of one embodiment of the present invention.

Embodiments of the present invention will be described in detail with reference to the drawings. Note that the present invention is not limited to the following description, and it is easily understood by those skilled in the art that various changes for embodiments and details can be made without departing from the spirit and scope of the invention. Therefore, the present invention should not be construed as being limited to the description in the following embodiments.

Note that in the structures of the invention described below, the same portions or portions having similar functions are denoted by the same reference numerals in different drawings, and description of such portions is not repeated. Furthermore, the same hatching pattern is applied to portions having similar functions, and the portions are not especially denoted by reference numerals in some cases.

In addition, the position, size, range, or the like of each structure illustrated in drawings and the like is not accurately represented in some cases for easy understanding. Therefore, the disclosed invention is not necessarily limited to the position, the size, the range, or the like disclosed in the drawings and the like.

Note that the terms "film" and "layer" can be interchanged with each other depending on the case or circumstances. For example, the term "conductive layer" can be changed into the term "conductive film" in some cases. In addition, the term "insulating film" can be changed into the term "insulating layer" in some cases.

(Embodiment 1)

In this embodiment, a compound of one embodiment of the present invention is described.

One embodiment of the present invention is a compound in which a dibenzo[f,h]quinoxaline skeleton and a benzo[b]naphtho[2,3-d]furan skeleton are bonded through an arylene skeleton.

A dibenzo[f,h]quinoxaline skeleton has a planar structure. A compound having a planar structure is easily crystallized. A light-emitting element using a compound that is easily crystallized has a short lifetime. However, the compound of one embodiment of the present invention has a sterically bulky structure since a benzo[b]naphtho[2,3-d]furan skeleton is bonded to a dibenzo[f,h]quinoxaline skeleton through an arylene skeleton. The compound of one embodiment of the present invention is not easily crystallized, which can inhibit a reduction in lifetime of a light-emitting element. By including a benzo[b]naphtho[2,3-d]furan skeleton, in which a benzene ring and a naphthalene ring are condensed with a furan skeleton, and a dibenzo[f,h]quinoxaline skeleton, in which two benzene rings are condensed with a quinoxaline skeleton, the compound of one embodiment of the present invention has extremely high heat resistance, and when the compound is used in a light-emitting element, the light-emitting element can have high heat resistance and a long lifetime.

When a compound that cannot easily accept electrons or holes is used as a host material in a light-emitting layer, the regions of electron-hole recombination concentrate on an interface between the light-emitting layer and a different layer, leading to a reduction in lifetime of a light-emitting element. Here, the compound of one embodiment of the present invention can easily accept electrons and holes since the compound has a dibenzo[f,h]quinoxaline skeleton as an electron-transport skeleton and a benzo[b]naphtho[2,3-d]furan skeleton as a hole-transport skeleton. Accordingly, by the use of the compound of one embodiment of the present invention as the host material of the light-emitting layer, electrons and holes presumably recombine in a wide region of the light-emitting layer and it is possible to inhibit a reduction in lifetime of the light-emitting element.

As compared to extension of a conjugated system in a compound in which a dibenzo[f,h]quinoxaline skeleton and a benzo[b]naphtho[2,3-d]furan skeleton are directly bonded, extension of a conjugated system in the compound of one embodiment of the present invention in which the two skeletons are bonded through an arylene group is small; accordingly, reductions in band gap and triplet excitation energy can be prevented. The compound of one embodiment of the present invention is also advantageous in that its heat resistance and film quality are high. Specifically, a thin film of the compound of one embodiment of the present invention suffers only a small change in shape (e.g., aggregation is not easily caused even under the air and crystallization is not easily caused even under high temperatures).

The compound of one embodiment of the present invention has a wide band gap. Accordingly, the compound can be favorably used as a host material, in which a light-emitting substance is dispersed, of a light-emitting layer in a light-emitting element. Furthermore, since the compound of one embodiment of the present invention has triplet excitation energy high enough to excite a phosphorescent compound emitting light in a wavelength range from red to green, the compound can be favorably used as a host material in which the phosphorescent compound is dispersed.

When the triplet excitation energy of a host material is too high, the adverse effects of a quenching factor increase and a light-emitting element easily deteriorates in some cases. With the use of the compound of one embodiment of the present invention, a light-emitting element that is less likely to be affected by the quenching factor and does not easily deteriorate can be provided.

Furthermore, since the compound of one embodiment of the present invention has a high electron-transport property, the compound can be suitably used as a material for an electron-transport layer in a light-emitting element.

Thus, the compound of one embodiment of the present invention can be suitably used as a material for an organic device such as a light-emitting element or an organic transistor.

One embodiment of the present invention is a compound represented by General Formula (G0).

A¹-Ar-A² (G0)

In General Formula (G0), A¹ represents a dibenzo[f,h]quinoxalinyl group, A² represents a benzo[b]naphtho[2,3-d]furanyl group, and Ar represents an arylene group having 6 to 25 carbon atoms. The dibenzo[f,h]quinoxalinyl group, the benzo[b]naphtho[2,3-d]furanyl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

One embodiment of the present invention is a compound represented by General Formula (G1). In the case where a substituent represented by General Formula (G1-1) is bonded to the benzene ring of benzo[b]naphtho[2,3-d]furan, the compound can have a higher triplet excitation energy level ($T_1$ level) than in the case where the substituent is bonded to the naphthalene ring.

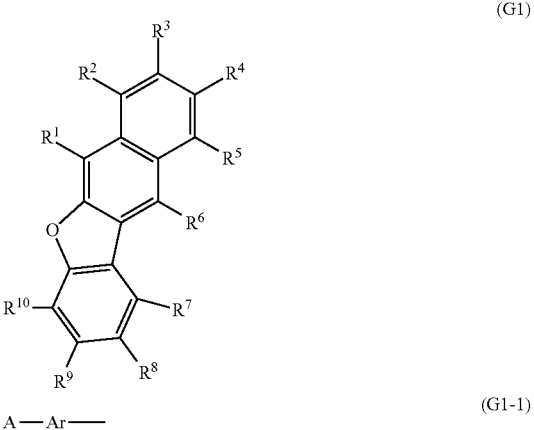

(G1)

(G1-1)

In General Formula (G1), one of $R^7$ to $R^{10}$ represents a substituent represented by General Formula (G1-1); $R^1$ to $R^6$ and the others of $R^7$ to $R^{10}$ separately represent any one of hydrogen, an alkyl group having 1 to 6 carbon atoms, a cycloalkyl group having 3 to 6 carbon atoms, and an aryl group having 6 to 13 carbon atoms; A represents a dibenzo[f,h]quinoxalinyl group; and Ar represents an arylene group having 6 to 25 carbon atoms. The dibenzo[f,h]quinoxalinyl group, the aryl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

In particular, the substituent represented by General Formula (G1-1) is preferably bonded to the 8-position of benzo[b]naphtho[2,3-d]furan skeleton in General Formula (G1) (that is, $R^{10}$ in General Formula (G1) is preferably the substituent represented by General Formula (G1-1)) because a high $T_1$ level can be achieved.

One embodiment of the present invention is a compound represented by General Formula (G2).

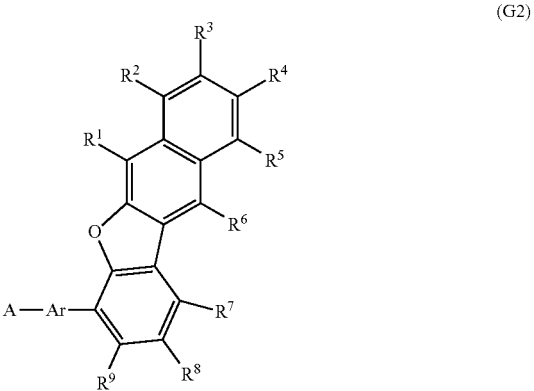

(G2)

In General Formula (G2), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms; A represents a dibenzo[f,h]quinoxalinyl group; and Ar represents an arylene group having 6 to 25 carbon atoms. The dibenzo[f,h]quinoxalinyl group, the aryl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

In the compound represented by General Formula (G2), Ar is preferably bonded to the 2-position, the 6-position, or the 7-position of the dibenzo[f,h]quinoxaline skeleton for higher purity, a higher $T_1$ level, and the like. Preferably, Ar is bonded to the 2-position because the compound can be more easily synthesized and thus can be provided at lower cost than in the case where Ar is bonded to the 6-position or the 7-position. Preferably, Ar is bonded to the 6-position because a $T_1$ level can be higher than in the case where Ar is bonded to the 2-position or the 7-position. Preferably, Ar is bonded to the 7-position because a $T_1$ level can be higher than in the case where Ar is bonded to the 2-position. Preferably, Ar is bonded to the 6-position or the 7-position because the solubility can often be higher and purification and an increase in purity can be performed more easily than in the case where Ar is bonded to the 2-position.

One embodiment of the present invention is a compound represented by General Formula (G3).

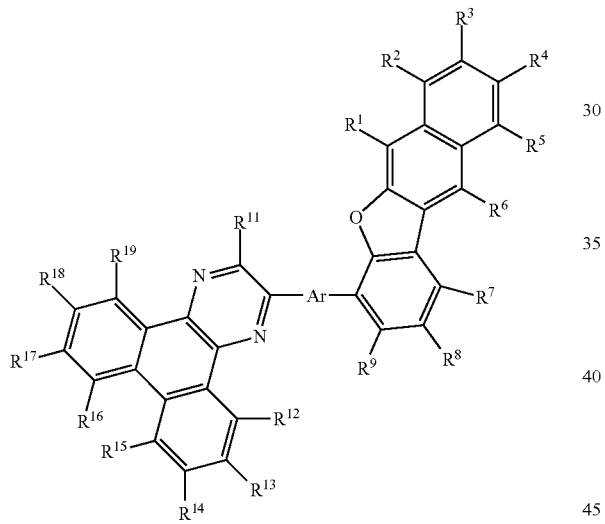

(G3)

In General Formula (G3), $R^1$ to $R^9$ and $R^{11}$ to $R^{19}$ separately represent any one of hydrogen, an alkyl group having 1 to 6 carbon atoms, a cycloalkyl group having 3 to 6 carbon atoms, and an aryl group having 6 to 13 carbon atoms, and Ar represents an arylene group having 6 to 25 carbon atoms. The aryl group and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

Specific examples of the structure of Ar in General Formulae (G1-1), (G2), and (G3) include substituents represented by Structural Formulae (1-1) to (1-18). Note that Ar may further have, as a substituent, any one of an alkyl group having 1 to 4 carbon atoms, a cycloalkyl group having 3 to 6 carbon atoms, and an aryl group having 6 to 13 carbon atoms. As examples of the aryl group having 6 to 13 carbon atoms, a phenyl group, a naphthyl group, and a fluorenyl group can be given. Specific examples of Ar having a substituent are illustrated by Structural Formulae (1-12), (1-13), (1-15), and (1-18). Note that Ar having a substituent is not limited to these examples.

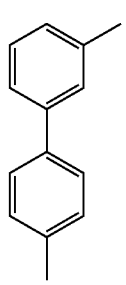

(1-9) 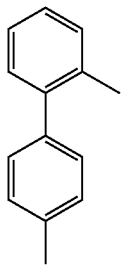

(1-10) 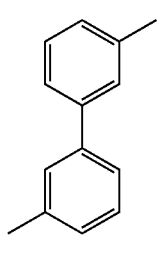

(1-11) 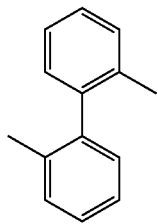

(1-12) 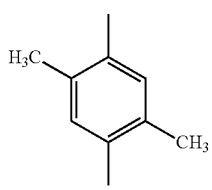

(1-13) 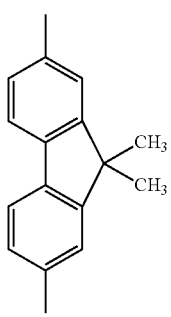

(1-14) 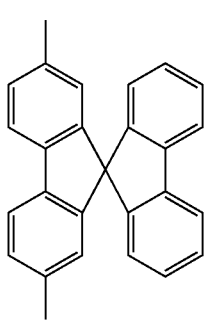

(1-15) 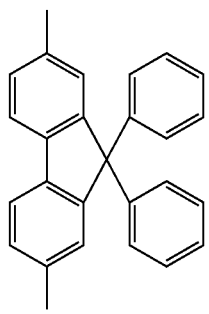

(1-16) 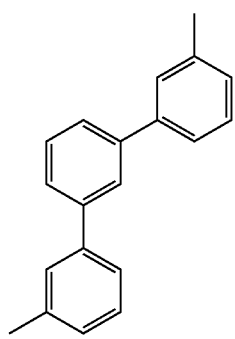

(1-17) 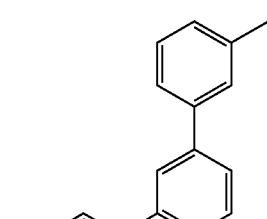

(1-18) 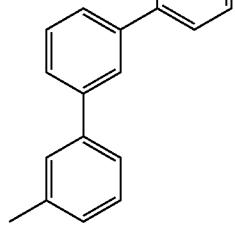

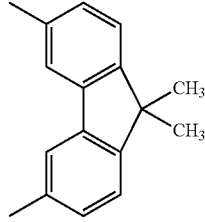

Preferably, Ar has one or more kinds of rings selected from a benzene ring, a fluorene ring, and a naphthalene ring. Preferably, Ar is a substituent including one or more kinds of rings selected from a benzene ring, a fluorene ring, and a naphthalene ring, examples of which include a phenylene group, a biphenylene group, a terphenylene group, a quaterphenylene group, a naphthalene-diyl group, and a 9H-fluoren-diyl group. In that case, the compound of one embodiment of the present invention can have high triplet excitation energy.

Specific examples of $R^1$ to $R^{19}$ in General Formulae (G1) to (G3) include substituents represented by Structural Formulae (2-1) to (2-23). Note that when $R^1$ to $R^{19}$ represent aryl groups, $R^1$ to $R^{19}$ may further have, as a substituent, any one of an alkyl group having 1 to 4 carbon atoms, a cycloalkyl group having 3 to 6 carbon atoms, and an aryl group having 6 to 13 carbon atoms. As examples of the aryl group having 6 to 13 carbon atoms, a phenyl group, a naphthyl group, and a fluorenyl group can be given. Specific examples of the aryl group having a substituent are illustrated by Structural Formulae (2-13) to (2-22). Note that $R^1$ to $R^{19}$ each having a substituent are not limited to these examples.

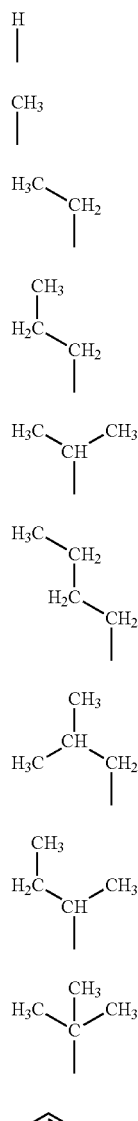

(2-1)

(2-2)

(2-3)

(2-4)

(2-5)

(2-6)

(2-7)

(2-8)

(2-9)

(2-10)

(2-11)

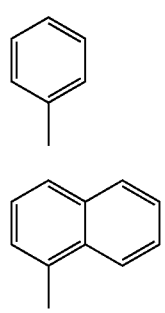

-continued

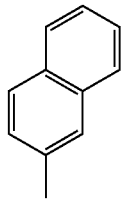
(2-12)

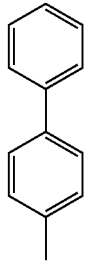
(2-13)

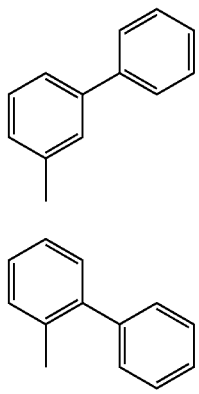
(2-14)

(2-15)

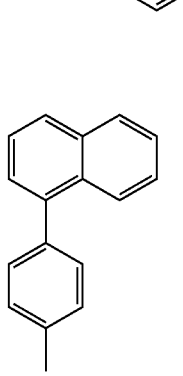
(2-16)

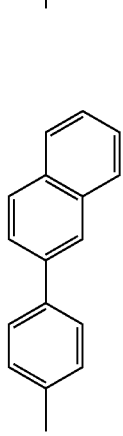
(2-17)

(2-18)
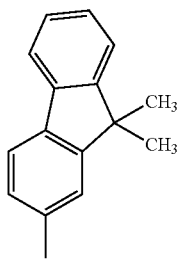
(2-19)
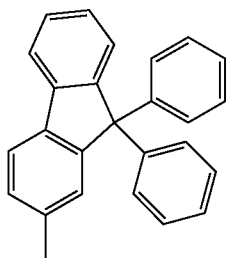
(2-20)
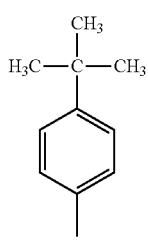
(2-21)
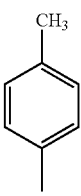
(2-22)
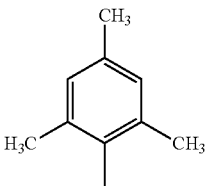
(2-23)
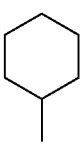
Specific examples of the compound of one embodiment of the present invention include heterocyclic compounds represented by Structural Formulae (100) to (155). However, the present invention is not limited to these structural formulae.
(100)
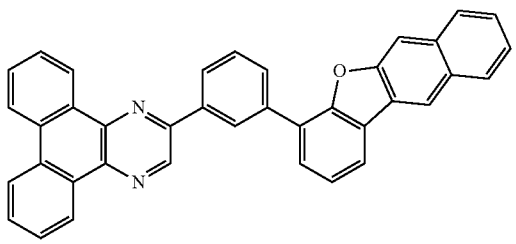
(101)
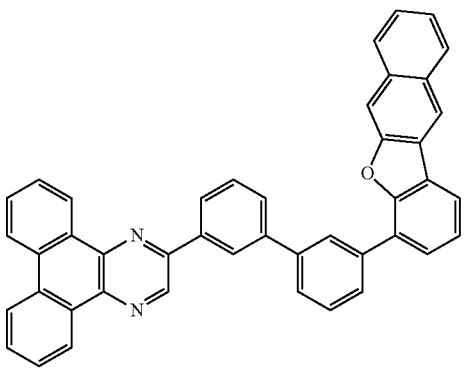
(102)
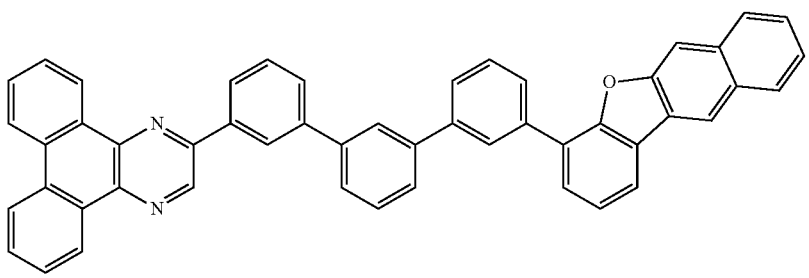

-continued
(103)
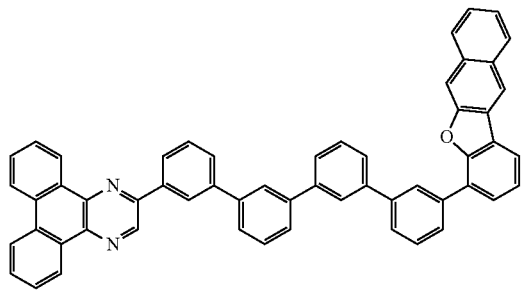
(104)
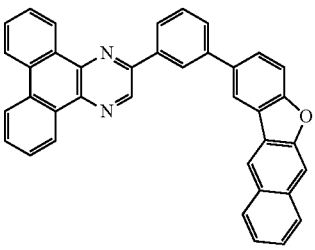
(105)
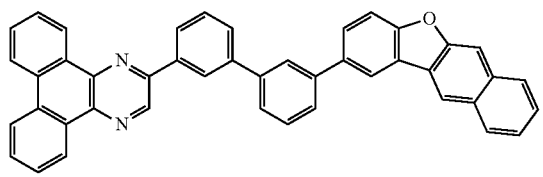
(106)
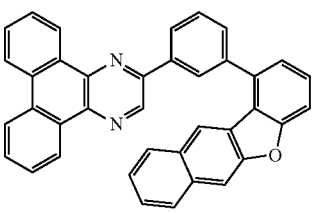
(107)
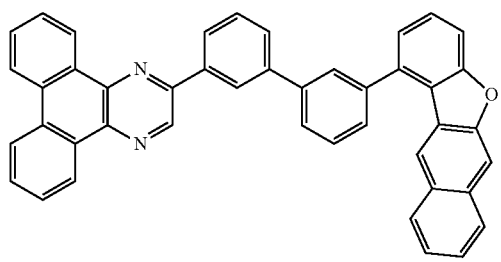
(108)
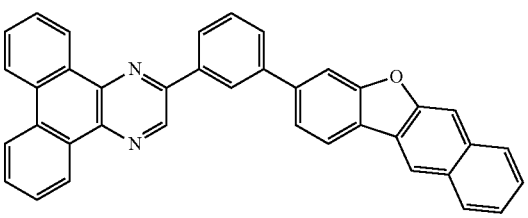
(109)
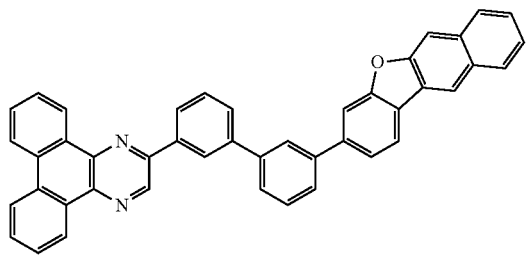
(110)
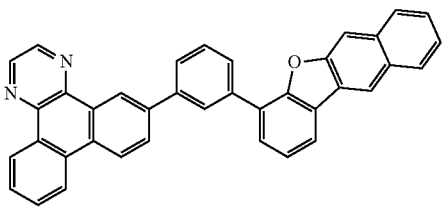
(111)
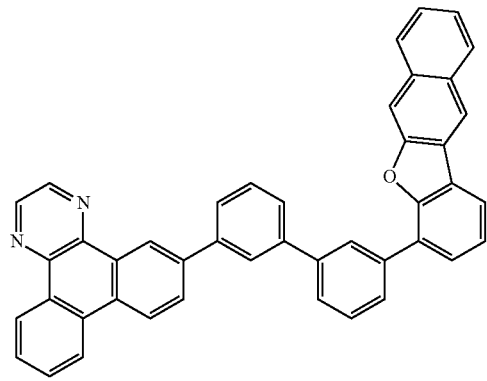
(112)
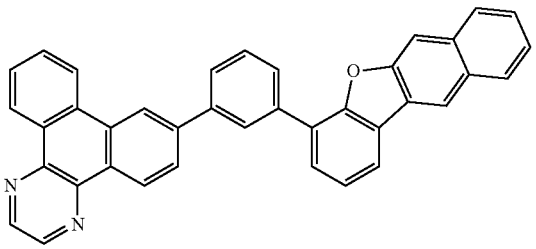

-continued
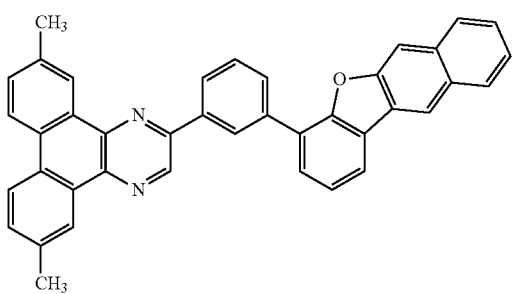
(113)
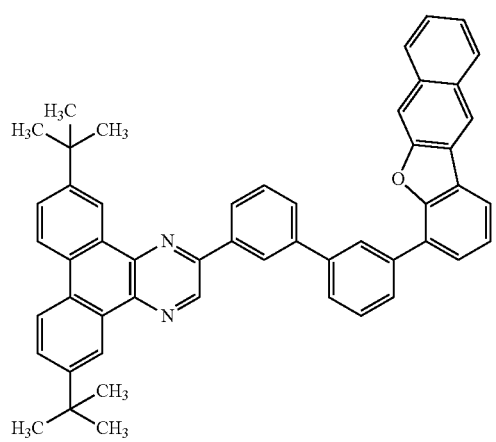
(114)
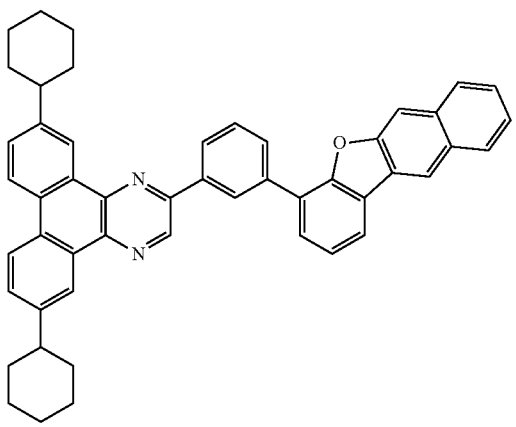
(115)
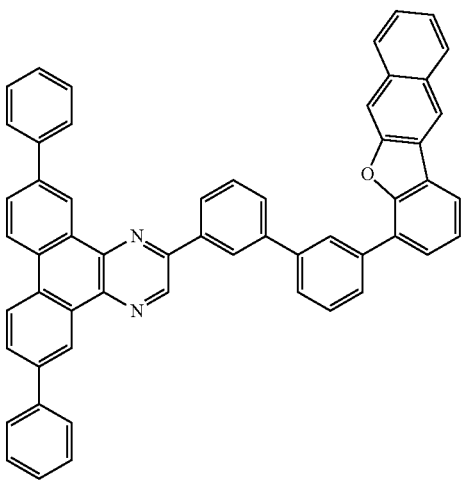
(116)
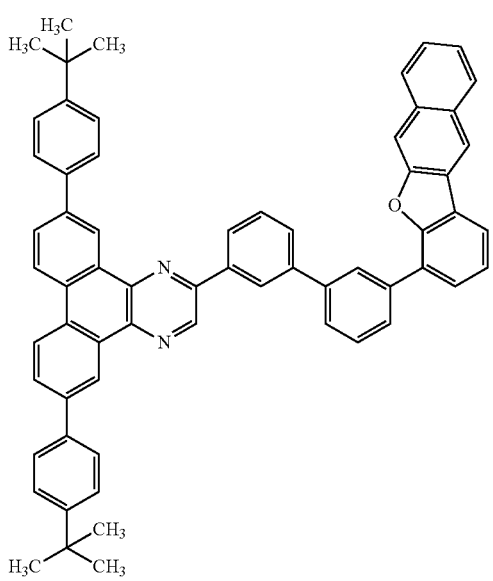
(117)
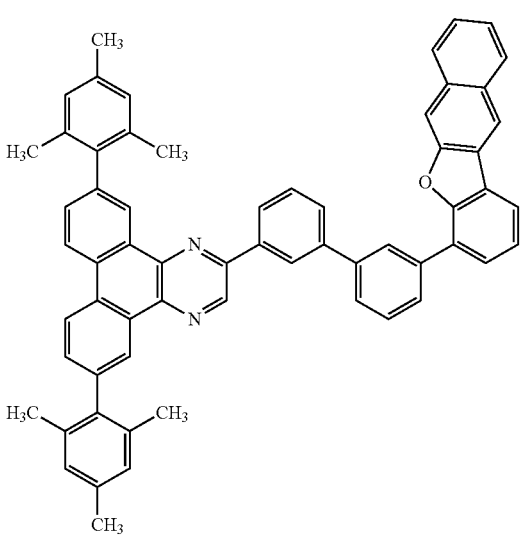
(118)

(119)
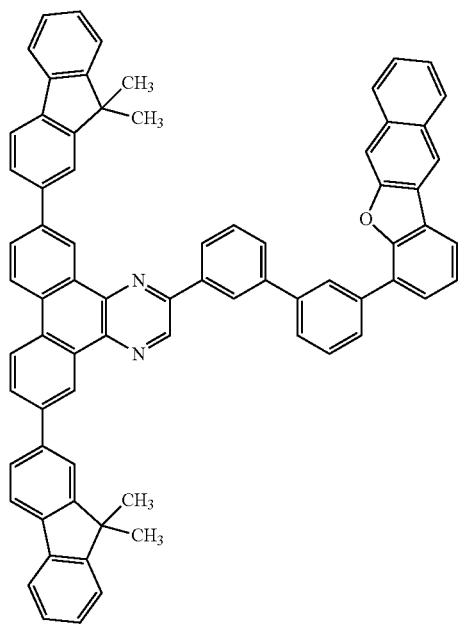
(120)
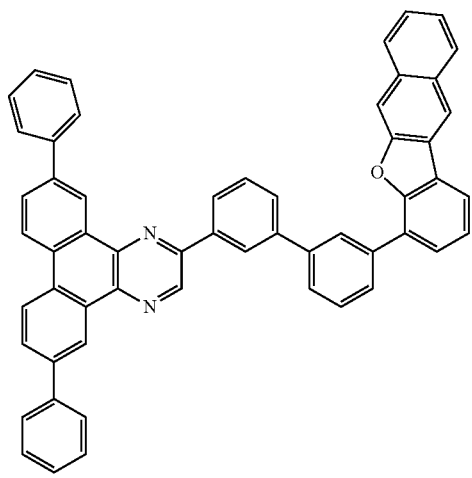
(121)
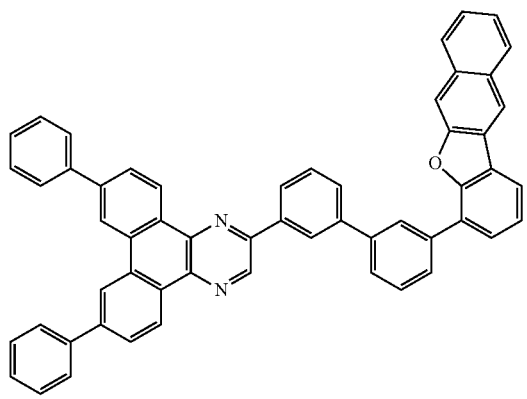
(122)
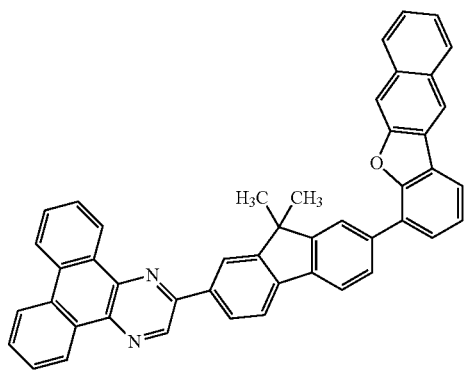
(123)
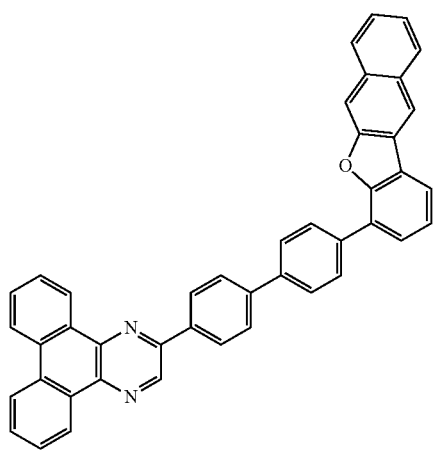
(124)
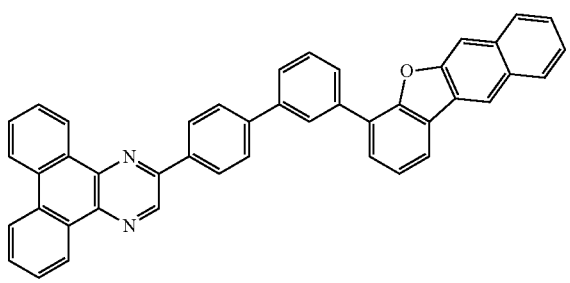

(125)
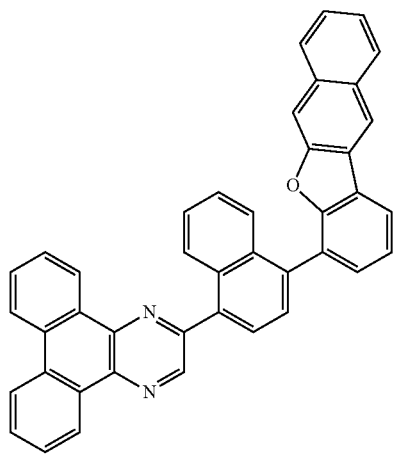
(126)
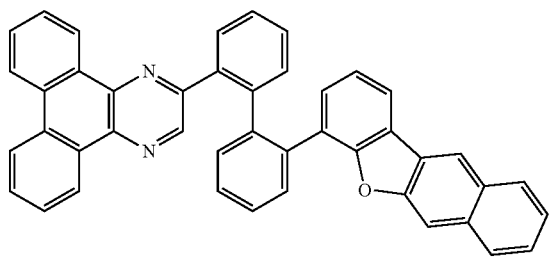
(127)
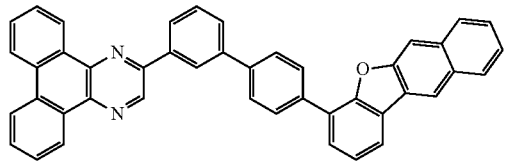
(128)
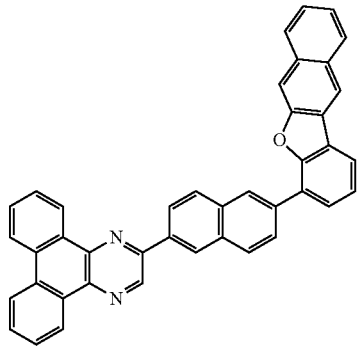
(129)
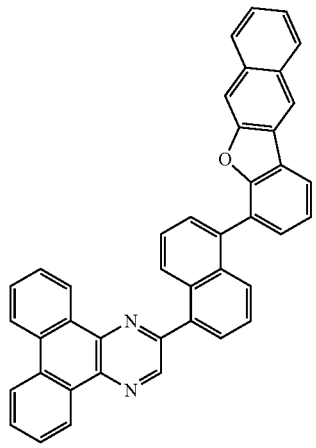
(130)
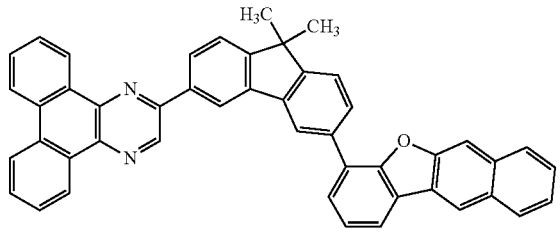

-continued
(131)
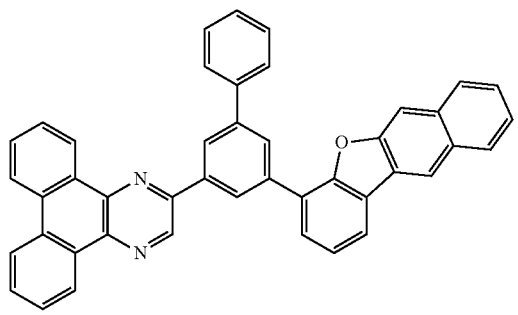
(132)
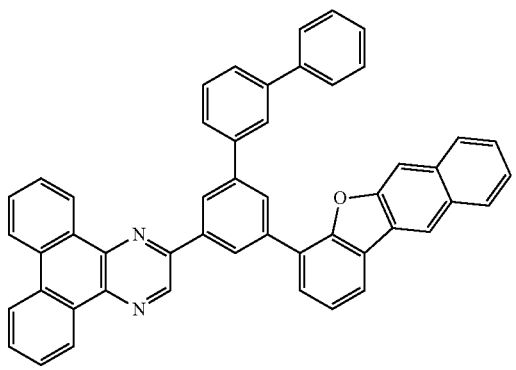
(133)
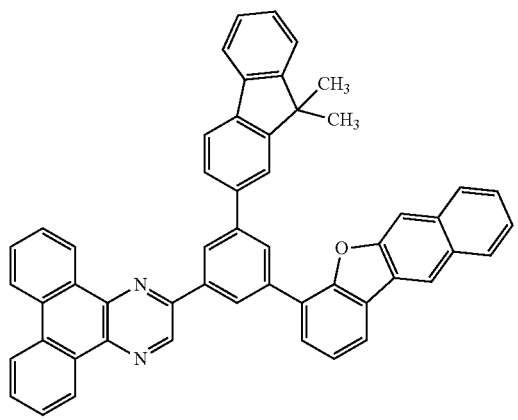
(134)
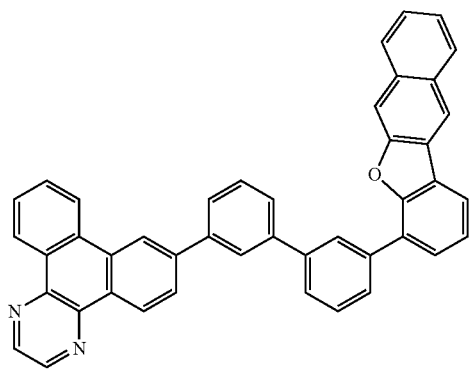
(135)
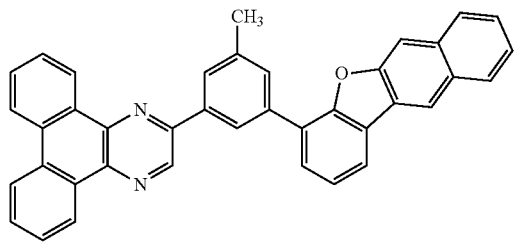
(136)
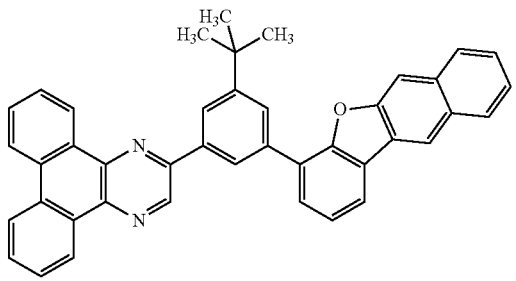
(137)
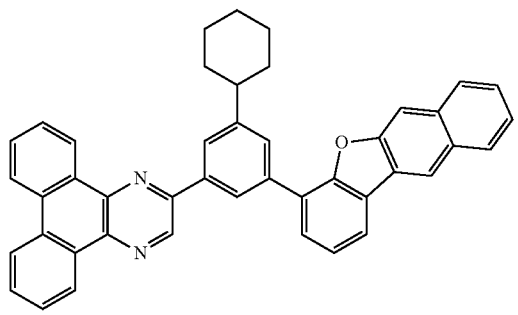
(138)
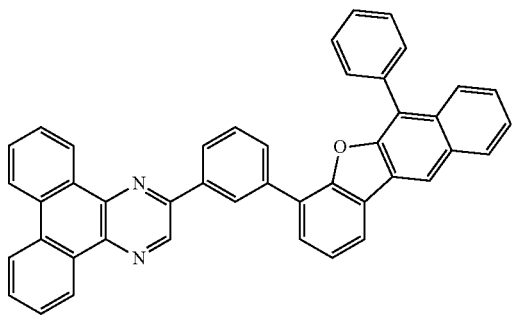

-continued
(139)
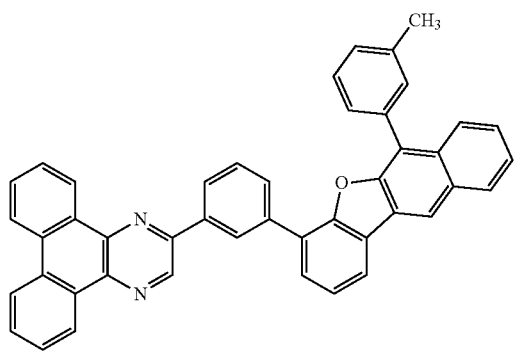
(140)
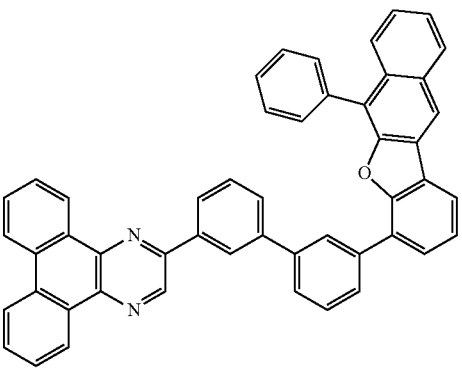
(141)
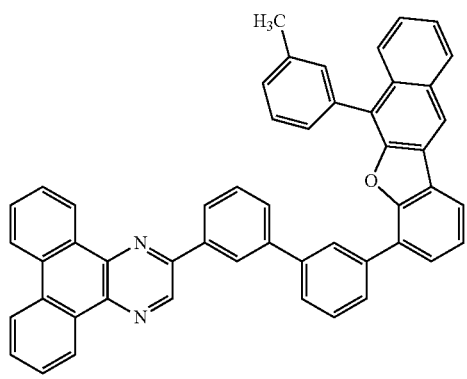
(142)
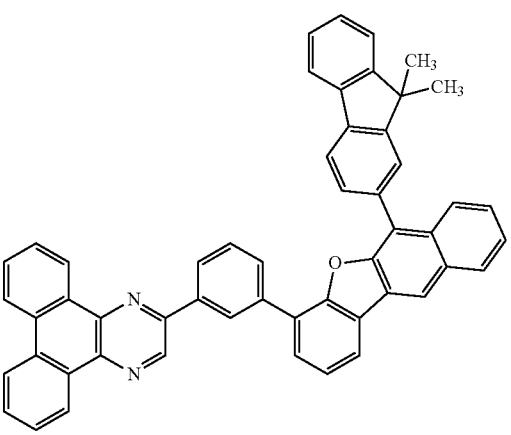
(143)
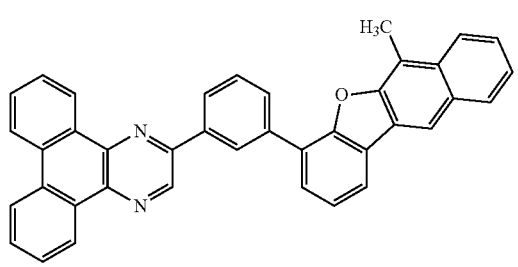
(144)
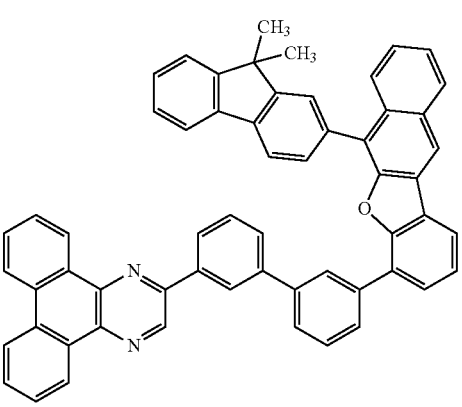
(145)
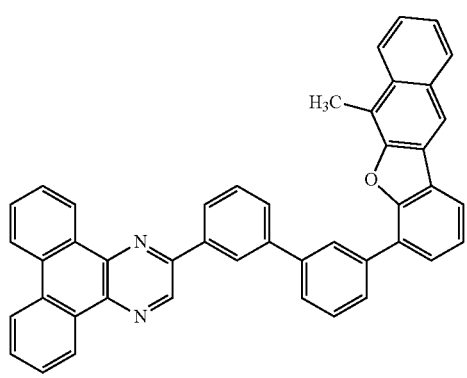
(146)
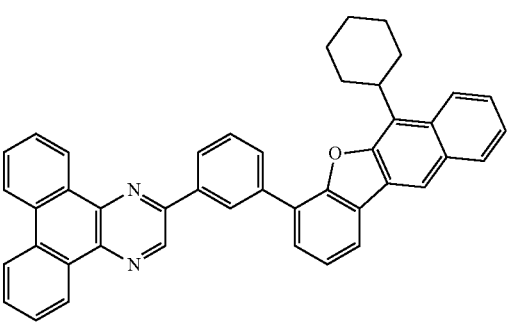

-continued
(147)
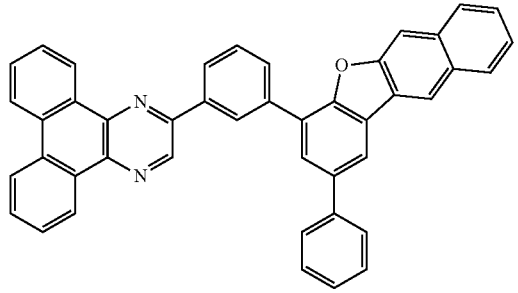
(148)
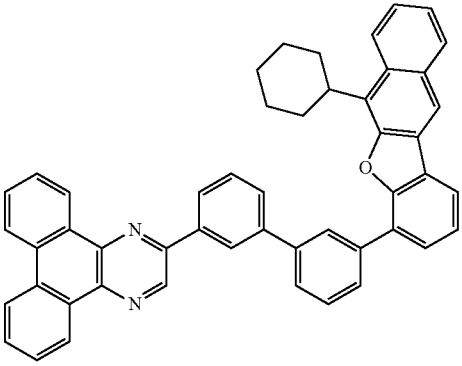
(149)
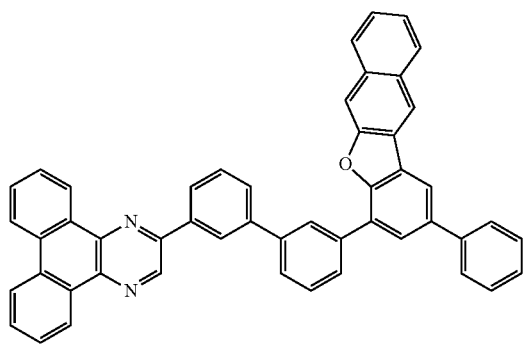
(150)
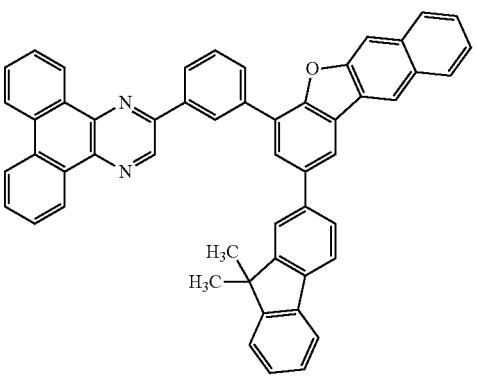
(151)
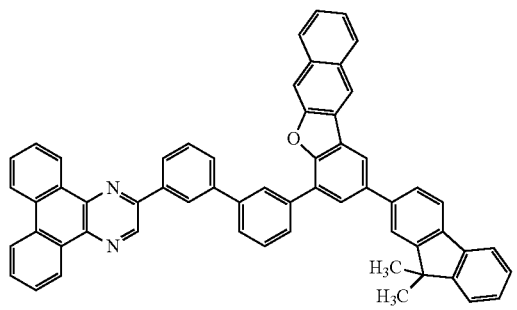
(152)
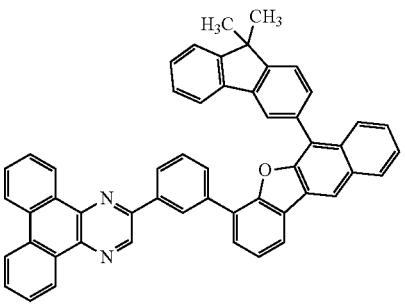
(153)
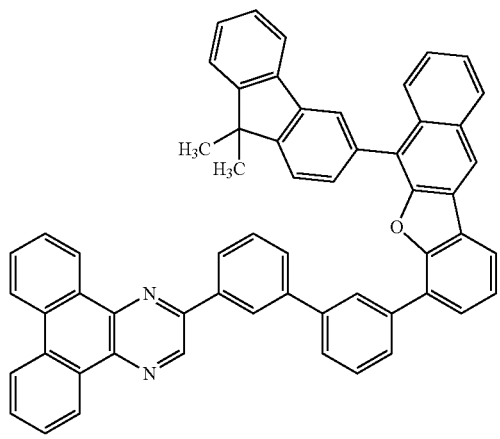
(154)
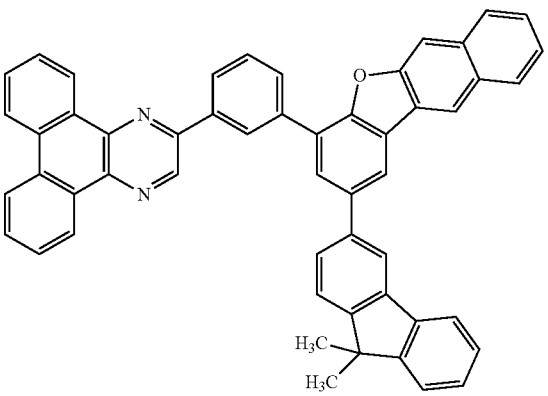

-continued (155)

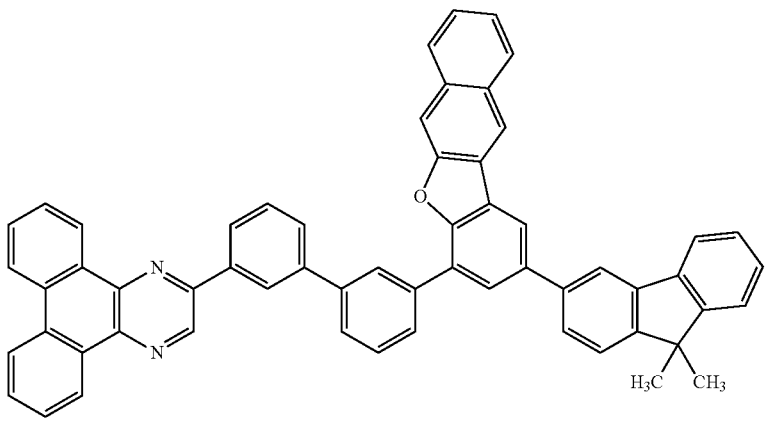

A variety of reactions can be applied to a method for synthesizing the compound of one embodiment of the present invention. As an example of a method for synthesizing the compound represented by General Formula (G0), a method for synthesizing the compound represented by General Formula (G1) in which $R^{10}$ is the substituent represented by General Formula (G1-1), i.e., a method for synthesizing the compound represented by General Formula (G2), is described below. Note that the methods for synthesizing the compound of one embodiment of the present invention are not limited to the synthesis methods below.

The compound represented by General Formula (G2) can be synthesized under Synthesis Scheme (A-1) below. That is, the compound represented by General Formula (G2) can be obtained by coupling of a benzo[b]naphtho[2,3-d]furan compound (Compound 1) and a dibenzo[f,h]quinoxaline compound (Compound 2).

(A-1)

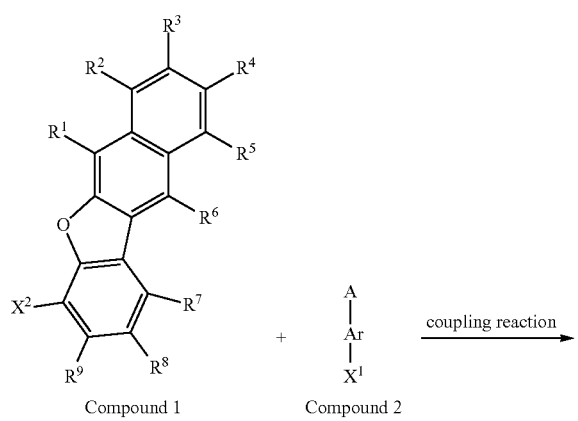

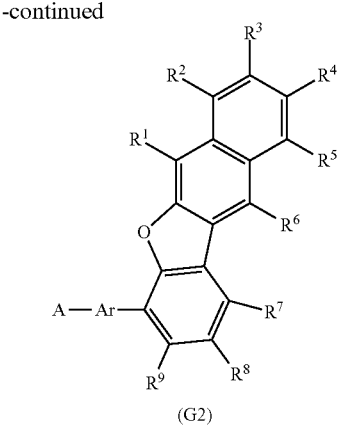

(G2)

In Synthesis Scheme (A-1), A represents a substituted or unsubstituted dibenzo[f,h]quinoxalinyl group; Ar represents a substituted or unsubstituted arylene group having 6 to 25 carbon atoms; $X^1$ and $X^2$ separately represent any one of a halogen, a trifluoromethanesulfonyl group, a boronic acid group, an organoboron group, a magnesium halide group, an organotin group, and the like; and $R^1$ to $R^9$ separately represent any one of hydrogen, an alkyl group having 1 to 6 carbon atoms, a cycloalkyl group having 3 to 6 carbon atoms, and a substituted or unsubstituted aryl group having 6 to 13 carbon atoms.

When a Suzuki-Miyaura coupling reaction using a palladium catalyst is performed under Synthesis Scheme (A-1), $X^1$ and $X^2$ separately represent any one of a halogen, a boronic acid group, an organoboron group, and a trifluoromethanesulfonyl group. It is preferable that the halogen be any one of iodine, bromine, and chlorine. In the reaction, a palladium compound such as bis(dibenzylideneacetone)palladium(0), palladium(II) acetate, [1,1'-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In addition, in the reaction, an organic base such as sodium tert-butoxide, an inorganic base such as potassium carbonate, cesium carbonate, or sodium carbonate, or the like can be used. Furthermore, in the reaction, toluene, xylene, benzene, tetrahydrofuran, dioxane, ethanol, methanol, water, or the like can be used as a solvent. The reagents that can be used in the reaction are not limited thereto.

The reaction performed under Synthesis Scheme (A–1) is not limited to a Suzuki-Miyaura coupling reaction, and a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be employed.

By a method similar to the above, it is also possible to synthesize a compound in which the substituent represented by General Formula (G1-1) is bonded to any one of the 1- to 10-positions of benzo[b]naphtho[2,3-d]furan (i.e., a compound represented by General Formula (G1) in which any one of $R^1$ to $R^{10}$ is the substituent represented by General Formula (G1-1)).

Thus, the compound of this embodiment can be synthesized.

A compound in which a halogen (iodine, bromine, or chlorine), a trifluoromethanesulfonyl group, a boronic acid group, an organoboron group, a magnesium halide group, an organotin group, or the like is bonded to the 8-position of benzo[b]naphtho[2,3-d]furan and which is used in synthesis of the compound of one embodiment of the present invention is also one embodiment of the present invention.

One embodiment of the present invention is a compound represented by General Formula (G4).

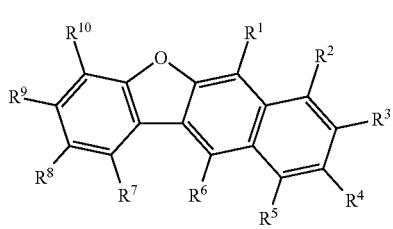

(G4)

In General Formula (G4), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms, and $R^{10}$ represents any one of chlorine, bromine, boron, iodine, a boronic acid group, and an organoboron group. The aryl group is unsubstituted or substituted by any one of an alkyl group having 1 to 6 carbon atoms, a cycloalkyl group having 3 to 6 carbon atoms, and an aryl group having 6 to 13 carbon atoms.

<Synthesis Method of Compound Represented by General Formula (G4)>

A method for synthesizing the compound represented by General Formula (G4) is described. Note that the methods for synthesizing the compound of one embodiment of the present invention represented by General Formula (G4) are not limited to the synthesis methods below.

The compound represented by General Formula (G4) can be synthesized under Synthesis Schemes (X-1) and (X-2) below, for example.

First, as shown in Synthesis Scheme (X-1), Compound 3 is coupled with Compound 4, so that an alcohol (Compound 5) can be obtained.

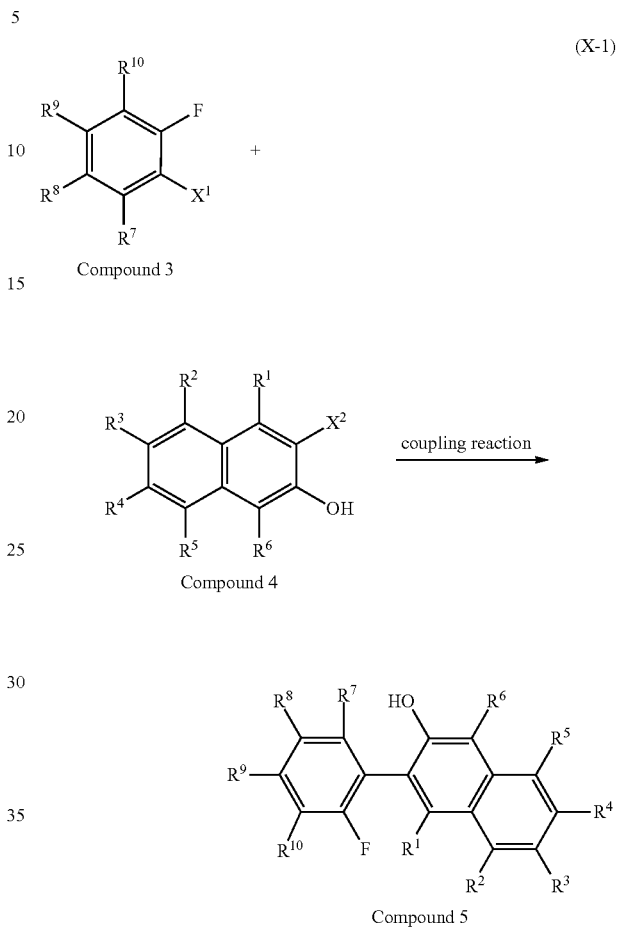

In Synthesis Scheme (X-1), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms; $R^{10}$ represents any one of chlorine, bromine, boron, iodine, a boronic acid group, and an organoboron group; and $X^1$ and $X^2$ separately represent any one of a halogen, a trifluoromethanesulfonyl group, a boronic acid group, an organoboron group, a magnesium halide group, an organotin group, and the like.

In Synthesis Scheme (X-1), the hydroxyl group in Compound 4 may be protected by an alkyl group or the like.

When a Suzuki-Miyaura coupling reaction using a palladium catalyst is performed under Synthesis Scheme (X-1), $X^1$ and $X^2$ separately represent any one of a halogen, a boronic acid group, an organoboron group, and a trifluoromethanesulfonyl group. It is preferable that the halogen be any one of iodine, bromine, and chlorine. In the reaction, a palladium compound such as bis(dibenzylideneacetone)palladium(0), palladium(II) acetate, [1,1'-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In addition, in the reaction, an organic base such as sodium tert-butoxide, an inorganic base such as potassium carbonate, cesium carbonate, or sodium carbonate, or the like can be used. Furthermore, in the reaction, toluene, xylene, benzene, tetrahydrofuran, dioxane, ethanol, methanol, water, or the like can be used as a solvent. Reagents that can be used in the reaction are not limited thereto.

The reaction performed under Synthesis Scheme (X-1) is not limited to a Suzuki-Miyaura coupling reaction, and a Migita-Kosugi-Stille coupling reaction using an organotin compound, a Kumada-Tamao-Corriu coupling reaction using a Grignard reagent, a Negishi coupling reaction using an organozinc compound, a reaction using copper or a copper compound, or the like can also be employed.

Then, as shown in Synthesis Scheme (X-2), an ether linkage is formed in the alcohol (Compound 5) by the Williamson synthesis, so that a benzo[b]naphtho[2,3-d]furan derivative (Compound 6) can be synthesized.

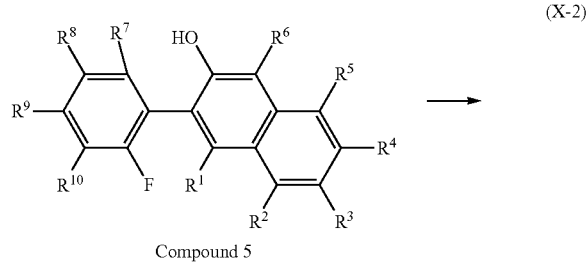

Compound 5

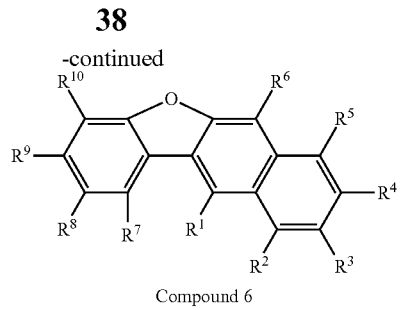

Compound 6

In Synthesis Scheme (X-2), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms, and $R^{10}$ represents any one of chlorine, bromine, boron, iodine, a boronic acid group, and an organoboron group.

In the case where the hydroxyl group in Compound 4 is protected by an alkyl group or the like in Synthesis Scheme (X-1), protecting deblocking needs to be performed using boron tribromide or the like before Synthesis Scheme (X-2) so that the protected hydroxyl group is returned to a hydroxyl group.

In the case where the Williamson synthesis is performed in Synthesis Scheme (X-2), a base such as potassium carbonate or sodium carbonate and a solvent such as N-methyl-2-pyrrolidone (NMP) can be used. Note that the base and the solvent which can be used are not limited thereto.

A method for synthesizing the compound of one embodiment of the present invention with the use of the compound (Compound 7) which is represented by General Formula (G4) and in which $R^{10}$ represents chlorine is described with reference to Synthesis Scheme (X-3).

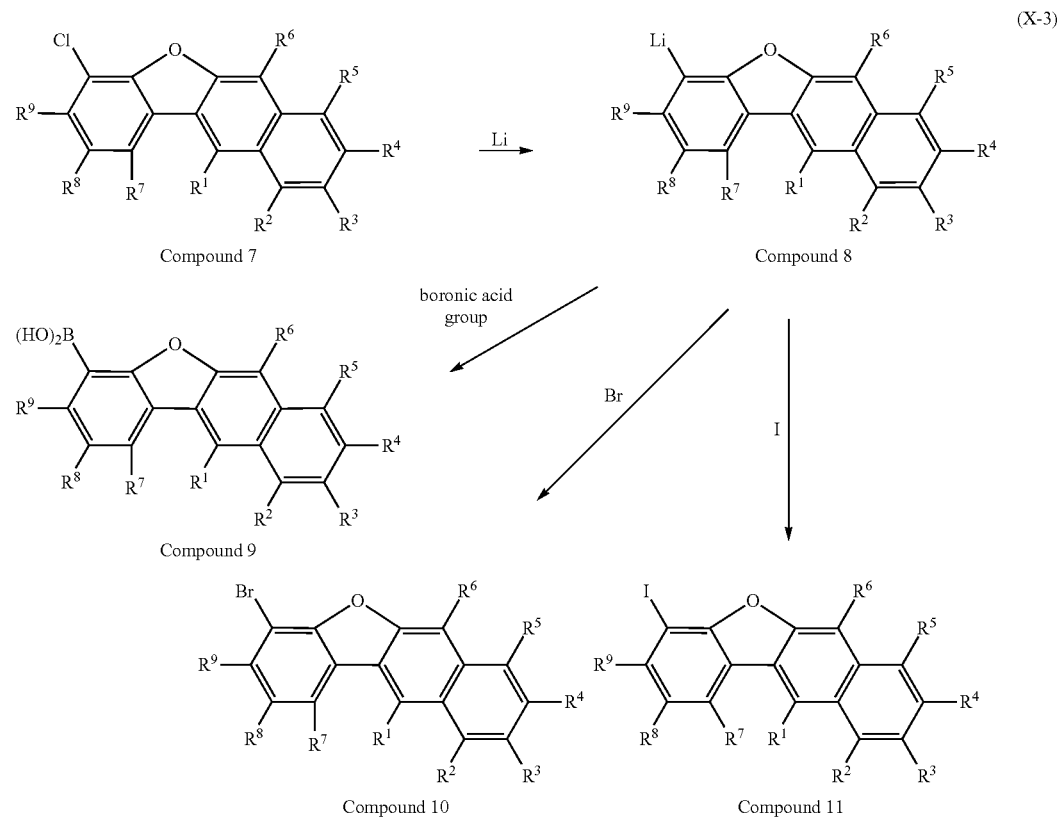

In Synthesis Scheme (X-3), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms.

In Synthesis Scheme (X-3), an organolithium compound (Compound 8), which is obtained by substitution of chlorine in the chlorine compound (Compound 7) with lithium, is used to perform substitution with a boronic acid group, substitution with bromine, or substitution with iodine, whereby a boronic acid compound (Compound 9), a bromine compound (Compound 10), or an iodine compound (Compound 11) can be synthesized.

Reagents that can be used for Synthesis Scheme (X-3) are as follows: an organolithium reagent such as n-butyllithium or t-butyllithium in the synthesis of the organolithium compound; trimethyl borate or the like in the substitution with a boronic acid group; iodine or the like in the substitution with iodine; and bromine or the like in the substitution with bromine. The reagents that can be used are not limited thereto.

Next, a method for synthesizing the compound (Compound 12) which is represented by General Formula (G4) and in which $R^{10}$ represents 4,4,5,5-tetramethyl-1,3,2-dioxaborolane is described with reference to Synthesis Scheme (X-4).

As shown in Synthesis Scheme (X-4), Compound 6 that is a halogen compound is coupled with bis(pinacolato)diboron, so that an organoboron compound (Compound 12) can be obtained. In Synthesis Scheme (X-4), a palladium compound such as bis(dibenzylideneacetone)palladium(0), palladium(II) acetate, [1,1'-bis(diphenylphosphino)ferrocene]palladium(II) dichloride, or tetrakis(triphenylphosphine)palladium(0) and a ligand such as tri(tert-butyl)phosphine, tri(n-hexyl)phosphine, tricyclohexylphosphine, di(1-adamantyl)-n-butylphosphine, 2-dicyclohexylphosphino-2',6'-dimethoxybiphenyl, or tri(ortho-tolyl)phosphine can be used. In addition, in the reaction, an organic base such as sodium tert-butoxide, an inorganic base such as potassium carbonate, cesium carbonate, or sodium carbonate, or the like can be used. Furthermore, in the reaction, toluene, xylene, benzene, tetrahydrofuran, dioxane, ethanol, methanol, water, or the like can be used as a solvent. Reagents that can be used in the reaction are not limited thereto.

Specific examples of the compound of one embodiment of the present invention include compounds represented by Structural Formulae (201) to (215). However, the present invention is not limited to these structural formulae.

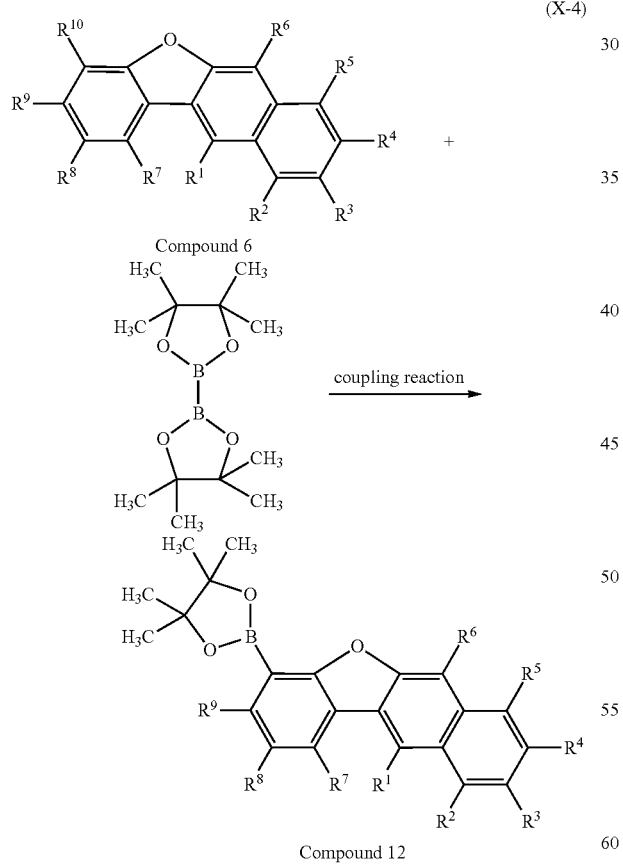

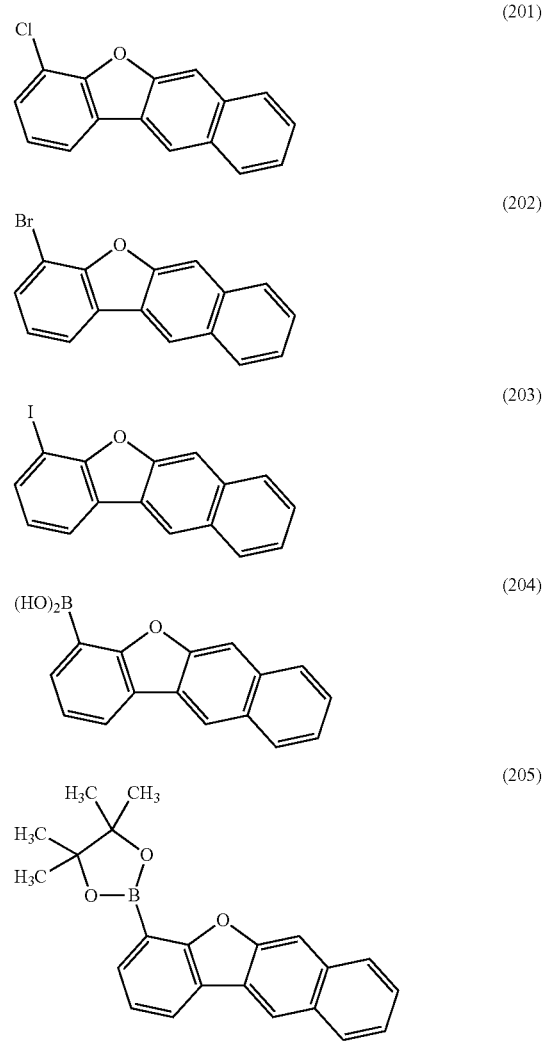

In Synthesis Scheme (X-4), $R^1$ to $R^9$ separately represent any one of hydrogen, an alkyl group having 1 to 6 carbon atoms, a cycloalkyl group having 3 to 6 carbon atoms, and an aryl group having 6 to 13 carbon atoms, and $R^{10}$ represents any one of chlorine, bromine, and iodine.

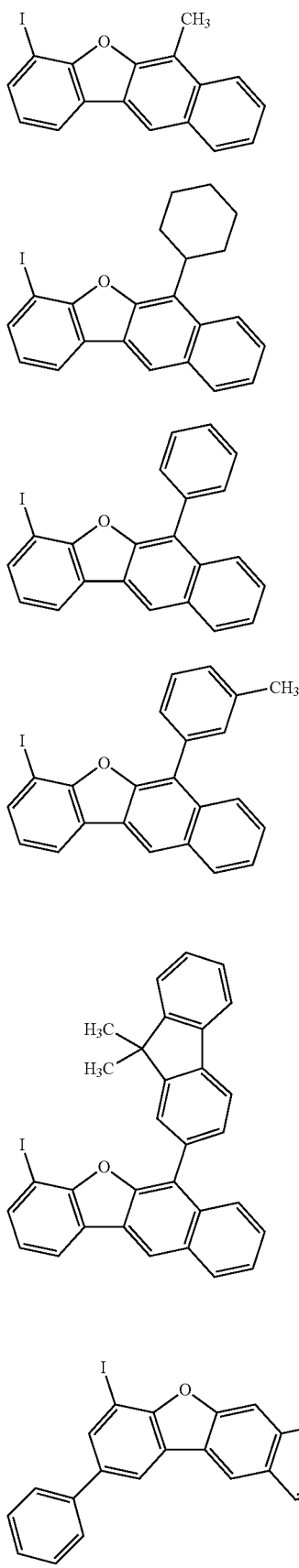
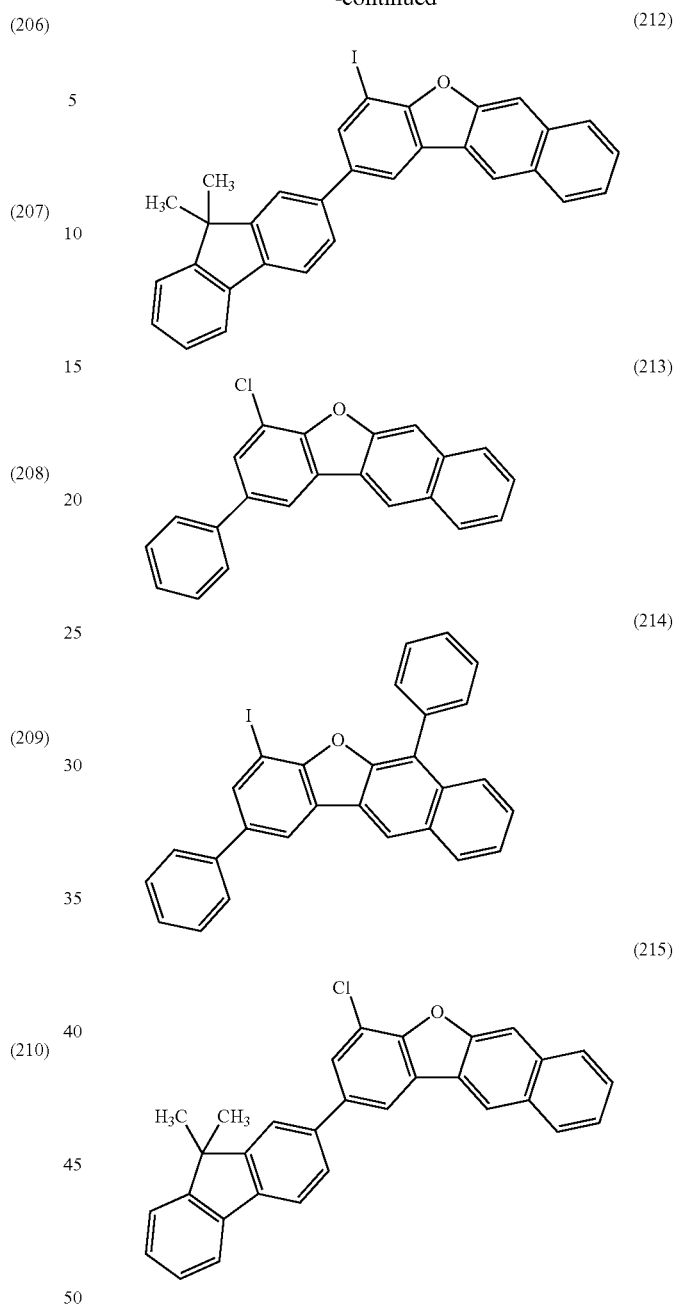

In a light-emitting element, the compound of this embodiment can be favorably used as a host material of a light-emitting layer, in which a light-emitting substance is dispersed, or a material of an electron-transport layer. By the use of the compound of this embodiment, a light-emitting element with a long lifetime can be provided.

This embodiment can be combined with any other embodiment as appropriate.

(Embodiment 2)

In this embodiment, light-emitting elements of embodiments of the present invention will be described with reference to FIGS. 1A to 1D.

A light-emitting element of one embodiment of the present invention has a layer containing the compound described in Embodiment 1 between a pair of electrodes.

The compound included in the light-emitting element of one embodiment of the present invention is sterically bulky and highly resistant to heat. In addition, the compound has high film quality. Accordingly, the use of the compound enables a light-emitting element to have a long lifetime.

Furthermore, the compound can accept electrons and holes since the compound has a dibenzo[f,h]quinoxaline skeleton as an electron-transport skeleton and a benzo[b]naphtho[2,3-d]furan skeleton as a hole-transport skeleton. Accordingly, by the use of the compound as a host material of a light-emitting layer, electrons and holes recombine in the light-emitting layer and it is possible to inhibit a reduction in lifetime of the light-emitting element. That is, a preferred embodiment of the present invention is a light-emitting element including, between a pair of electrodes, a light-emitting layer containing a light-emitting substance (guest material) and the above compound serving as a host material in which the light-emitting substance is dispersed.

The light-emitting element of this embodiment includes a layer (EL layer) containing a light-emitting organic compound between a pair of electrodes (a first electrode and a second electrode). One of the first electrode and the second electrode functions as an anode, and the other functions as a cathode. In this embodiment, the EL layer contains the compound of one embodiment of the present invention which is described in Embodiment 1.

<<Structural Example of Light-Emitting Element>>

A light-emitting element illustrated in FIG. 1A includes an EL layer 203 between a first electrode 201 and a second electrode 205. In this embodiment, the first electrode 201 serves as an anode and the second electrode 205 serves as a cathode.

When a voltage higher than the threshold voltage of the light-emitting element is applied between the first electrode 201 and the second electrode 205, holes are injected from the first electrode 201 side to the EL layer 203 and electrons are injected from the second electrode 205 side to the EL layer 203. The injected electrons and holes recombine in the EL layer 203 and a light-emitting substance contained in the EL layer 203 emits light.

The EL layer 203 includes at least a light-emitting layer 303 containing a light-emitting substance.

Furthermore, when a plurality of light-emitting layers are provided in the EL layer and emission colors of the layers are made different, light emission of a desired color can be provided from the light-emitting element as a whole. For example, the emission colors of first and second light-emitting layers are complementary in a light-emitting element having the two light-emitting layers, so that the light-emitting element can be made to emit white light as a whole. Note that "complementary colors" refer to colors that can produce an achromatic color when mixed. In other words, when light components obtained from substances that emit light of complementary colors are mixed, white emission can be obtained. Furthermore, the same applies to a light-emitting element having three or more light-emitting layers.

In addition to the light-emitting layer, the EL layer 203 may further include a layer containing a substance with a high hole-injection property, a substance with a high hole-transport property, a substance with a high electron-transport property, a substance with a high electron-injection property, a substance with a bipolar property (a substance with a high electron-transport property and a high hole-transport property), or the like. Either a low molecular compound or a high molecular compound can be used for the EL layer 203, and an inorganic compound may be used.

Figure 1B:
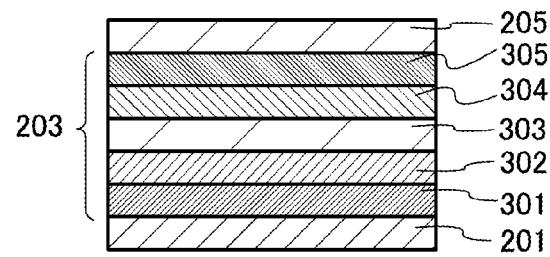

A light-emitting element illustrated in FIG. 1B includes the EL layer 203 between the first electrode 201 and the second electrode 205, and in the EL layer 203, a hole-injection layer 301, a hole-transport layer 302, the light-emitting layer 303, an electron-transport layer 304, and an electron-injection layer 305 are stacked in that order from the first electrode 201 side.

The compound of one embodiment of the present invention is preferably used for the light-emitting layer 303 or the electron-transport layer 304. In this embodiment, an example is described in which the compound of one embodiment of the present invention is used as the host material in the light-emitting layer 303.

Figure 1C:
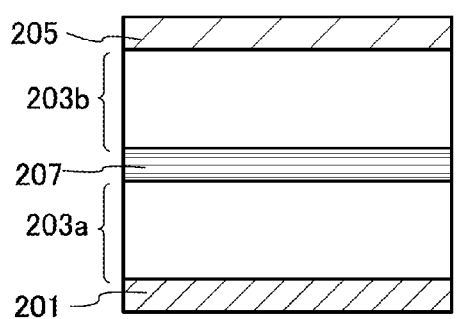
Figure 1D:
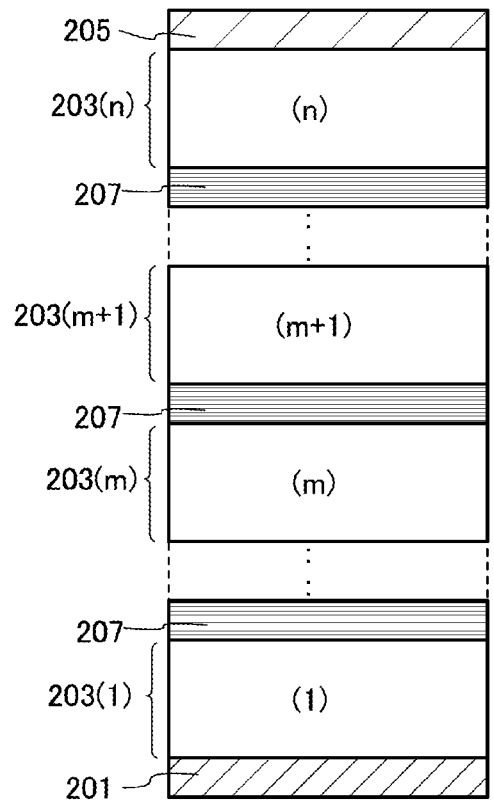

As in light-emitting elements illustrated in FIGS. 1C and 1D, a plurality of EL layers may be stacked between the first electrode 201 and the second electrode 205. In this case, an intermediate layer 207 is preferably provided between the stacked EL layers. The intermediate layer 207 includes at least a charge-generation region.

For example, the light-emitting element illustrated in FIG. 1C includes the intermediate layer 207 between a first EL layer 203a and a second EL layer 203b. The light-emitting element illustrated in FIG. 1D includes n EL layers (n is a natural number of 2 or more), and the intermediate layers 207 between the EL layers.

The behaviors of electrons and holes in the intermediate layer 207 provided between the EL layer 203($m$) and the EL layer 203($m$+1) will be described. When a voltage higher than the threshold voltage of the light-emitting element is applied between the first electrode 201 and the second electrode 205, holes and electrons are generated in the intermediate layer 207, and the holes move into the EL layer 203($m$+1) provided on the second electrode 205 side and the electrons move into the EL layer 203($m$) provided on the first electrode 201 side. The holes injected into the EL layer 203($m$+1) recombine with electrons injected from the second electrode 205 side, so that a light-emitting substance contained in the EL layer 203($m$+1) emits light. Furthermore, the electrons injected into the EL layer 203($m$) recombine with holes injected from the first electrode 201 side, so that a light-emitting substance contained in the EL layer 203($m$) emits light. Thus, the holes and electrons generated in the intermediate layer 207 cause light emission in different EL layers.

Note that the EL layers can be provided in contact with each other with no intermediate layer interposed therebetween when these EL layers allow the same structure as the intermediate layer to be formed therebetween. For example, when the charge-generation region is formed over one surface of an EL layer, another EL layer can be provided in contact with the surface.

Furthermore, when emission colors of the EL layers are made different, light emission of a desired color can be provided from the light-emitting element as a whole. For example, the emission colors of the first and second EL layers are complementary in a light-emitting element having the two EL layers, so that the light-emitting element can be made to emit white light as a whole. The same applies to a light-emitting element having three or more EL layers.

<<Materials of Light-Emitting Element>>

Examples of materials which can be used for each layer will be given below. Note that each layer is not limited to a single layer, and may be a stack including two or more layers.

<Anode>

The electrode serving as the anode (the first electrode 201 in this embodiment) can be formed using one or more kinds of conductive metals, conductive alloys, conductive compounds, and the like. In particular, it is preferable to use a material with a high work function (4.0 eV or more). The examples include indium tin oxide (ITO), indium tin oxide containing silicon or silicon oxide, indium zinc oxide, indium oxide containing tungsten oxide and zinc oxide, graphene, gold, platinum, nickel, tungsten, chromium, molybdenum, iron, cobalt, copper, palladium, titanium, and a nitride of a metal material (e.g., titanium nitride).

When the anode is in contact with the charge-generation region, any of a variety of conductive materials can be used regardless of their work functions; for example, aluminum, silver, an alloy containing aluminum, or the like can be used.

<Cathode>

The electrode serving as the cathode (the second electrode 205 in this embodiment) can be formed using one or more kinds of conductive metals, conductive alloys, conductive compounds, and the like. In particular, it is preferable to use a material with a low work function (3.8 eV or less). The examples include aluminum, silver, an element belonging to Group 1 or 2 of the periodic table (e.g., an alkali metal such as lithium or cesium, an alkaline earth metal such as calcium or strontium, or magnesium), an alloy containing any of these elements (e.g., Mg—Ag or Al—Li), a rare earth metal such as europium or ytterbium, and an alloy containing any of these rare earth metals.

Note that when the cathode is in contact with the charge-generation region, any of a variety of conductive materials can be used regardless of its work function. For example, ITO or indium tin oxide containing silicon or silicon oxide can be used.

The electrodes may be formed separately by a vacuum evaporation method or a sputtering method. Alternatively, when a silver paste or the like is used, a coating method or an inkjet method may be used.

<Light-Emitting Layer>

The light-emitting layer 303 contains a light-emitting substance. In an example described in this embodiment, the light-emitting layer 303 contains a guest material and a host material in which the guest material is dispersed and the compound of one embodiment of the present invention is used as the host material. The compound of one embodiment of the present invention can be favorably used as a host material in a light-emitting layer when a light-emitting substance is a phosphorescent compound emitting light in a wavelength range from red to green or a fluorescent compound.

When the light-emitting layer has the structure in which the guest material is dispersed in the host material, the crystallization of the light-emitting layer can be inhibited. Furthermore, it is possible to inhibit concentration quenching due to high concentration of the guest material; thus, the light-emitting element can have higher emission efficiency.

In addition to the guest material and the host material, the light-emitting layer may contain another compound. Furthermore, in addition to the light-emitting layer containing the compound of one embodiment of the present invention, the light-emitting element of one embodiment of the present invention may include another light-emitting layer. In that case, a fluorescent compound, a phosphorescent compound, or a substance emitting thermally activated delayed fluorescence can be used as the light-emitting substance, and a compound to be described below which easily accepts electrons or a compound to be described below which easily accepts holes can be used as the host material.

Note that it is preferable that the $T_1$ level of the host material (or a material other than the guest material in the light-emitting layer) be higher than the $T_1$ level of the guest material. This is because, when the $T_1$ level of the host material is lower than that of the guest material, the triplet excitation energy of the guest material, which is to contribute to light emission, is quenched by the host material and accordingly the emission efficiency is reduced.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) have a large overlap with an absorption spectrum of a guest material (specifically, spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, because the phosphorescence spectrum of the host material is located on the longer wavelength (lower energy) side than the fluorescence spectrum, the $T_1$ level of the host material becomes lower than the $T_1$ level of the phosphorescent compound and the above-described problem of quenching occurs; yet, when the host material is designed in such a manner that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For this reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, it is preferable that in a light-emitting layer of a light-emitting element which uses a phosphorescent compound as a guest material, a third substance be contained in addition to the phosphorescent compound and the host material (which are respectively regarded as a first substance and a second substance contained in the light-emitting layer), and the host material forms an exciplex (also referred to as excited complex) in combination with the third substance. In that case, the host material and the third substance form an exciplex at the time of recombination of carriers (electrons and holes) in the light-emitting layer. Thus, in the light-emitting layer, fluorescence spectra of the host material and the third substance are converted into an emission spectrum of the exciplex which is located on a longer wavelength side. Moreover, when the host material and the third substance are selected such that the emission spectrum of the exciplex has a large overlap with the absorption spectrum of the guest material, energy transfer from a singlet excited state can be maximized. Note that also in the case of a triplet excited state, energy transfer from the exciplex, not the host material, is considered to occur. In one embodiment of the present invention to which such a structure is applied, energy transfer efficiency can be improved owing to energy transfer utilizing an overlap between an emission spectrum of an exciplex and an absorption spectrum of a phosphorescent compound; accordingly, a light-emitting element with high external quantum efficiency can be provided.

As the guest material, a phosphorescent compound to be described below can be used. Although any combination of the host material and the third substance can be used as long as an exciplex is formed, a compound which easily accepts electrons (a compound having an electron-trapping property) and a compound which easily accepts holes (a compound having a hole-trapping property) are preferably combined. The compound of one embodiment of the present invention can be used as a compound having an electron-trapping property.

Thus, the light-emitting element of one embodiment of the present invention includes, between a pair of electrodes, a light-emitting layer containing a phosphorescent compound emitting light in a wavelength range from red to green, the compound of one embodiment of the present invention, and a compound which easily accepts holes.

Examples of a compound which easily accepts holes and which can be used as the host material or the third substance are a π-electron rich heteroaromatic compound (e.g., a carbazole derivative or an indole derivative) and an aromatic amine compound.

Specifically, the following examples can be given: N-(1,1'-biphenyl-4-yl)-N-[4-(9-phenyl-9H-carbazol-3-yl)phenyl]-9,9-dimethyl-9H-fluoren-2-amine (abbreviation: PCBBiF), 4-phenyl-4'-(9-phenyl-9H-carbazol-3-yl)triphenylamine (abbreviation: PCBAlBP), 4,4'-di(1-naphthyl)-4''-(9-phenyl-9H-carbazol-3-yl)triphenylamine (abbreviation: PCBNBB), 3-[N-(1-naphthyl)-N-(9-phenyl-carbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]spiro-9,9'-bifluorene (abbreviation: DPA2 SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N''-triphenyl-N,N',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N-phenyl-N-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N-(3-methylphenyl)-N-phenylamino]phenyl}-N-phenylamino)biphenyl (abbreviation: DNTPD), and 3,6-bis[N-(4-diphenylamino-phenyl)-N-(1-naphthyl)amino]-9-phenylcarbazole (abbreviation: PCzTPN2).

The following examples can also be given: aromatic amine compounds such as 4,4'-bis[N-(1-naphthyl)-N-phenylamino]biphenyl (abbreviation: NPB or α-NPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4,4',4''-tris(N-carbazolyl)triphenylamine (abbreviation: TCTA), 4-phenyl-4'-(9-phenylfluoren-9-yl)triphenylamine (abbreviation: BPAFLP), and 4,4'-bis[N-(9,9-dimethylfluoren-2-yl)-N-phenylamino]biphenyl (abbreviation: DFLDPBi); and carbazole derivatives such as 4,4'-di(N-carbazolyl)biphenyl (abbreviation: CBP), 9-[4-(10-phenyl-9-anthracenyl)phenyl]-9H-carbazole (abbreviation: CzPA), and 9-phenyl-3-[4-(10-phenyl-9-anthryl)phenyl]-9H-carbazole (abbreviation: PCzPA). In addition, high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD) can be given.

Examples of the compound which easily accepts electrons and which can be used as the host material or the third substance include the compound of one embodiment of the present invention, a π-electron deficient heteroaromatic compound such as a nitrogen-containing heteroaromatic compound, a metal complex having a quinoline skeleton or a benzoquinoline skeleton, and a metal complex having an oxazole-based ligand or a thiazole-based ligand.

Specific examples include the following: metal complexes such as bis(10-hydroxybenzo[h]quinolinato)beryllium (abbreviation: BeBq$_2$), bis(2-methyl-8-quinolinolato)(4-phenylphenolato)aluminum (abbreviation: BAlq), bis(8-quinolinolato)zinc (II) (abbreviation: Znq), bis[2-(2-hydroxyphenyl)benzoxazolato]zinc (abbreviation: Zn(BOX)$_2$), and bis[2-(2-hydroxyphenyl)benzothiazolato]zinc (abbreviation: Zn(BTZ)$_2$); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having quinoxaline skeletons or dibenzoquinoxaline skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl] dibenzo[f,h]quinoxaline (abbreviation: 7mDBTP-DBq-II), 6-[3-(dibenzothiophen-4-yl)phenyl]dibenzo[f,h]quinoxaline (abbreviation: 6mDBTPDBq-II), and 2-[3'-(9H-carbazol-9-yl)biphenyl-3-yl]dibenzo[f,h]quinoxaline (abbreviation: 2mCzBPDBq); heterocyclic compounds having diazine skeletons (pyrimidine skeletons or pyrazine skeletons), such as 4,6-bis[3-(phenanthren-9-yl)phenyl]pyrimidine (abbreviation: 4,6mPnP2Pm), 4,6-bis[3-(9H-carbazol-9-yl)phenyl]pyrimidine (abbreviation: 4,6mCzP2Pm), and 4,6-bis[3-(4-dibenzothienyl)phenyl]pyrimidine (abbreviation: 4,6mDBTP2Pm-II); and heterocyclic compounds having pyridine skeletons, such as 3,5-bis[3-(9H-carbazol-9-yl)phenyl]pyridine (abbreviation: 3,5 DCzPPy), 1,3,5-tri [3-(3-pyridyl)phenyl]benzene (abbreviation: TmPyPB), and 3,3',5,5'-tetra[(m-pyridyl)-phen-3-yl]biphenyl (abbreviation: BP4mPy). Among the above materials, heterocyclic compounds having quinoxaline skeletons or dibenzoquinoxaline skeletons, heterocyclic compounds having diazine skeletons, and heterocyclic compounds having pyridine skeletons are preferable because of their high reliability.

The following examples can also be given: metal complexes having quinoline skeletons or benzoquinoline skeletons, such as tris(8-quinolinolato)aluminum (abbreviation: Alq) and tris(4-methyl-8-quinolinolato)aluminum (abbreviation: Almq$_3$); and heteroaromatic compounds such as bathophenanthroline (abbreviation: BPhen), bathocuproine (abbreviation: BCP), 3-(4-tert-butylphenyl)-4-(4-ethylphenyl)-5-(4-biphenylyl)-1,2,4-triazole (abbreviation: p-EtTAZ), and 4,4'-bis(5-methylbenzoxazol-2-yl)stilbene (abbreviation: BzOs). In addition, high molecular compounds such as poly(2,5-pyridinediyl) (abbreviation: PPy), poly[(9, 9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can be given.

The materials which can be used as the host material or the third substance are not limited to the above materials as long as the material used as the host material forms an exciplex in combination with the material used as the third substance, an emission spectrum of the exciplex overlaps with an absorption spectrum of the guest material, and a peak of the emission spectrum of the exciplex is located on a longer wavelength side than a peak of the absorption spectrum of the guest material.

Note that when a compound which easily accepts electrons and a compound which easily accepts holes are used for the host material and the third substance, carrier balance can be controlled by the mixture ratio of the compounds. Specifically, the ratio of the host material to the third substance is preferably from 1:9 to 9:1.

Furthermore, the exciplex may be formed at the interface between two layers. For example, when a layer containing the compound which easily accepts electrons and a layer containing the compound which easily accepts holes are stacked, the exciplex is formed in the vicinity of the interface thereof. These two layers may be used as the light-emitting layer in the light-emitting element of one embodiment of the present invention. In that case, the phosphorescent compound may be added to the vicinity of the interface. The phosphorescent compound may be added to one of the two layers or both.

<<Guest Material>>

Examples of fluorescent compounds that can be used for the light-emitting layer 303 are given. Examples of materials that emit blue light are as follows: N,N'-bis(3-methylphenyl)-N,N'-bis[3-(9-phenyl-9H-fluoren-9-yl)phenyl]pyrene-1,6-diamine (abbreviation: 1,6mMemFLPAPrn), N,N'-bis(dibenzofuran-4-yl)-N,N-diphenylpyrene-1,6-diamine (abbreviation: 1,6FrAPrn-II), N,N-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and 4-(10-phenyl-9-anthryl)-4'-(9-phenyl-9H-carbazol-3-yl)triphenylamine (abbreviation: PCBAPA). Examples of materials that emit green light are as follows: N-(9,10-diphenyl-2-anthryl)-N, 9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), and N,N,9-triphenylanthracen-9-amine (abbreviation: DPhAPhA). Examples of materials that emit yellow light are as follows: rubrene and 5,12-bis (1,1'-biphenyl-4-yl)-6,11-diphenyltetracene (abbreviation: BPT). Examples of materials that emit red light are as follows: N,N,N',N'-tetrakis(4-methylphenyl)tetracene-5,11-diamine (abbreviation: p-mPhTD) and 7,14-diphenyl-N,N, N',N'-tetrakis(4-methylphenyl)acenaphtho[1,2-α]fluoranthene-3,10-diamine (abbreviation: p-mPhAFD).

Examples of phosphorescent compounds that can be used for the light-emitting layer 303 are given. For example, a phosphorescent compound having an emission peak at 440 nm to 520 nm is given, examples of which include organometallic iridium complexes having 4H-triazole skeletons, such as tris {2-[5-(2-methylphenyl)-4-(2,6-dimethylphenyl)-4H-1,2,4-triazol-3-yl-κN2]phenyl-κ C}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato] iridium(III) (abbreviation: [Ir(iPrptz-3b)$_3$]); organometallic iridium complexes having 1H-triazole skeletons, such as tris[3-methyl-1-(2-methylphenyl)-5-phenyl-1H-1,2,4-triazolato]iridium(III) (abbreviation: [Ir (Mptz1-mp)$_3$]) and tris(1-methyl-5-phenyl-3-propyl-1H-1, 2,4-triazolato)iridium(III) (abbreviation: [Ir(Prptzl-Me)$_3$]); organometallic iridium complexes having imidazole skeletons, such as fac-tris[1-(2,6-diisopropylphenyl)-2-phenyl-1H-imidazole] iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$] iridium(III) picolinate (abbreviation: FIrpic), bis{2-[3',5'-bis(trifluoromethyl)phenyl]pyridinato-N,$C^{2'}$}iridium(III) picolinate (abbreviation: [Ir(CF3ppy)$_2$(pic)]), and bis[2-(4',6'-difluorophenyl)pyridinato-N,$C^{2'}$]iridium(III) acetylacetonate (abbreviation: FIr(acac)). Among the materials given above, the organometallic iridium complexes having 4H-triazole skeletons have high reliability and high emission efficiency and are thus especially preferable.

Examples of the phosphorescent compound having an emission peak at 520 nm to 600 nm include organometallic iridium complexes having pyrimidine skeletons, such as tris(4-methyl-6-phenylpyrimidinato)iridium(III) (abbreviation: [Ir(mppm)$_3$]), tris(4-t-butyl-6-phenylpyrimidinato) iridium(III) (abbreviation: [Ir(tBuppm)$_3$]), (acetylacetonato) bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[4-(2-norbornyl)-6-phenylpyrimidinato]iridium(III) (endo- and exo-mixture) (abbreviation: [Ir(nbppm)$_2$(acac)]), (acetylacetonato)bis[5-methyl-6-(2-methylphenyl)-4-phenylpyrimidinato]iridium (III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having pyrazine skeletons, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having pyridine skeletons, such as tris (2-phenylpyridinato-N,$C^{2'}$)iridium(III) (abbreviation: [Ir (ppy)$_3$]), bis(2-phenylpyridinato-N,$C^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium (III) (abbreviation: [Ir(bzq)$_3$]), tris(2-phenylquinolinato-N,C$^{2'}$)iridium(III) (abbreviation: [Ir(pq)$_3$]), and bis(2-phenylquinolinato-N,C$^{2'}$)iridium(III) acetylacetonate (abbreviation: [Ir(pq)$_2$(acac)]); and a rare earth metal complex such as tris(acetylacetonato)(monophenanthroline)terbium(III) (abbreviation: [Tb(acac)$_3$(Phen)]). Among the above materials, the organometallic iridium complexes having pyrimidine skeletons are particularly preferable because of their distinctively high reliability and emission efficiency.

Examples of the phosphorescent compound having an emission peak at 600 nm to 700 nm include organometallic iridium complexes having pyrimidine skeletons, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(dlnpm)$_2$(dpm)]); organometallic iridium complexes having pyrazine skeletons, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having pyridine skeletons, such as tris(1-phenylisoquinolinato-N,C$^{2'}$)iridium(III) (abbreviation: [Ir(piq)$_3$]) and bis(1-phenylisoquinolinato-N,C$^{2'}$)iridium(III) acetylacetonate (abbreviation: [Ir(piq)$_2$(acac)]); a platinum complex such as 2,3,7,8,12,13,17,18-octaethyl-21H,23H-porphyrin platinum (II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). Among the materials given above, the organometallic iridium complexes having pyrimidine skeletons have distinctively high reliability and emission efficiency and are thus especially preferable. Furthermore, the organometallic iridium complexes having pyrazine skeletons can provide red light emission with favorable chromaticity.

Alternatively, a high molecular compound can be used for the light-emitting layer 303. Examples of the materials that emit blue light include poly(9,9-dioctylfluorene-2,7-diyl) (abbreviation: POF), poly[(9,9-dioctylfluorene-2,7-diyl)-co-(2,5-dimethoxybenzene-1,4-diyl)] (abbreviation: PF-DMOP), and poly{(9,9-dioctylfluorene-2,7-diyl)-co-[N,N'-di-(p-butylphenyl)-1,4-diaminobenzene]} (abbreviation: TAB-PFH). Examples of the materials that emit green light include poly(p-phenylenevinylene) (abbreviation: PPV), poly[(9,9-dihexylfluorene-2,7-diyl)-alt-co-(benzo[2,1,3]thiadiazole-4,7-diyl)] (abbreviation: PFBT), and poly[(9,9-dioctyl-2,7-divinylenefluorenylene)-alt-co-(2-methoxy-5-(2-ethylhexyloxy)-1,4-phenylene)]. Examples of the materials that emit orange to red light include poly[2-methoxy-5-(2-ethylhexoxy)-1,4-phenylenevinylene] (abbreviation: MEH-PPV), poly(3-butylthiophene-2,5-diyl), poly{[9,9-dihexyl-2,7-bis(1-cyanovinylene)fluorenylene]-alt-co-[2,5-bis(N,N'-diphenyla mino)-1,4-phenylene]}, and poly{[2-methoxy-5-(2-ethylhexyloxy)-1,4-bis(1-cyanovinylenephenylene)]-alt-co-[2,5-bis(N,N'-diphenylamino)-1,4-phenylene]} (abbreviation: CN-PPV-DPD).

<Hole-Transport Layer>

The hole-transport layer 302 contains a substance with a high hole-transport property.

The substance with a high hole-transport property is a substance having a hole-transport property higher than an electron-transport property, and is especially preferably a substance with a hole mobility of $10^{-6}$ cm$^2$/Vs or more.

For the hole-transport layer 302, it is possible to use any of the compounds which easily accept holes and are described as examples of the substance applicable to the light-emitting layer 303.

It is also possible to use an aromatic hydrocarbon compound such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth).

<Electron-transport Layer>

The electron-transport layer 304 contains a substance with a high electron-transport property.

The substance with a high electron-transport property is an organic compound having an electron-transport property higher than a hole-transport property, and is especially preferably a substance with an electron mobility of $10^{-6}$ cm$^2$/Vs or more.

For the electron-transport layer 304, it is possible to use any of the compounds which easily accept electrons and are described as examples of the substance applicable to the light-emitting layer 303.

<Hole-Injection Layer>

The hole-injection layer 301 contains a substance with a high hole-injection property.

Examples of the substance with a high hole-injection property include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Alternatively, it is possible to use a phthalocyanine-based compound such as phthalocyanine (abbreviation: H2Pc) or copper(II) phthalocyanine (abbreviation: CuPc).

Further alternatively, it is possible to use an aromatic amine compound which is a low molecular organic compound, such as TDATA, MTDATA, DPAB, DNTPD, 1,3,5-tris[N-(4-diphenylaminophenyl)-N-phenylamino]benzene (abbreviation: DPA3B), PCzPCA1, PCzPCA2, or PCz-PCN1.

Further alternatively, it is possible to use a high molecular compound such as PVK, PVTPA, PTPDMA, or Poly-TPD, or a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS).

The hole-injection layer 301 may serve as the charge-generation region. When the hole-injection layer 301 in contact with the anode serves as the charge-generation region, any of a variety of conductive materials can be used for the anode regardless of their work functions. Materials contained in the charge-generation region will be described later.

<Electron-Injection Layer>

The electron-injection layer 305 contains a substance with a high electron-injection property.

Examples of the substance with a high electron-injection property include an alkali metal, an alkaline earth metal, a rare earth metal, and a compound thereof (e.g., an oxide thereof, a carbonate thereof, and a halide thereof), such as lithium, cesium, calcium, lithium oxide, lithium carbonate, cesium carbonate, lithium fluoride, cesium fluoride, calcium fluoride, and erbium fluoride. Electride can also be used. As an example of electride, a substance in which electrons are added at high concentration to an oxide containing calcium and aluminum can be given.

The electron-injection layer 305 may serve as the charge-generation region. When the electron-injection layer 305 in contact with the cathode serves as the charge-generation region, any of a variety of conductive materials can be used for the cathode regardless of their work functions. Materials contained in the charge-generation region will be described later.

<Charge-Generation Region>

The charge-generation region may have either a structure in which an electron acceptor (acceptor) is added to an organic compound with a high hole-transport property or a structure in which an electron donor (donor) is added to an organic compound with a high electron-transport property. Alternatively, these structures may be stacked.

As examples of an organic compound with a high hole-transport property, the above materials which can be used for the hole-transport layer can be given, and as examples of an organic compound with a high electron-transport property, the above materials which can be used for the electron-transport layer can be given.

Furthermore, as the electron acceptor, 7,7,8,8-tetracyano-2,3,5,6-tetrafluoroquinodimethane (abbreviation: F4-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable because of their high electron-accepting properties. Among these, molybdenum oxide is especially preferable since it is stable in the air, has a low hygroscopic property, and is easy to handle.

Furthermore, as the electron donor, it is possible to use an alkali metal, an alkaline earth metal, a rare earth metal, a metal belonging to Group 2 or Group 13 of the periodic table, or an oxide or a carbonate thereof. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

The above-described layers included in the EL layer 203 and the intermediate layer 207 can be formed separately by any of the following methods: an evaporation method (including a vacuum evaporation method), a transfer method, a printing method, an inkjet method, a coating method, and the like.

This embodiment can be freely combined with any of other embodiments.

(Embodiment 3)

In this embodiment, light-emitting devices of embodiments of the present invention will be described with reference to FIGS. 2A and 2B and FIGS. 3A to 3C.

Light-emitting devices including the light-emitting element of one embodiment of the present invention are described in this embodiment as examples. Since the light-emitting element has a long lifetime, light-emitting devices having high reliability can be provided.

Note that one embodiment of the present invention is not limited to these examples, and the light-emitting element of one embodiment of the present invention and the compound of one embodiment of the present invention are not necessarily included.

Figure 2A:
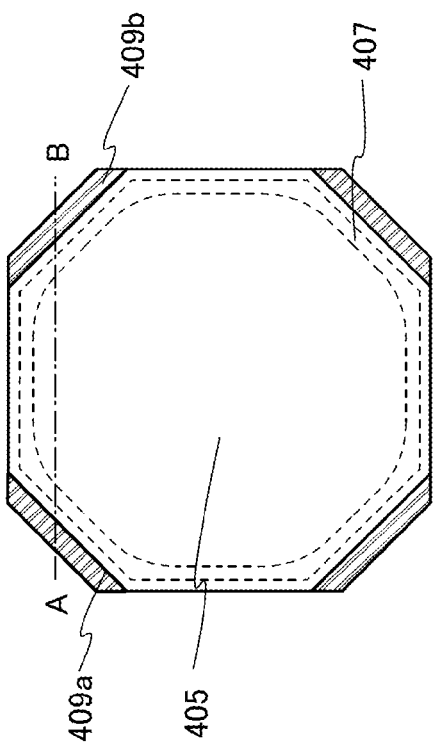
FIGS. 2A and 2B illustrate an example of a light-emitting device of one embodiment of the present invention.
Figure 2B:
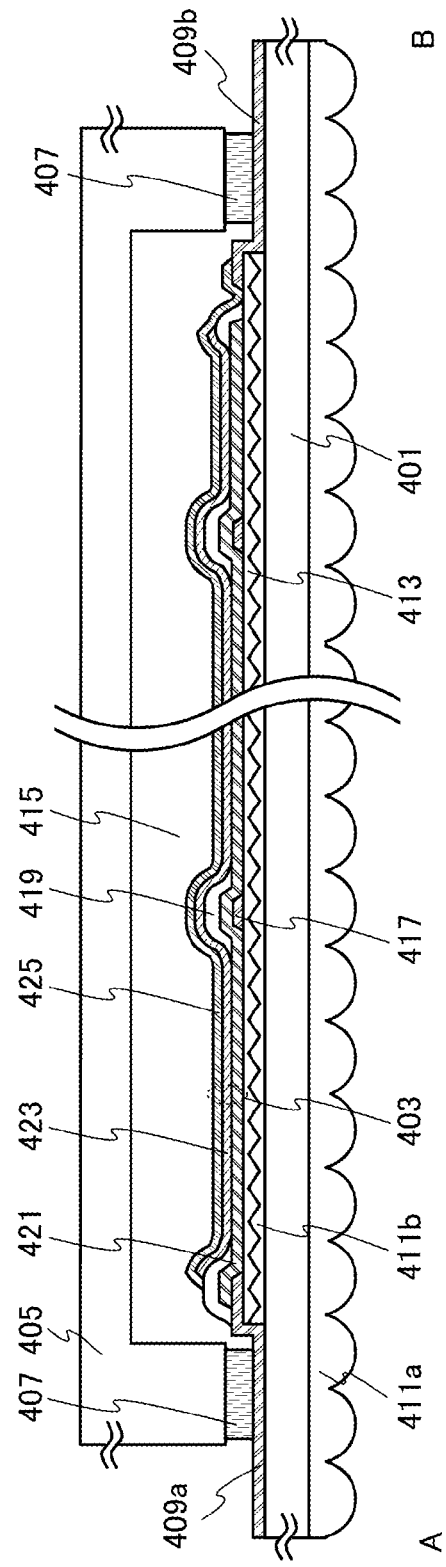

FIG. 2A is a plan view of a light-emitting device of one embodiment of the present invention, and FIG. 2B is a cross-sectional view taken along dashed-dotted line A-B in FIG. 2A.

In the light-emitting device of this embodiment, a light-emitting element 403 is provided in a space 415 surrounded by a support substrate 401, a sealing substrate 405, and a sealing material 407. The light-emitting element 403 is an organic EL element having a bottom-emission structure; specifically, a first electrode 421 which transmits visible light is provided over the support substrate 401, an EL layer 423 is provided over the first electrode 421, and a second electrode 425 which reflects visible light is provided over the EL layer 423. The EL layer 423 contains the compound of one embodiment of the present invention which is described in Embodiment 1.

A first terminal 409a is electrically connected to an auxiliary wiring 417 and the first electrode 421. An insulating layer 419 is provided over the first electrode 421 in a region which overlaps with the auxiliary wiring 417. The first terminal 409a is electrically insulated from the second electrode 425 by the insulating layer 419. A second terminal 409b is electrically connected to the second electrode 425. Note that although the first electrode 421 is formed over the auxiliary wiring 417 in this embodiment, the auxiliary wiring 417 may be formed over the first electrode 421.

A light extraction structure 411a is preferably provided at the interface between the support substrate 401 and the atmosphere. When provided at the interface between the support substrate 401 and the atmosphere, the light extraction structure 411a can reduce light that cannot be extracted to the atmosphere because of total reflection, resulting in an increase in the light extraction efficiency of the light-emitting device.

In addition, a light extraction structure 411b is preferably provided at the interface between the light-emitting element 403 and the support substrate 401. When the light extraction structure 411b has unevenness, a planarization layer 413 is preferably provided between the light extraction structure 411b and the first electrode 421. Accordingly, the first electrode 421 can be a flat film, and generation of leakage current in the EL layer 423 due to the unevenness of the first electrode 421 can be prevented. Furthermore, because of the light extraction structure 411b at the interface between the planarization layer 413 and the support substrate 401, light that cannot be extracted to the atmosphere because of total reflection can be reduced, so that the light extraction efficiency of the light-emitting device can be increased.

As a material of the light extraction structure 411a and the light extraction structure 411b, a resin can be used, for example. Alternatively, for the light extraction structure 411a and the light extraction structure 411b, a hemispherical lens, a micro lens array, a film provided with an uneven structure, a light diffusing film, or the like can be used. For example, the light extraction structure 411a and the light extraction structure 411b can be formed by attaching the lens or film to the support substrate 401 with an adhesive or the like which has substantially the same refractive index as the support substrate 401 or the lens or film.

The surface of the planarization layer 413 which is in contact with the first electrode 421 is flatter than the surface of the planarization layer 413 which is in contact with the light extraction structure 411b. As a material of the planarization layer 413, glass, liquid, a resin, or the like having a light-transmitting property and a high refractive index can be used.

FIG. 3A is a plan view of a light-emitting device of one embodiment of the present invention, FIG. 3B is a cross-sectional view taken along dashed-dotted line C-D in FIG. 3A, and FIG. 3C is a cross-sectional view illustrating a modified example of the light-emitting portion.

An active matrix light-emitting device of this embodiment includes, over a support substrate 501, a light-emitting portion 551 (the cross section of which is illustrated in FIG. 3B and FIG. 3C as a light-emitting portion 551a and a light-emitting portion 551b, respectively), a driver circuit portion 552 (gate side driver circuit portion), a driver circuit portion 553 (source side driver circuit portion), and a sealing material 507. The light-emitting portion 551 and the driver circuit portions 552 and 553 are sealed in a space 515 surrounded by the support substrate 501, a sealing substrate 505, and the sealing material 507.

Any of a separate coloring method, a color filter method, and a color conversion method can be applied to the light-emitting device of one embodiment of the present invention. The light-emitting portion 551a fabricated by a color filter method is illustrated in FIG. 3B, and the light-emitting portion 551b fabricated by a separate coloring method is illustrated in FIG. 3C.

Each of the light-emitting portion 551a and the light-emitting portion 551b includes a plurality of light-emitting units each including a switching transistor 541a, a current control transistor 541b, and a second electrode 525 electrically connected to a wiring (a source electrode or a drain electrode) of the current control transistor 541b.

A light-emitting element 503 included in the light-emitting portion 551a has a bottom-emission structure and includes a first electrode 521 which transmits visible light, an EL layer 523, and the second electrode 525. Furthermore, a partition 519 is formed so as to cover an end portion of the first electrode 521.

A light-emitting element 504 included in the light-emitting portion 551b has a top-emission structure and includes a first electrode 561, an EL layer 563, and the second electrode 565 which transmits visible light. Furthermore, the partition 519 is formed so as to cover an end portion of the first electrode 561. In the EL layer 563, at least layers (e.g., light-emitting layers) which contain different materials depending on the light-emitting element are colored separately.

Over the support substrate 501, a lead wiring 517 for connecting an external input terminal through which a signal (e.g., a video signal, a clock signal, a start signal, or a reset signal) or a potential from the outside is transmitted to the driver circuit portion 552 or 553 is provided. Here, an example is described in which a flexible printed circuit (FPC) 509 is provided as the external input terminal.

The driver circuit portions 552 and 553 include a plurality of transistors. FIG. 3B illustrates two of the transistors in the driver circuit portion 552 (transistors 542 and 543).

To prevent an increase in the number of manufacturing steps, the lead wiring 517 is preferably formed using the same material and the same step(s) as those of the electrode or the wiring in the light-emitting portion or the driver circuit portion. Described in this embodiment is an example in which the lead wiring 517 is formed using the same material and the same step(s) as those of the source electrodes and the drain electrodes of the transistors included in the light-emitting portion 551 and the driver circuit portion 552.

In FIG. 3B, the sealing material 507 is in contact with a first insulating layer 511 over the lead wiring 517. The adhesion of the sealing material 507 to metal is low in some cases. Therefore, the sealing material 507 is preferably in contact with an inorganic insulating film over the lead wiring 517. Such a structure enables a light-emitting device to have high sealing capability, high adhesion, and high reliability. As examples of the inorganic insulating film, oxide films of metals and semiconductors, nitride films of metals and semiconductors, and oxynitride films of metals and semiconductors are given, and specifically, a silicon oxide film, a silicon nitride film, a silicon oxynitride film, a silicon nitride oxide film, an aluminum oxide film, a titanium oxide film, and the like can be given.

The first insulating layer 511 has an effect of preventing diffusion of impurities into a semiconductor included in the transistor. As the second insulating layer 513, an insulating film having a planarization function is preferably selected in order to reduce surface unevenness due to the transistor.

There is no particular limitation on the structure and materials of the transistor used in the light-emitting device of one embodiment of the present invention. A top-gate transistor may be used, or a bottom-gate transistor such as an inverted staggered transistor may be used. The transistor may be a channel-etched transistor or a channel-protective transistor. An n-channel transistor may be used and a p-channel transistor may also be used.

A semiconductor layer can be formed using silicon, an oxide semiconductor, or an organic semiconductor. It is preferable that the transistor be formed using an oxide semiconductor which is an In—Ga—Zn-based metal oxide for a semiconductor layer so as to have low off-state current because an off-state leakage current of the light-emitting element can be reduced.

The sealing substrate 505 illustrated in FIG. 3B is provided with a color filter 533 as a coloring layer at a position overlapping with the light-emitting element 503 (a light-emitting region thereof), and is also provided with a black matrix 531 at a position overlapping with the partition 519. Furthermore, an overcoat layer 535 is provided so as to cover the color filter 533 and the black matrix 531. The sealing substrate 505 illustrated in FIG. 3C is provided with a desiccant 506.

This embodiment can be combined with any other embodiment as appropriate.

(Embodiment 4)

In this embodiment, examples of electronic devices and lighting devices of embodiments of the present invention will be described with reference to FIGS. 4A to 4E and FIGS. 6A and 6B.

Electronic devices of this embodiment each include the light-emitting device of one embodiment of the present invention in a display portion. Lighting devices of this embodiment each include the light-emitting device of one embodiment of the present invention in a light-emitting portion (a lighting portion). Highly reliable electronic devices and highly reliable lighting devices can be provided by adopting the light-emitting device of one embodiment of the present invention.

Note that one embodiment of the present invention is not limited to these examples, and the light-emitting device of one embodiment of the present invention is not necessarily included.

Examples of electronic devices to which the light-emitting device is applied are television devices (also referred to as TV or television receivers), monitors for computers and the like, cameras such as digital cameras and digital video cameras, digital photo frames, cellular phones (also referred to as mobile phones or portable telephone devices), portable game machines, portable information terminals, audio playback devices, large game machines such as pin-ball machines, and the like. Specific examples of these electronic devices and lighting devices are illustrated in FIGS. 4A to 4E and FIGS. 6A and 6B.

The electronic device and lighting device of embodiments of the present invention may have flexibility. The electronic device and lighting device can be incorporated along a curved inside/outside wall surface of a house or a building or a curved interior/exterior surface of a car.

Figure 4A:
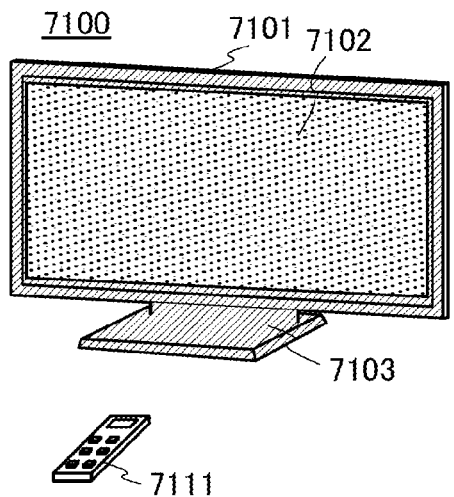
FIGS. 4A to 4E illustrate examples of an electronic device.

FIG. 4A illustrates an example of a television device. In a television device 7100, a display portion 7102 is incorporated in a housing 7101. The display portion 7102 is capable of displaying images. The light-emitting device of one embodiment of the present invention can be used for the display portion 7102. In addition, here, the housing 7101 is supported by a stand 7103.

The television device 7100 can be operated with an operation switch provided in the housing 7101 or a separate remote controller 7111. With operation keys of the remote controller 7111, channels and volume can be controlled and images displayed on the display portion 7102 can be controlled. The remote controller 7111 may be provided with a display portion for displaying data output from the remote controller 7111.

Note that the television device 7100 is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) data communication can be performed.

Figure 4B:
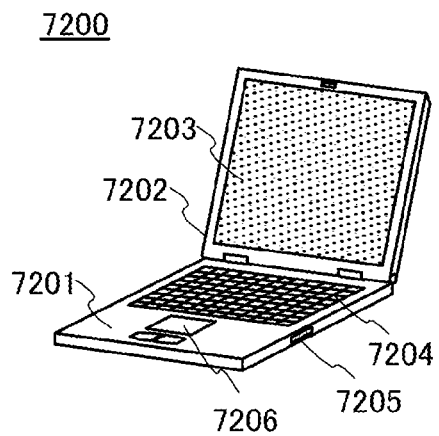

FIG. 4B illustrates an example of a computer. A computer 7200 includes a main body 7201, a housing 7202, a display portion 7203, a keyboard 7204, an external connection port 7205, a pointing device 7206, and the like. Note that this computer is manufactured by using the light-emitting device of one embodiment of the present invention for the display portion 7203.

Figure 4C:
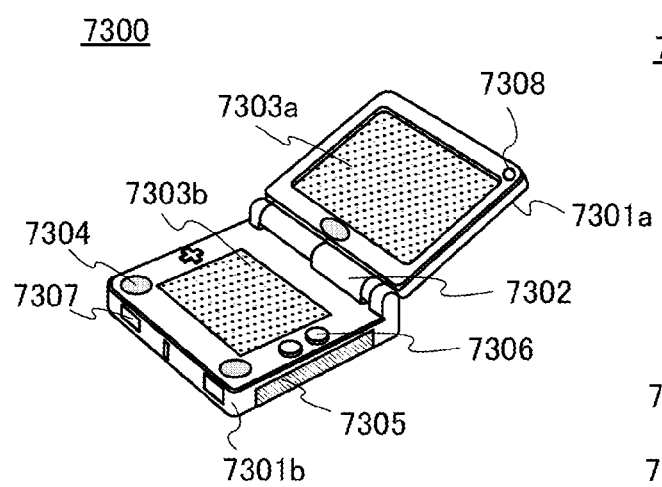

FIG. 4C illustrates an example of a portable game machine. A portable game machine 7300 has two housings, a housing 7301a and a housing 7301b, which are connected with a joint portion 7302 so that the portable game machine can be opened or closed. The housing 7301a incorporates a display portion 7303a, and the housing 7301b incorporates a display portion 7303b. In addition, the portable game machine illustrated in FIG. 4C includes a speaker portion 7304, a recording medium insertion portion 7305, an operation key 7306, a connection terminal 7307, a sensor 7308 (a sensor having a function of measuring or sensing force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), an LED lamp, a microphone, and the like. It is needless to say that the structure of the portable game machine is not limited to the above structure as long as the light-emitting device of one embodiment of the present invention is used for at least either the display portion 7303a or the display portion 7303b, or both, and may include other accessories as appropriate. The portable game machine illustrated in FIG. 4C has a function of reading out a program or data stored in a recoding medium to display it on the display portion, and a function of sharing data with another portable game machine by wireless communication. Note that functions of the portable game machine illustrated in FIG. 4C are not limited to them, and the portable game machine can have various functions.

Figure 4D:
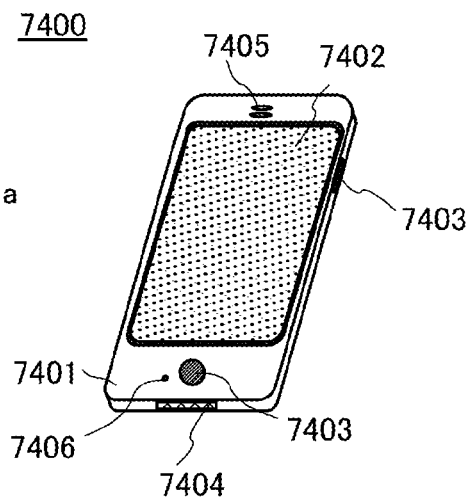

FIG. 4D illustrates an example of a cellular phone. A cellular phone 7400 is provided with a display portion 7402 incorporated in a housing 7401, an operation button 7403, an external connection port 7404, a speaker 7405, a microphone 7406, and the like. Note that the cellular phone 7400 is manufactured by using the light-emitting device of one embodiment of the present invention for the display portion 7402.

When the display portion 7402 of the cellular phone 7400 illustrated in FIG. 4D is touched with a finger or the like, data can be input into the cellular phone. Furthermore, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting data such as characters. The third mode is a display-and-input mode in which two modes of the display mode and the input mode are combined.

For example, in the case of making a call or creating e-mail, a text input mode mainly for inputting text is selected for the display portion 7402 so that text displayed on the screen can be input.

When a sensing device including a sensor such as a gyroscope sensor or an acceleration sensor for detecting inclination is provided inside the cellular phone 7400, display on the screen of the display portion 7402 can be automatically changed in direction by determining the orientation of the cellular phone 7400 (whether the cellular phone 7400 is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, a signal detected by an optical sensor in the display portion 7402 can be detected, whereby the screen mode may be controlled so as to be switched from the input mode to the display mode in the case where input by touching the display portion 7402 is not performed for a specified period.

The display portion 7402 may function as an image sensor. For example, an image of a palm print, a fingerprint, or the like is taken by touch on the display portion 7402 with the palm or the finger, whereby personal authentication can be performed. Furthermore, when a backlight or a sensing light source which emits near-infrared light is provided in the display portion, an image of a finger vein, a palm vein, or the like can be taken.

Figure 4E:
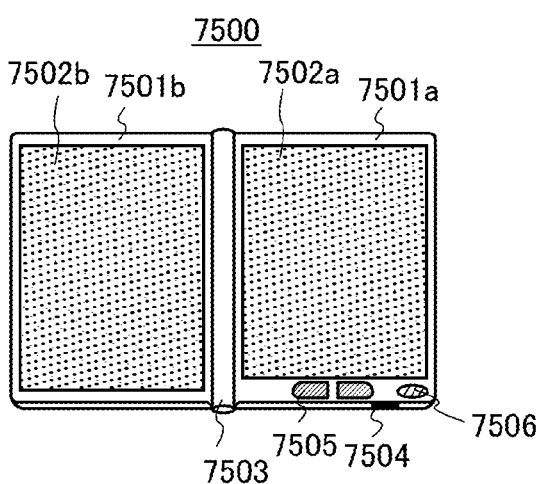

FIG. 4E illustrates an example of a foldable tablet terminal (in an open state). A tablet terminal 7500 includes a housing 7501a, a housing 7501b, a display portion 7502a, and a display portion 7502b. The housing 7501a and the housing 7501b are connected by a hinge 7503 and can be opened and closed using the hinge 7503 as an axis. The housing 7501a includes a power switch 7504, operation keys 7505, a speaker 7506, and the like. Note that the tablet terminal 7500 is manufactured by using the light-emitting device of one embodiment of the present invention for either the display portion 7502a or the display portion 7502b, or both.

Part of the display portion 7502a or the display portion 7502b can be used as a touch panel region, where data can be input by touching displayed operation keys. For example, a keyboard can be displayed on the entire region of the display portion 7502a so that the display portion 7502a is used as a touch panel, and the display portion 7502b can be used as a display screen.

The electronic device of one embodiment of the present invention may include an input/output device (also referred to as a touch panel) and a secondary battery. It is preferable that the secondary battery is capable of being charged by contactless power transmission. The input/output device includes a display portion and an input portion. For the display portion, the light-emitting device of one embodiment of the present invention can be used. For the input portion, an input device including a sensor element or the like (also referred to as a touch sensor) can be used.

As examples of the secondary battery, a lithium ion secondary battery such as a lithium polymer battery (lithium ion polymer battery) using a gel electrolyte, a nickel-hydride battery, a nickel-cadmium battery, an organic radical battery, a lead-acid battery, an air secondary battery, a nickel-zinc battery, and a silver-zinc battery can be given.

The electronic device of one embodiment of the present invention may include a touch panel and an antenna. When a signal is received by the antenna, the electronic device can display an image, data, or the like on a display portion. When the electronic device includes a secondary battery, the antenna may be used for contactless power transmission.

Figure 5A:
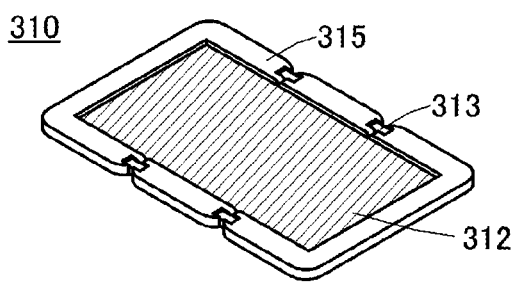
FIGS. 5A to 5I illustrate examples of an electronic device.
Figure 5B:
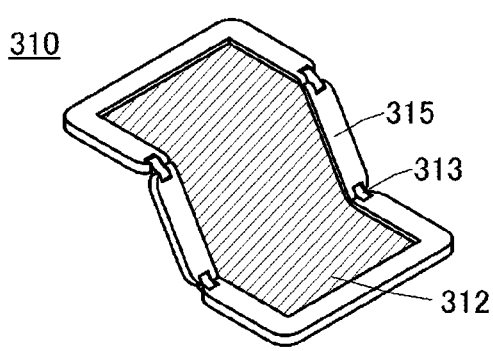
Figure 5C:
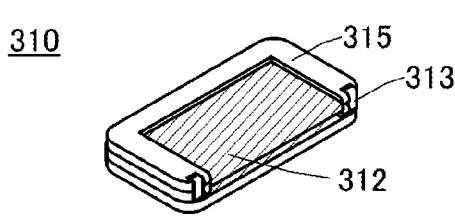

FIGS. 5A to 5C illustrate a foldable portable information terminal 310. FIG. 5A illustrates the portable information terminal 310 that is opened. FIG. 5B illustrates the portable information terminal 310 that is being opened or being folded. FIG. 5C illustrates the portable information terminal 310 that is folded. The portable information terminal 310 is highly portable when folded. When the portable information terminal 310 is opened, a seamless large display region is highly browsable.

A display panel 312 is supported by three housings 315 joined together by hinges 313. By folding the portable information terminal 310 at a connection portion between two housings 315 with the hinges 313, the portable information terminal 310 can be reversibly changed in shape from an opened state to a folded state. The light-emitting device (or display device) of one embodiment of the present invention can be used for the display panel 312. For example, a display device that can be bent with a radius of curvature of greater than or equal to 1 mm and less than or equal to 150 mm can be used.

Figure 5D:
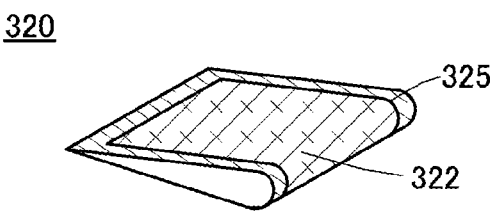
Figure 5E:
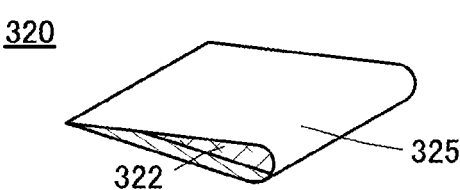

FIGS. 5D and 5E illustrate a foldable portable information terminal 320. FIG. 5D illustrates the portable information terminal 320 that is folded so that a display portion 322 is on the outside. FIG. 5E illustrates the portable information terminal 320 that is folded so that the display portion 322 is on the inside. When the portable information terminal 320 is not used, the portable information terminal 320 is folded so that a non-display portion 325 faces the outside, whereby the display portion 322 can be prevented from being contaminated or damaged. The light-emitting device (or display device) of one embodiment of the present invention can be used for the display portion 322.

Figure 5F:
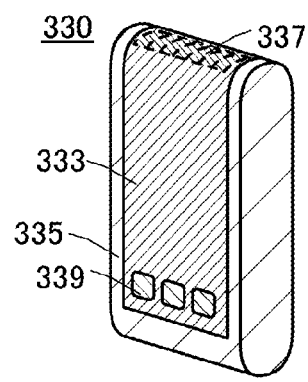
Figure 5G:
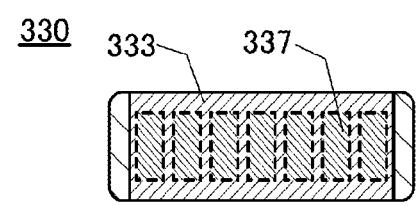
Figure 5H:
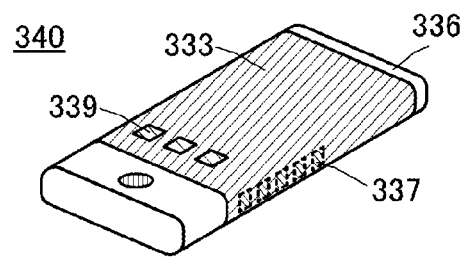

FIG. 5F is a perspective view illustrating an external shape of the portable information terminal 330. FIG. 5G is a top view of the portable information terminal 330. FIG. 5H is a perspective view illustrating an external shape of a portable information terminal 340.

The portable information terminals 330 and 340 each function as, for example, one or more of a telephone set, a notebook, and an information browsing system. Specifically, the portable information terminals 330 and 340 each can be used as a smartphone.

The portable information terminals 330 and 340 can display characters and image data on its plurality of surfaces. For example, three operation buttons 339 can be displayed on one surface (FIGS. 5F and 5H). In addition, data 337 indicated by dashed rectangles can be displayed on another surface (FIGS. 5G and 5H). Examples of the data 337 include notification from a social networking service (SNS), display indicating reception of e-mail or an incoming call, the title of e-mail or the like, the sender of e-mail or the like, the date, the time, remaining battery, and the reception strength of an antenna. Alternatively, the operation buttons 339, an icon, or the like may be displayed in place of the data 337. Although FIGS. 5F and 5G illustrate an example in which the data 337 is displayed at the top, one embodiment of the present invention is not limited thereto. The data may be displayed, for example, on the side as in the portable information terminal 340 illustrated in FIG. 5H.

The light-emitting device (or display device) of one embodiment of the present invention can be used for a display portion 333 mounted in each of a housing 335 of the portable information terminal 330 and a housing 336 of the portable information terminal 340.

Figure 5I:
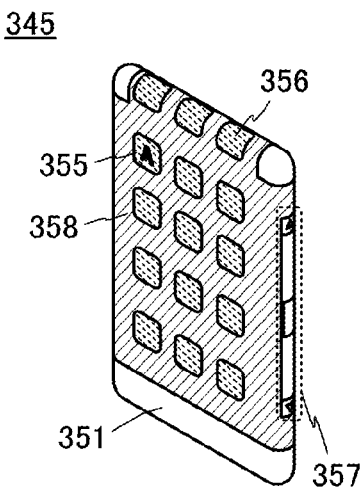

As in a portable information terminal 345 illustrated in FIG. 5I, data may be displayed on three or more surfaces. Here, data 355, data 356, and data 357 are displayed on different surfaces. The light-emitting device (or display device) of one embodiment of the present invention can be used for a display portion 358 included in a housing 351 of the portable information terminal 345.

Figure 6A:
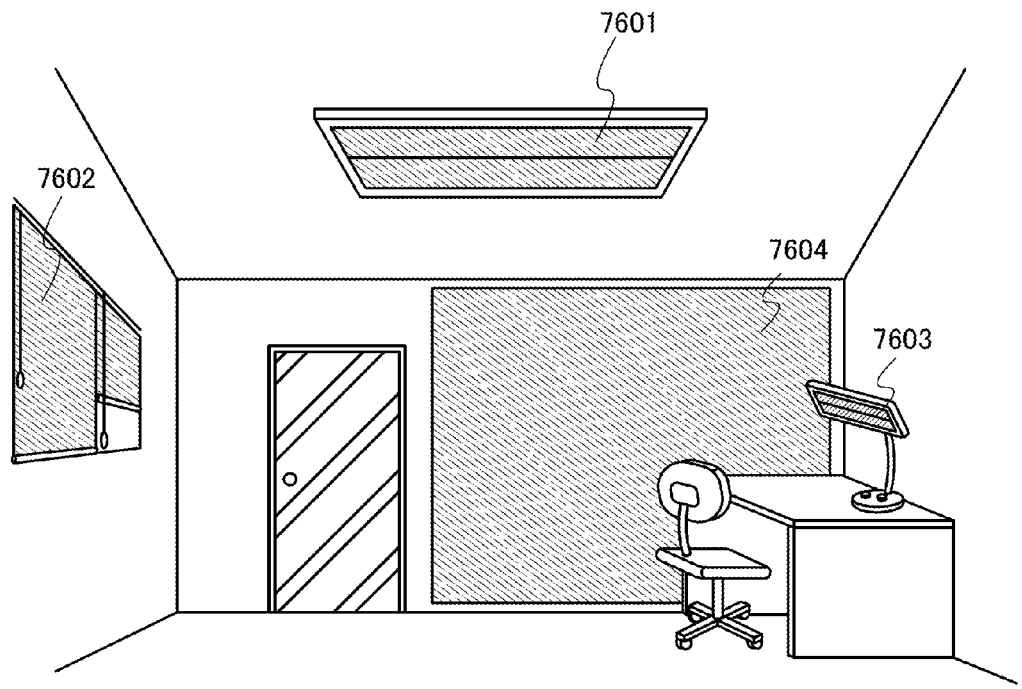
FIGS. 6A and 6B illustrate examples of a lighting device.

An indoor lighting device 7601, a roll-type lighting device 7602, a desk lamp 7603, and a planar lighting device 7604 illustrated in FIG. 6A are each an example of a lighting device which includes the light-emitting device of one embodiment of the present invention. Since the light-emitting device of one embodiment of the present invention can have a larger area, it can be used as a large-area lighting device. Furthermore, since the light-emitting device is thin, the light-emitting device can be mounted on a wall.

Figure 6B:
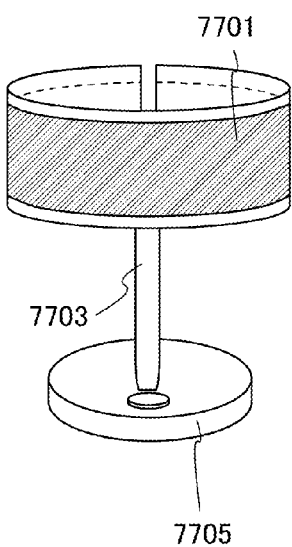

A desk lamp illustrated in FIG. 6B includes a lighting portion 7701, a support 7703, a support base 7705, and the like. The light-emitting device of one embodiment of the present invention is used for the lighting portion 7701. In one embodiment of the present invention, a lighting device whose light-emitting portion has a curved surface or a lighting device including a flexible lighting portion can be achieved. Such use of a flexible light-emitting device for a lighting device enables a place having a curved surface, such as the ceiling or dashboard of a motor vehicle, to be provided with the lighting device, as well as increases the degree of freedom in design of the lighting device. The lighting device of one embodiment of the present invention may include a housing or a cover.

This embodiment can be combined with any other embodiment as appropriate.

EXAMPLE 1

Synthesis Example 1

This example describes a method for synthesizing 2-[3'-(benzo[b]naphtho[2,3-d]furan-8-yl)biphenyl-3-yl]dibenzo

[f,h]quinoxaline (abbreviation: 2mBnf(II)BPDBq), which is a compound of one embodiment of the present invention represented by Structural Formula (101). This example also describes a method for synthesizing 8-chlorobenzo[b]naphtho[2,3-d]furan, which is a compound of one embodiment of the present invention represented by Structural Formula (201).

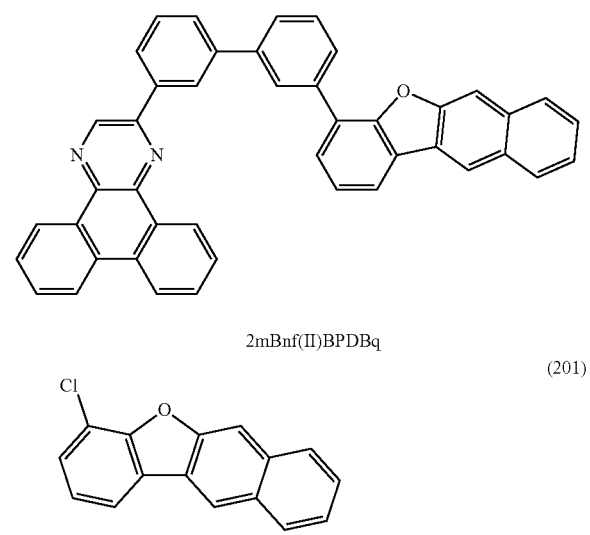

2mBnf(II)BPDBq (101)

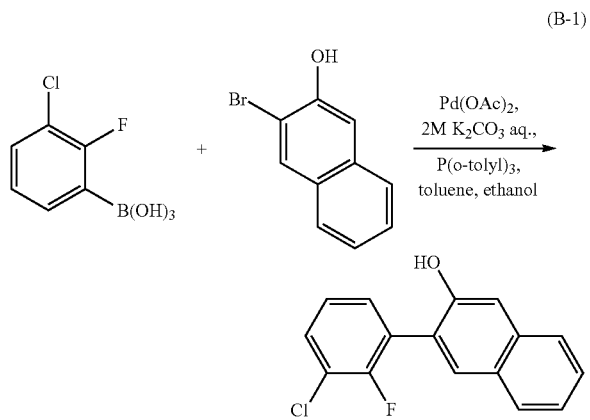

(201)

<Step 1: Synthesis of 3-(3-Chloro-2-fluorophenyl)-2-naphthol>

A synthesis scheme of Step 1 is shown in (B-1).

In a 1000 mL three-neck flask were put 16 g (70 mmol) of 3-bromo-2-naphthol, 12 g (70 mmol) of 3-chloro-2-fluorobenzeneboronic acid, and 1.1 g (3.5 mol) of tri(ortho-tolyl)phosphine, and the air in the flask was replaced with nitrogen. To this mixture, 300 mL of toluene, 60 mL of ethanol, and 90 mL of an aqueous solution of potassium carbonate (2.0 mol/L) were added. The mixture was degassed by being stirred while the pressure in the flask was reduced; then, the air in the flask was replaced with nitrogen. To this mixture was added 0.16 g (0.70 mmol) of palladium (II) acetate, and the resulting mixture was stirred at 80° C. under a nitrogen stream for 3 hours. After the stirring, the organic layer of the mixture was washed with water and the aqueous layer was then subjected to extraction with ethyl acetate. The solution of the extract combined with the organic layer was washed with saturated brine, and the organic layer was dried with magnesium sulfate. The resulting mixture was gravity-filtered, and the resulting filtrate was concentrated to give 23 g of a brown liquid that contains a target substance as a main component.

<Step 2: Synthesis of 8-Chlorobenzo[b]naphtho[2,3-d]furan>

A synthesis scheme of Step 2 is shown in (B-2).

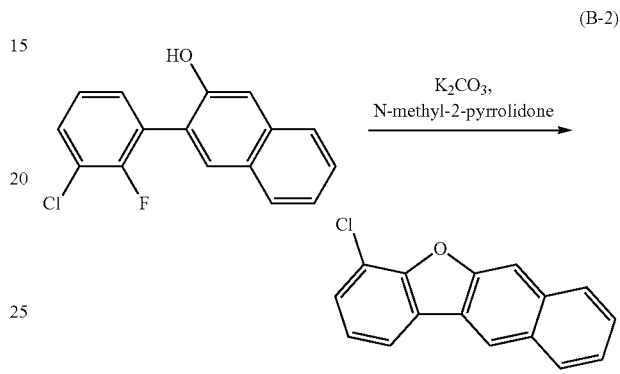

Into a 500 mL recovery flask were put 23 g of the brown liquid obtained in Step 1, 300 mL of N-methyl-2-pyrrolidone, and 27 g (0.20 mol) of potassium carbonate, and the mixture was stirred at 150° C. in the air for 7 hours. After the stirring, approximately 50 mL of water and approximately 50 mL of hydrochloric acid (1.0 mol/L) were added to the resulting mixture. To the resulting solution was added approximately 100 mL of ethyl acetate; then, the aqueous layer was subjected to extraction with ethyl acetate three times. The solution of the extract combined with the organic layer was washed with a saturated aqueous solution of sodium hydrogen carbonate and saturated brine, and magnesium sulfate was then added. The mixture was gravity-filtered, and the resulting filtrate was concentrated to give 5.4 g of a pale brown solid of a target substance in a yield of 23% (this yield is the total of Step 1 and Step 2).

$^1$H NMR data of the pale brown solid are as follows:

$^1$H NMR (CDCl$_3$, 500 MHz): δ=7.32 (t, J=7.5 Hz, 1H), 7.49-7.57 (m, 3H), 7.96 (dd, J1=8.25 Hz, 12=1.5 Hz, 1H), 8.00 (d, J=9.0 Hz, 1H), 8.01 (s, 1H), 8.04 (d, J=9.0 Hz, 1H), 8.42 (s, 1H).

Figure 7A:
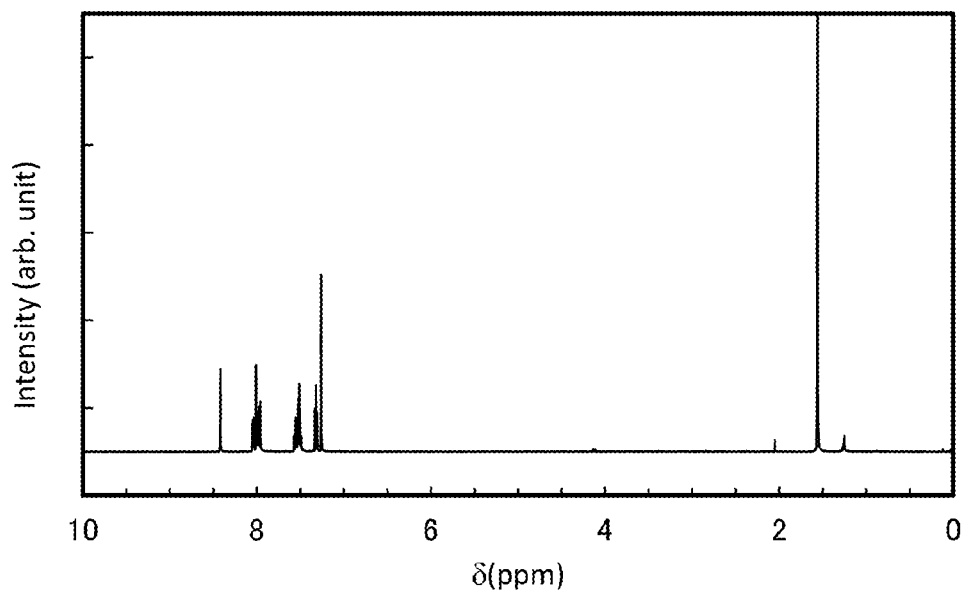
FIGS. 7A and 7B show $^1$H NMR charts of 8-chlorobenzo[b]naphtho[2,3-d]furan.
Figure 7B:
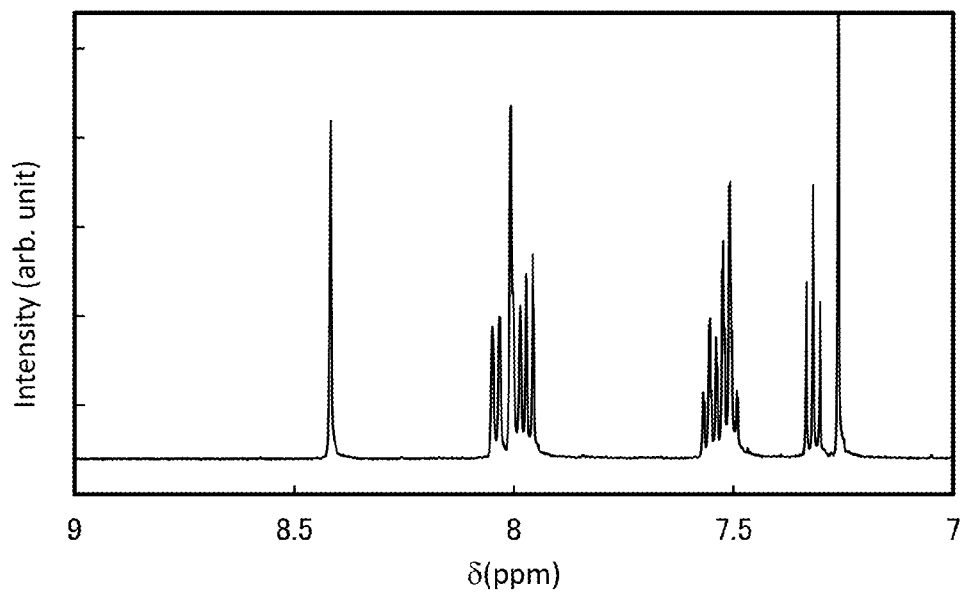

In addition, FIGS. 7A and 7B show $^1$H NMR charts. Note that FIG. 7B is a chart showing an enlarged part of FIG. 7A in the range of 7.00 ppm to 9.00 ppm.

<Step 3: Synthesis of 2-(Benzo[b]naphtho[2,3-d]furan-8-yl)-4,4,5,5-tetramethyl-1,3,2-dioxaborolane>

A synthesis scheme of Step 3 is shown in (B-3).

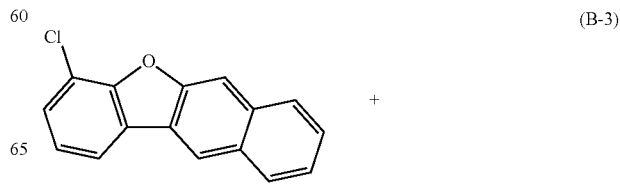

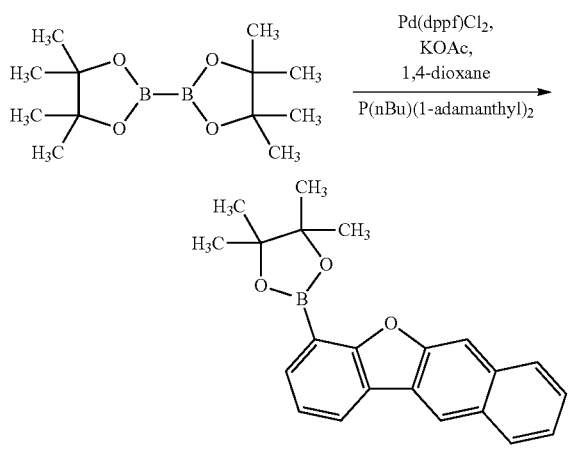

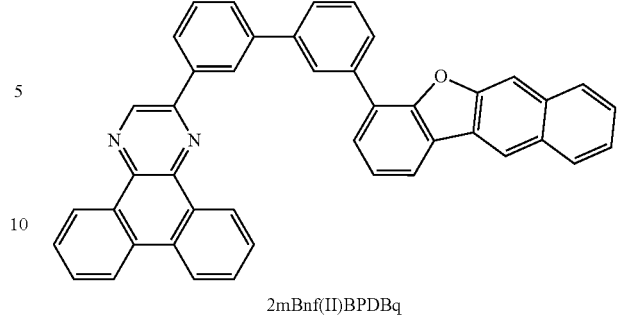

2mBnf(II)BPDBq

In a 200 mL three-neck flask were put 1.1 g (4.3 mmol) of 8-chlorobenzo[b]naphtho[2,3-d]furan, 1.1 g (4.3 mmol) of bis(pinacolato)diboron, 0.79 g (8.0 mmol) of potassium acetate, and 179 mg of (0.50 mmol) of di(1-adamantyl)-n-butylphosphine, and the air in the flask was replaced with nitrogen. To this mixture, 25 mL of 1,4-dioxane was added. The mixture was degassed by being stirred while the pressure in the flask was reduced; then, the air in the flask was replaced with nitrogen. To this mixture was added 81 mg (0.11 mmol) of [1,1'-bis(diphenylphosphino)ferrocene]palladium(II) dichloride dichloromethane adduct, and the mixture was refluxed at 180° C. under a nitrogen stream for 5 hours. After the reflux, a thin-layer silica gel chromatography (a developing solvent of hexane:ethyl acetate=10:1) was performed to check on the progress of the reaction. Because no spot derived from the raw materials was observed, the next reaction was then performed.

<Step 4: Synthesis of 2mBnf(II)BPDBq>

A synthesis scheme of Step 4 is shown in (B-4).

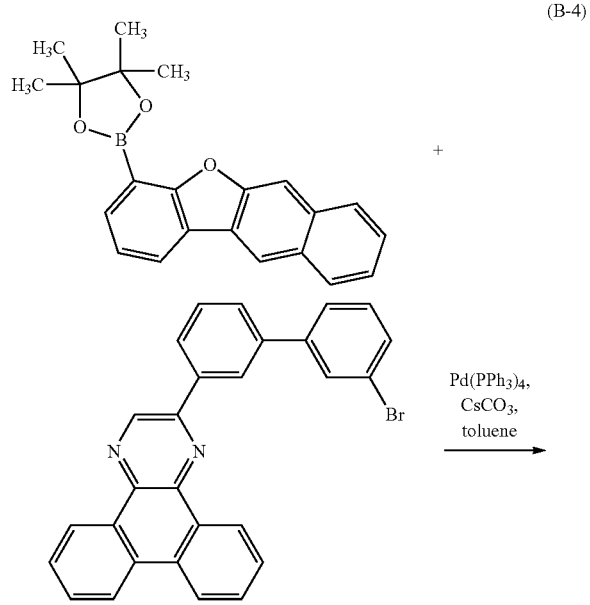

After Step 3, the following reaction was carried out in the same container without work-up (posttreatment). To the reaction mixture obtained in Step 3 and containing 2-(benzo[b]naphtho[2,3-d]furan-8-yl)-4,4,5,5-tetramethyl-1,3,2-dioxaborolane, 1.9 g (4.3 mmol) of 2-(3'-bromobiphenyl-3-yl)dibenzo[f,h]quinoxaline and 3.3 g (10 mmol) of cesium carbonate were added. To this mixture, 0.12 mg (0.10 mol) of tetrakis(triphenylphosphine)palladium(0) was added, and the mixture was stirred at 150° C. under a nitrogen stream for 5.5 hours. To the resulting mixture, approximately 100 mL of toluene was added, and this mixture was refluxed. After the reflux, a solid remaining unsolved was collected by suction-filtration, and the resulting solid was washed with water and ethanol in this order to give 1.4 g of a pale brown solid in a crude yield of 55%.

By a train sublimation method, 1.4 g of the obtained pale brown solid was purified. In the sublimation purification, the solid was heated at 330° C. for 15 hours under a pressure of 2.5 Pa with a flow rate of argon gas of 15 mL/min. After the sublimation purification, 0.96 g of a pale yellow solid was obtained at a collection rate of 69%.

This compound was identified as 2mBnf(II)BPDBq, which was the target substance, by nuclear magnetic resonance (NMR) spectroscopy.

$^1$H NMR data of the brown solid are as follows: $^1$H NMR (tetrschloroethane-$d_2$, 500 MHz): δ=7.49-7.55 (m, 3H), 7.73-7.87 (m, 8H), 7.90-7.94 (m, 2H), 8.00 (s, 1H), 8.04 (d, J=7.5 Hz, 1H), 8.07 (d, J=7.5 Hz, 1H), 8.12 (d, J=8.5 Hz, 1H), 8.37-8.39 (m, 2H), 8.48 (s, 1H), 8.67 (d, J=8.0 Hz, 2H), 8.74 (s, 1H), 9.31 (d, J=8.0 Hz, 1H), 9.47 (d, J=8.0 Hz, 1H), 9.53 (s, 1H).

Figure 8A:
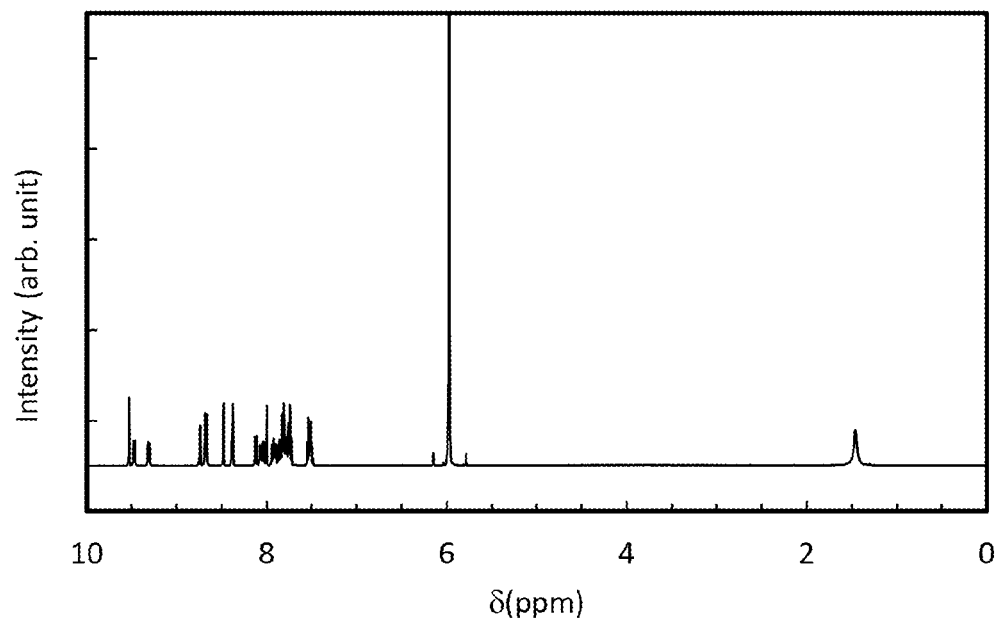
FIGS. 8A and 8B show $^1$H NMR charts of 2-[3'-(benzo[b]naphtho[2,3-d]furan-8-yl)biphenyl-3-yl]dibenzo[f,h]quinoxaline (abbreviation: 2mBnf(II)BPDBq).
Figure 8B:
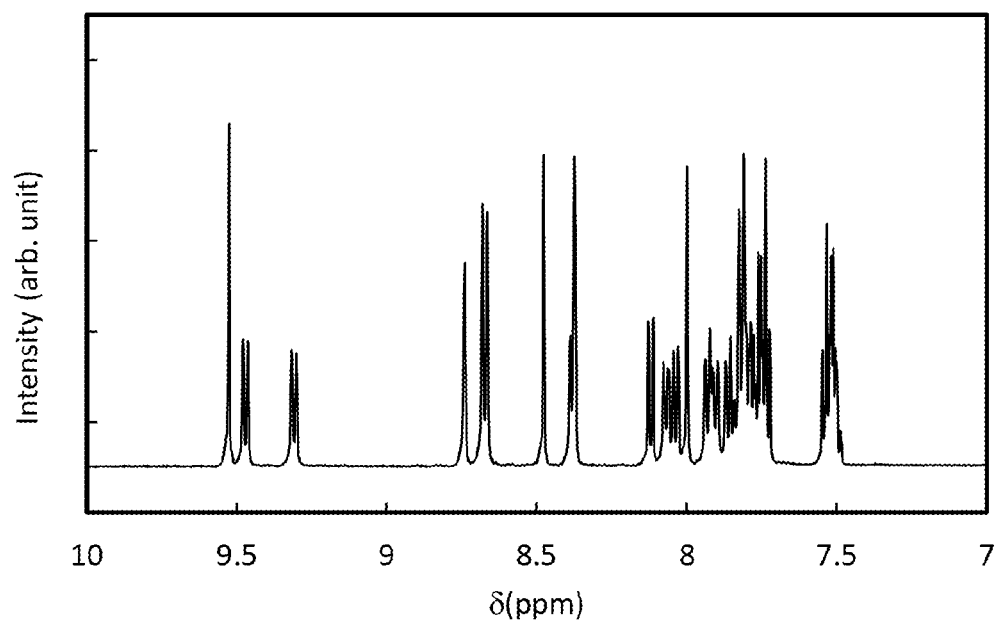

In addition, FIGS. 8A and 8B show $^1$H NMR charts. Note that FIG. 8B is a chart showing an enlarged part of FIG. 8A in the range of 7.00 ppm to 10.0 ppm.

Figure 9A:
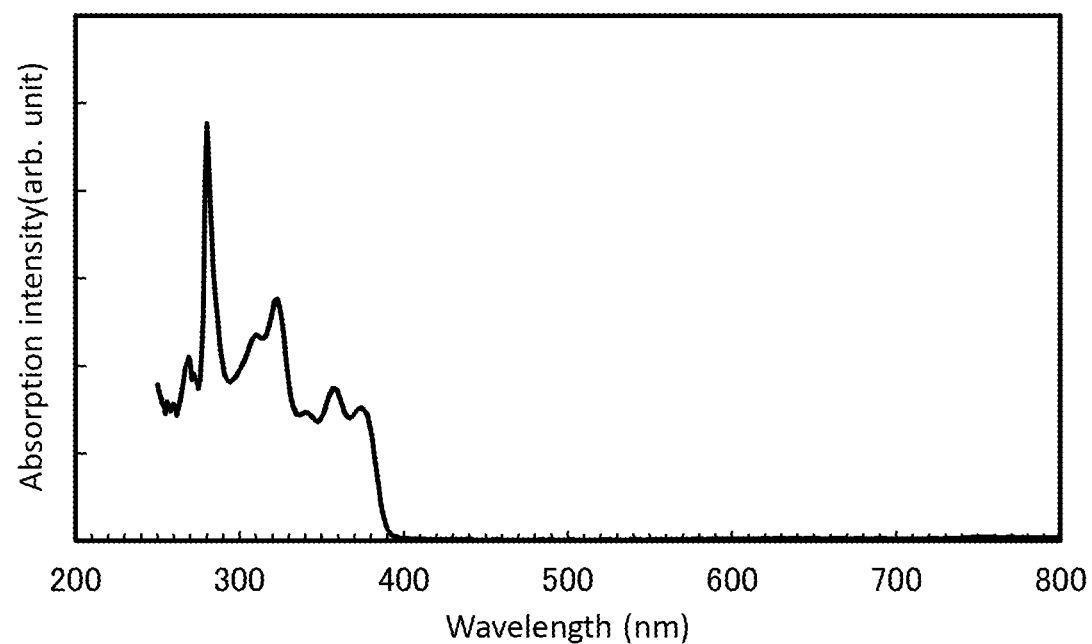
FIGS. 9A and 9B show an absorption spectrum and an emission spectrum of a toluene solution of 2mBnf(II)BPDBq.
Figure 9B:
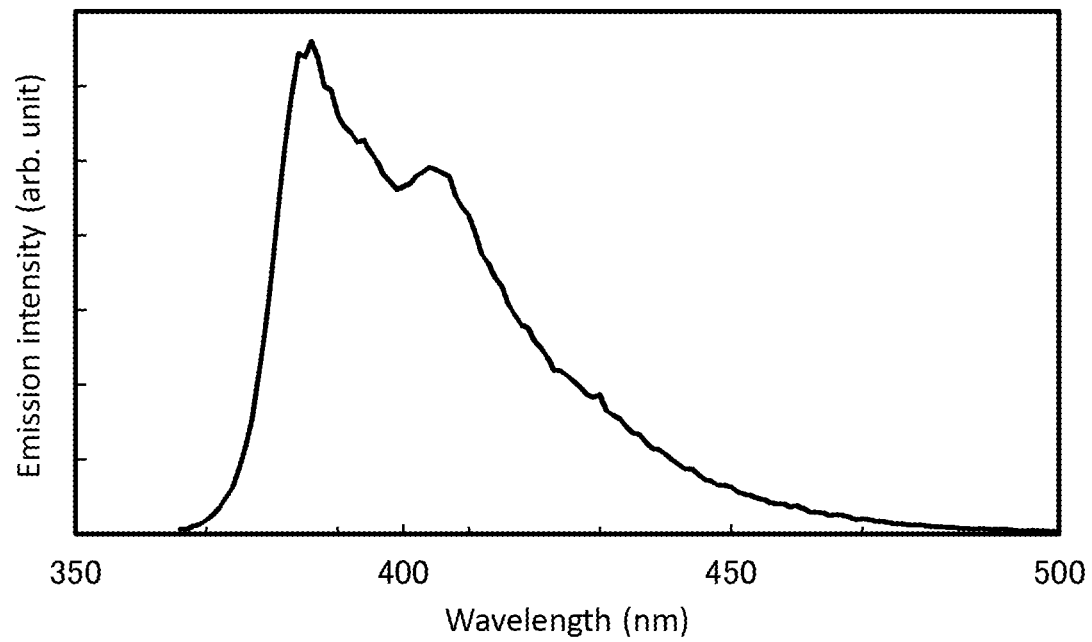
Figure 10A:
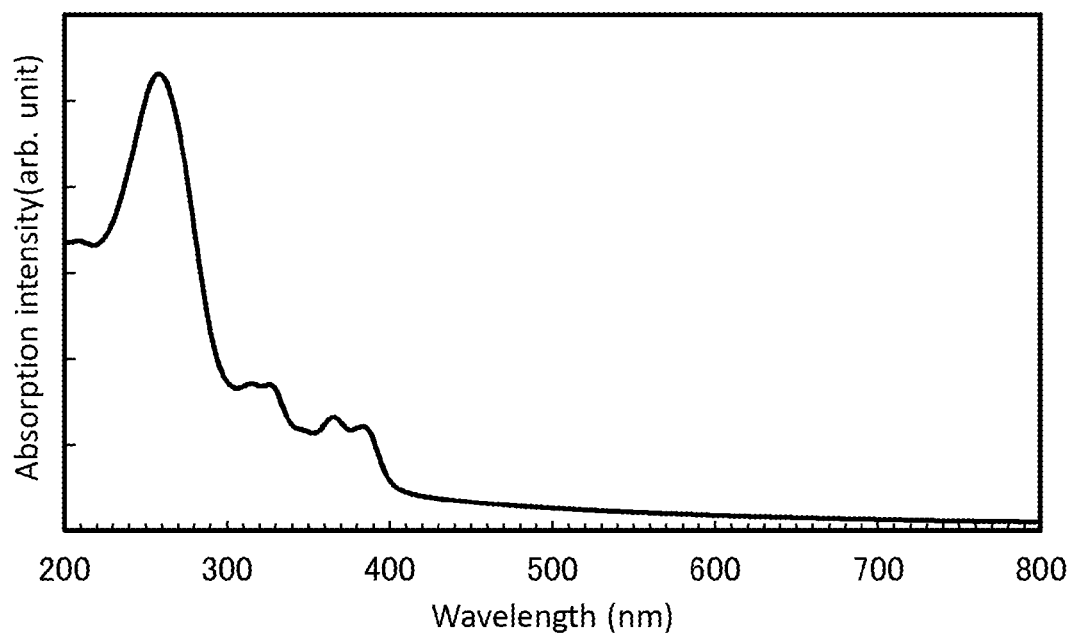
FIGS. 10A and 10B show an absorption spectrum and an emission spectrum of a thin film of 2mBnf(II)BPDBq.
Figure 10B:
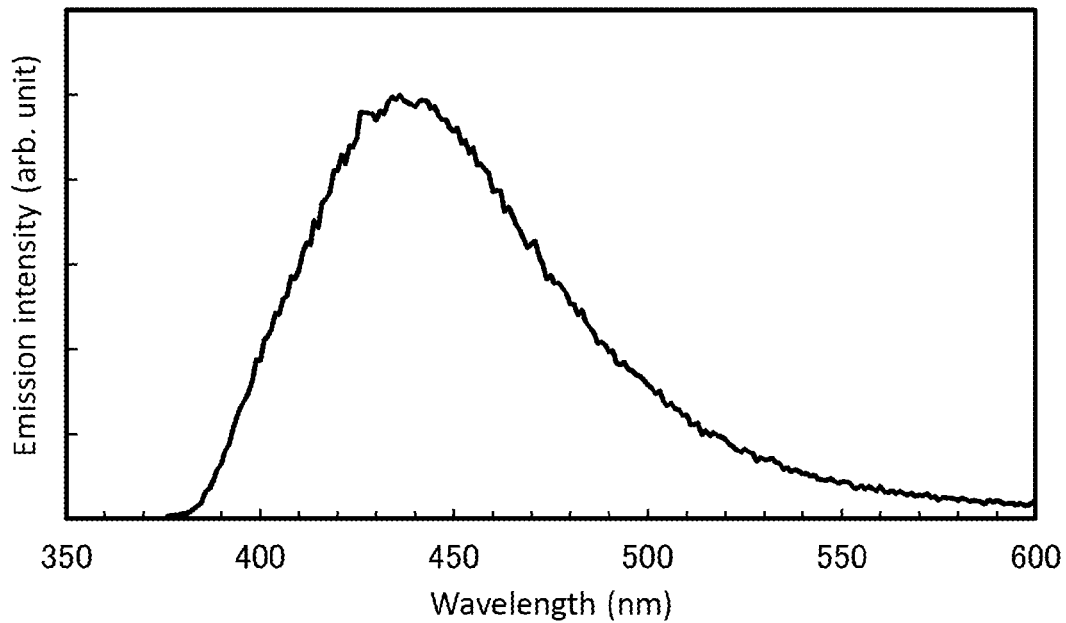

Furthermore, FIG. 9A shows an absorption spectrum of a toluene solution of 2mBnf(II)BPDBq, and FIG. 9B shows an emission spectrum thereof. FIG. 10A shows an absorption spectrum of a thin film of 2mBnf(II)BPDBq and FIG. 10B shows an emission spectrum thereof. The absorption spectrum was measured using an ultraviolet-visible spectrophotometer (V-550, produced by JASCO Corporation). For the measurement, the solution was put in a quartz cell and the thin film was formed on a quartz substrate by evaporation. The absorption spectrum of the solution was obtained by subtracting the absorption spectra of the quartz cell and toluene from those of the quartz cell and the solution, and the absorption spectrum of the thin film was obtained by subtracting the absorption spectrum of the quartz substrate from the absorption spectra of the thin film on the quartz substrate. In FIGS. 9A and 9B and FIGS. 10A and 10B, the horizontal axis indicates wavelength (nm) and the vertical axis indicates intensity (arbitrary unit). In the case of the toluene solution, absorption peaks are observed around 280 nm, 310 nm, 322 nm, 340 nm, and 358 nm, and emission wavelength peaks are observed at 385 nm and 404 nm (excitation wavelength: 358 nm). In the case of the thin film, absorption peaks are observed around 258 nm, 315 nm, 327 nm, 346 nm, 365 nm, and 384 nm, and an emission wavelength peak is observed at 435 nm (excitation wavelength: 369 nm).

Further, a HOMO level and a LUMO level of 2mBnf(II)BPDBq were obtained by cyclic voltammetry (CV) measurement. An electrochemical analyzer (ALS model 600A or 600C, produced by BAS Inc.) was used for the CV measurement.

As for a solution used for the CV measurement, dehydrated dimethylformamide (DMF, produced by Sigma-Aldrich Co. LLC., 99.8%, catalog No. 22705-6) was used as a solvent, and tetra-n-butylammonium perchlorate (n-Bu$_4$NClO$_4$, produced by Tokyo Chemical Industry Co., Ltd., catalog No. T0836), which was a supporting electrolyte, was dissolved in the solvent such that the concentration of tetra-n-butylammonium perchlorate was 100 mmol/L. Furthermore, the object to be measured was dissolved in the solution such that the concentration was 2 mmol/L. A platinum electrode (PTE platinum electrode, produced by BAS Inc.) was used as a working electrode, a platinum electrode (Pt counter electrode for VC-3 (5 cm), produced by BAS Inc.) was used as an auxiliary electrode, and an Ag/Ag' electrode (RE-7 reference electrode for nonaqueous solvent, produced by BAS Inc.) was used as a reference electrode. Note that the measurement was conducted at room temperature (20° C. to 25° C.). In addition, the scan rate at the CV measurement was set to 0.1 V/sec. Note that the potential energy of the reference electrode with respect to the vacuum level was assumed to be −4.94 [eV] in this example.

On the assumption that the intermediate potential (the half-wave potential) between the oxidation peak potential $E_{pa}$ and the reduction peak potential $E_{pe}$ which are obtained in the CV measurement corresponds to the HOMO level, the HOMO level of 2mBnf(II)BPDBq was calculated to be −6.03 eV, and the LUMO level of 2mBnf(II)BPDBq was calculated to be −2.95 eV. Accordingly, the band gap ($\Delta E$) of 2mBnf(II)BPDBq was found to be 3.08 eV.

Furthermore, 2mBnf(II)BPDBq was subjected to mass spectrometric (MS) analysis by liquid chromatography mass spectrometry (LC-MS).

In the analysis by LC-MS, liquid chromatography (LC) separation was carried out with UltiMate 3000 produced by Thermo Fisher Scientific K.K., and the MS analysis was carried out with Q Exactive produced by Thermo Fisher Scientific K.K. ACQUITY UPLC BEH C8 (2.1×100 mm, 1.7 μm) was used as a column for the LC separation, and the column temperature was 40° C. Acetonitrile was used for Mobile Phase A and a 0.1% aqueous solution of formic acid was used for Mobile Phase B. Analysis was performed by a gradient method for 10 minutes, in which the proportion of acetonitrile was 70% at the start of the analysis and increased linearly to reach 95% after 10 minutes from the start of the analysis. A sample was prepared in such a manner that 2mBnf(II)BPDBq was dissolved in chloroform at a given concentration and the mixture was diluted with acetonitrile. The injection amount was 5.0 μL.

In the MS analysis, ionization was carried out by an electrospray ionization (ESI) method, and measurement was carried out by targeted-MS². Conditions of an ion source were set as follows: the flow rates of a sheath gas, an Aux gas, and a Sweep gas were 50, 10, and 0, respectively, the spray voltage was 3.5 kV, the capillary temperature was 380° C., the S lens voltage was 55.0, and the HESI heater temperature was 350° C. The resolution was 35000, the AGC target was 3e6, the mass range was m/z=50.00 to 630.00, and the detection was performed in a positive mode.

Figure 11A:
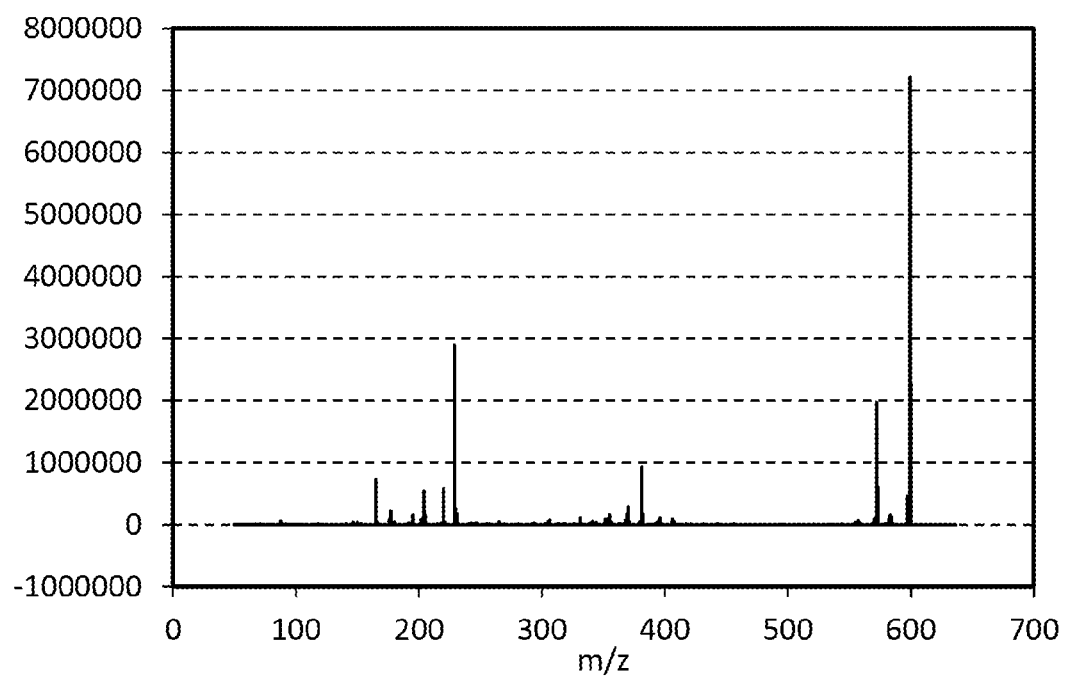
FIGS. 11A and 11B show results of LC-MS analysis of 2mBnf(II)BPDBq.
Figure 11B:
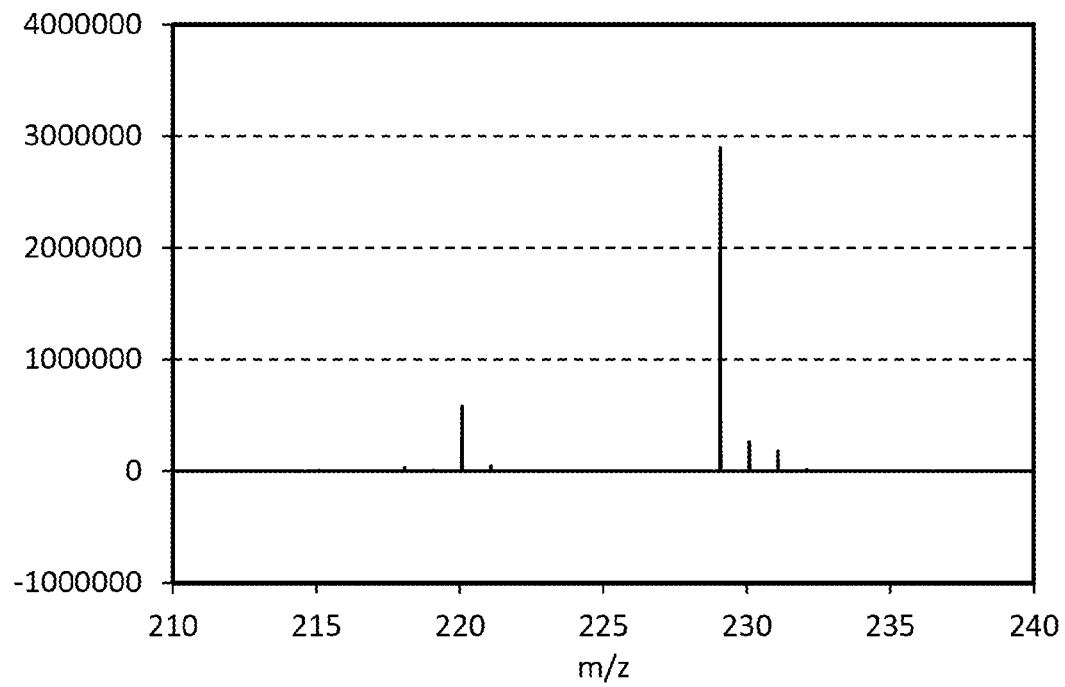

A component with m/z of 599.21±10 ppm that underwent the ionization under the above-described conditions was collided with an argon gas in a collision cell to dissociate into product ions, and MS/MS measurement was carried out. Ions which were generated under a normalized collision energy (NCE) for the collision with argon of 50 were detected with a Fourier transform mass spectrometer (FT MS). FIGS. 11A and 11B show the measurement results.

The results in FIGS. 11A and 11B demonstrate that product ions of 2mBnf(II)BPDBq are detected around m/z=381, m/z=229, and m/z=220. Note that the results in FIGS. 11A and 11B show characteristics derived from 2mBnf(II)BPDBq and thus can be regarded as important data for identifying 2mBnf(II)BPDBq contained in a mixture.

The product ion around m/z=381 is presumed to be a cation derived from 2-(3,1'-biphenyl-1-yl)dibenzo[f,h]quinoxaline in 2mBnf(II)BPDBq, and indicates a partial structure of the compound of one embodiment of the present invention. The product ion around m/z=229 is presumed to be a cation derived from dibenzo[f,h]quinoxaline in 2mBnf(II)BPDBq, and indicates a partial structure of the compound of one embodiment of the present invention. The product ion around m/z=220 is presumed to be a cation derived from an alcohol formed by cleavage of an ether linkage in benzo[b]naphtho[2,3-d]furan (Structural Formula (10) or Structural Formula (11)), and indicates a partial structure of the compound of one embodiment of the present invention.

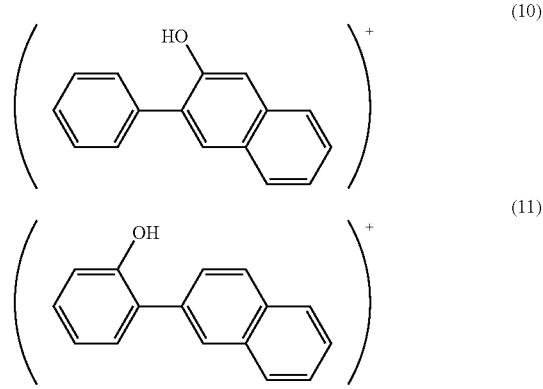

The product ion around m/z=572 is presumed to be a cation derived from 2mBnf(II)BPDBq in the state where one CH and one N are dissociated from dibenzo[f,h]quinoxaline in 2mBnf(II)BPDBq, and indicates a partial structure of the compound of one embodiment of the present invention. In particular, this is one of features of the compound of one embodiment of the present invention in which a substituent (in 2mBnf(II)BPDBq, a biphenyl skeleton bonded to a benzo[b]naphtho[2,3-d]furan skeleton) is bonded to the 2-position of dibenzo[f,h]quinoxaline.

Phosphorescence of 2mBnf(II)BPDBq was measured.

An evaporated film of 2mBnf(II)BPDBq was formed and was subjected to low-temperature photoluminescence (PL) measurement. The measurement was performed by using a PL microscope, LabRAM HR-PL, produced by HORIBA, Ltd., a He—Cd laser (325 nm) as excitation light, and a CCD detector at a measurement temperature of 10 K.

For the measurement, the evaporated film was formed over a quartz substrate to a thickness of 50 nm and another quartz substrate was attached to the deposition surface in a nitrogen atmosphere.

According to the measurement results, a peak wavelength on the shortest wavelength side of the phosphorescence spectrum was 536 nm. The $T_1$ level of 2mBnf(II)BPDBq was estimated from the wavelength to be 2.31 eV.

It was found that aggregation of the thin film of 2mBnf(II)BPDBq is not easily caused even under the air and the thin film suffers only a small change in shape and has high film quality.

The decomposition temperature Td of 2mBnf(II)BPDBq under atmospheric pressure was measured by thermogravimetry-differential thermal analysis (TG-DTA) to be 500° C. or more, which means that 2mBnf(II)BPDBq has high heat resistance. The measurement was conducted by using a high vacuum differential type differential thermal balance (TG/DTA 2410SA, produced by Bruker AXS K.K.).

Furthermore, thermophysical properties were measured using a differential scanning calorimeter (Pyris 1 DSC, produced by PerkinElmer Inc.). One cycle in the measurement was as follows: a sample was maintained at −10° C. for 1 minute, the temperature was raised from −10° C. to 350° C. at a rate of 50° C./min, the sample was maintained at 350° C. for 1 minute, and the temperature was lowered from 350° C. to −10° C. at a rate of 50° C./min. In this measurement, two cycles were performed and the thermophysical properties were measured from the data obtained in the second cycle. Thus, the glass transition temperature Tg of 2mBnf(II)BPDBq was found to be 119° C., the crystallization temperature Tc thereof was found to be 206° C., and the melting points Tm thereof were found to be 285° C. and 300° C. Accordingly, 2mBnf(II)BPDBq has a high glass transition temperature, a high melting point, a high decomposition temperature, and high heat resistance.

EXAMPLE 2

Figure 12:
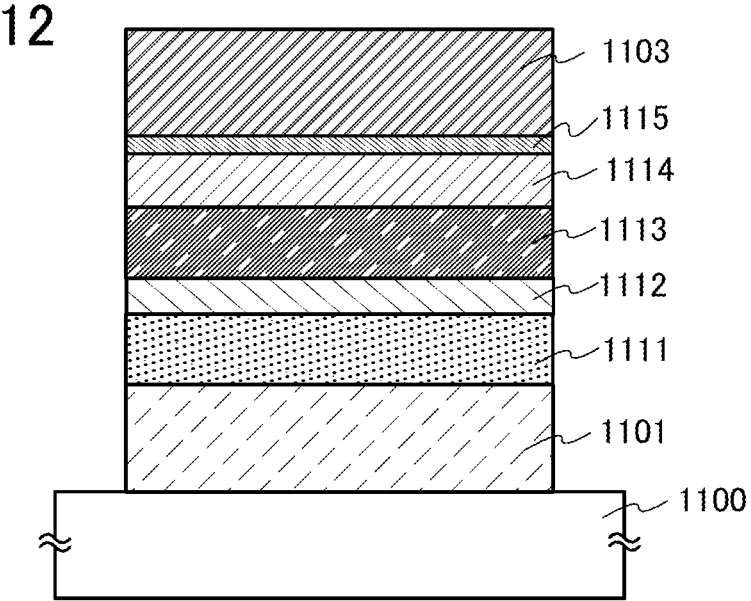
FIG. 12 illustrates light-emitting elements in Examples.

In this example, the light-emitting element of one embodiment of the present invention will be described with reference to FIG. 12. Chemical formulae of materials used in this example are shown below. Note that the chemical formulae of the materials which are shown above are omitted.

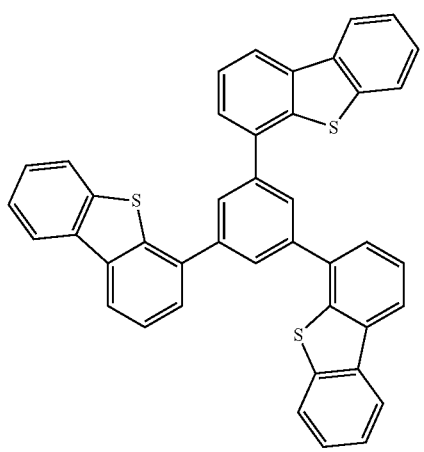

DBT3P-II

-continued

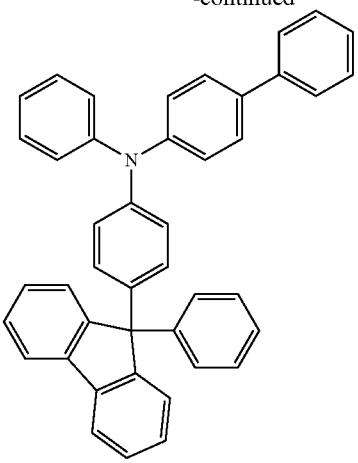

BPAFLP

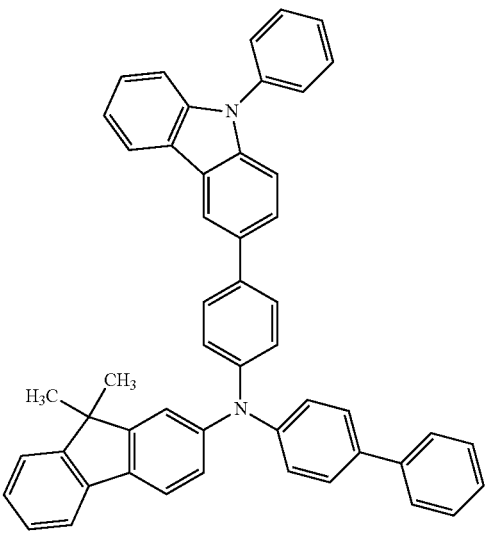

PCBBiF

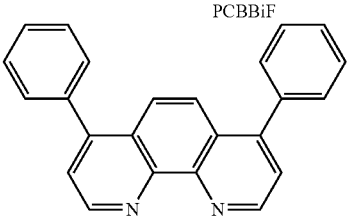

BPhen

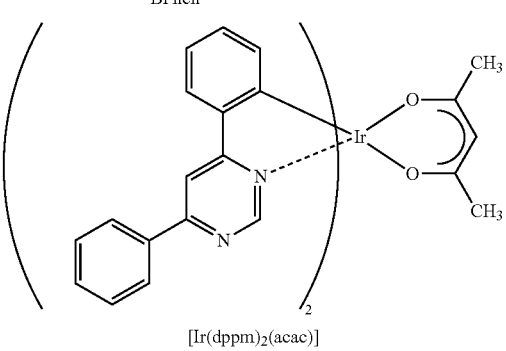

[Ir(dppm)$_2$(acac)]

A method for fabricating a light-emitting element 1 of this example will be described below.

(Light-Emitting Element 1)

A film of indium tin oxide containing silicon (ITSO) was formed over a glass substrate 1100 by a sputtering method, so that a first electrode 1101 which functions as an anode was formed. The thickness thereof was 110 nm and the electrode area was 2 mm×2 mm.

Next, as pretreatment for forming the light-emitting element over the glass substrate 1100, UV-ozone treatment was performed for 370 seconds after washing of a surface of the glass substrate 1100 with water and baking that was performed at 200° C. for 1 hour.

After that, the glass substrate 1100 was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the glass substrate 1100 was cooled down for approximately 30 minutes.

Then, the glass substrate 1100 over which the first electrode 1101 was formed was fixed to a substrate holder provided in the vacuum evaporation apparatus so that the surface on which the first electrode 1101 was formed faced downward. The pressure in the vacuum evaporation apparatus was reduced to approximately $10^{-4}$ Pa. After that, over the first electrode 1101, 4,4',4''-(1,3,5-benzenetriyl)tri(dibenzothiophene) (abbreviation: DBT3P-II) and molybdenum(VI) oxide were deposited by co-evaporation, so that a hole-injection layer 1111 was formed. The thickness of the hole-injection layer 1111 was set to 20 nm, and the weight ratio of DBT3P-II to molybdenum oxide was adjusted to 4:2 (=DBT3P-II: molybdenum oxide). Note that the co-evaporation method refers to an evaporation method in which evaporation is carried out from a plurality of evaporation sources at the same time in one treatment chamber.

Next, a film of 4-phenyl-4'-(9-phenylfluorene-9-yl)triphenylamine (abbreviation: BPAFLP) was formed to a thickness of 20 nm over the hole-injection layer 1111 to form a hole-transport layer 1112.

Furthermore, a light-emitting layer 1113 was formed over the hole-transport layer 1112 by co-evaporation of 2mBnf(II)BPDBq, N-(1,1'-biphenyl-4-yl)-N-[4-(9-phenyl-9H-carbazol-3-yl)phenyl]-9,9-dimethyl-9H-fluoren-2-amine (abbreviation: PCBBiF), and (acetylacetonato)bis(4,6-diphenylpyrimidinato)iridium(III) (abbreviation: [Ir(dppm)$_2$(acac)]). Here, a 20-nm-thick layer which was formed with the weight ratio of 2mBnf(II)BPDBq to PCBBiF to [Ir(dppm)$_2$(acac)] adjusted to 0.7:0.3:0.05 (=2mBnf(II)BPDBq:PCBBiF:[Ir(dppm)$_2$(acac)]) and a 20-nm-thick layer which was formed with the weight ratio adjusted to 0.8:0.2:0.05 (=2mBnf(II)BPDBq:PCBBiF:[Ir(dppm)$_2$(acac)]) were stacked.

Next, a film of 2mBnf(II)BPDBq was formed to a thickness of 20 nm over the light-emitting layer 1113 and then a film of bathophenanthroline (abbreviation: BPhen) was formed to a thickness of 10 nm, so that an electron-transport layer 1114 was formed.

After that, over the electron-transport layer 1114, a film of lithium fluoride (LiF) was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 1 of this example was fabricated.

Note that in all the above evaporation steps, evaporation was performed by a resistance-heating method.

Table 1 shows the element structure of the light-emitting element fabricated as described above in this example.

TABLE 1

| | First electrode | Hole-injection layer | Hole-transport layer | Light-emitting layer | Electron-transport layer | Electron-injection layer | Second electrode |
|---|---|---|---|---|---|---|---|
| Light-emitting element 1 | ITSO 110 nm | DBT3P-II: MoO$_x$ (=4:2) 20 nm | BPAFLP 20 nm | 2mBnf(II)BPDBq:PCBBiF: [Ir(dppm)$_2$(acac)] (=0.7:0.3:0.05) (=0.8:0.2:0.05) 20 nm 20 nm | 2mBnf(II)BPDBq 20 nm | BPhen 10 nm | LiF 1 nm | Al 200 nm |

The light-emitting element of this example was sealed in a glove box under a nitrogen atmosphere so as not to be exposed to the air. Then, the operation characteristics of the light-emitting element were measured. Note that the measurement was carried out at room temperature (in an atmosphere kept at 25° C.).

Figure 13:
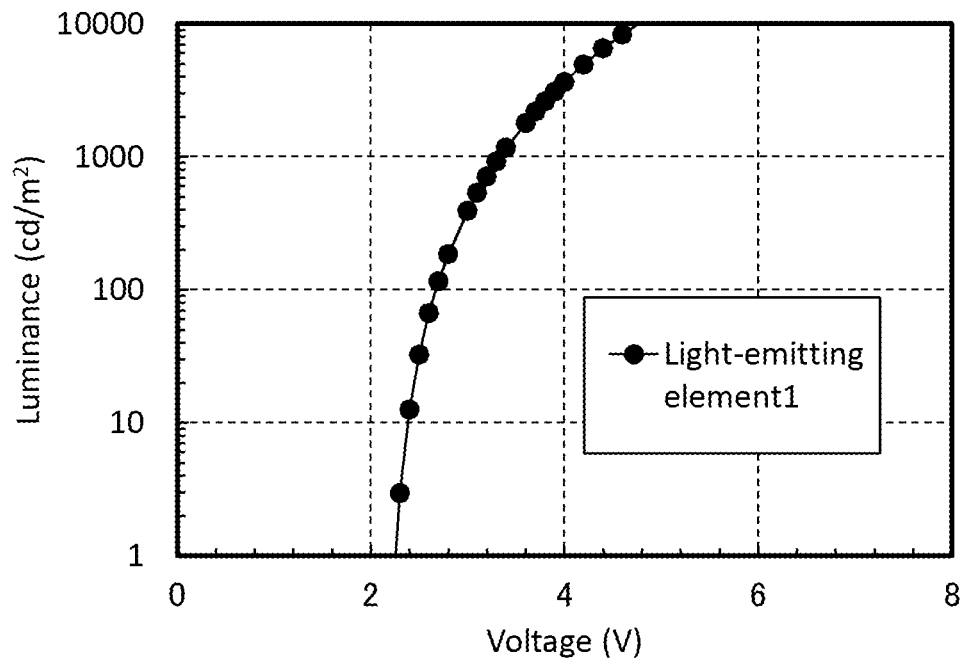
FIG. 13 is a graph showing voltage-luminance characteristics of a light-emitting element in Example 2.
Figure 14:
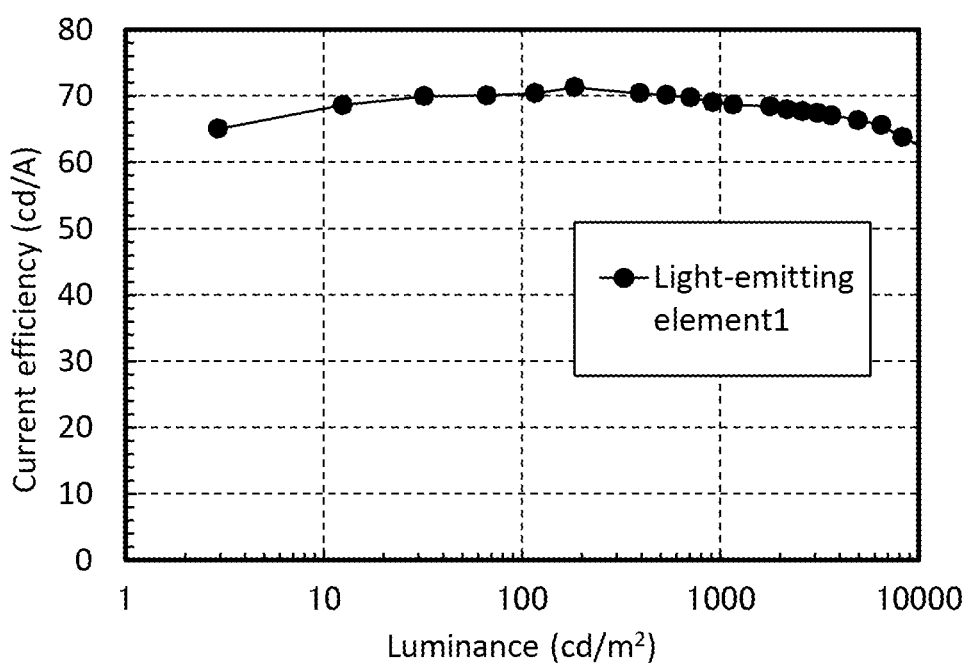
FIG. 14 is a graph showing luminance-current efficiency characteristics of a light-emitting element in Example 2.
Figure 15:
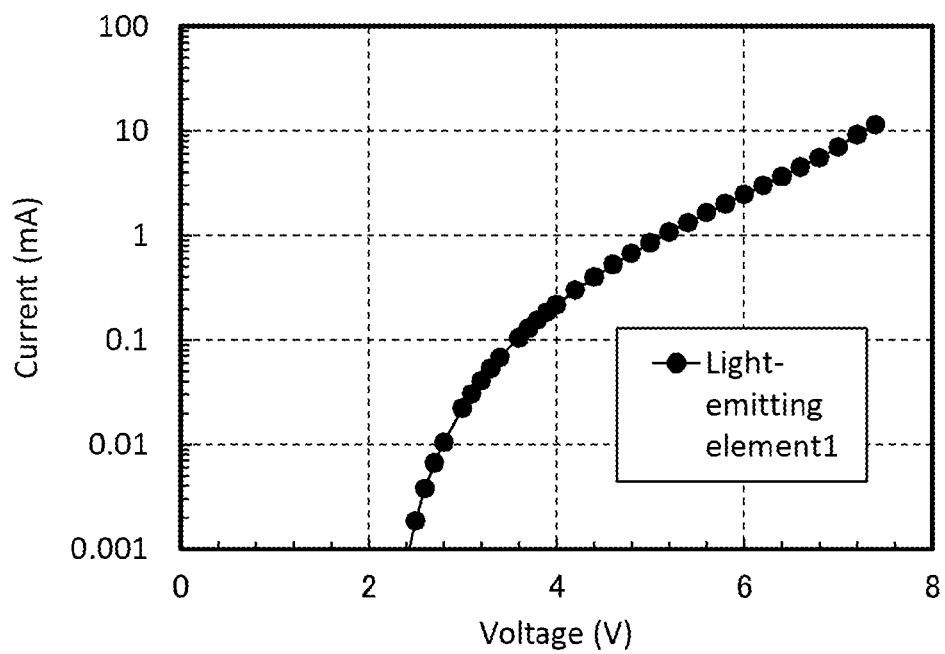
FIG. 15 is a graph showing voltage-current characteristics of a light-emitting element in Example 2.
Figure 16:
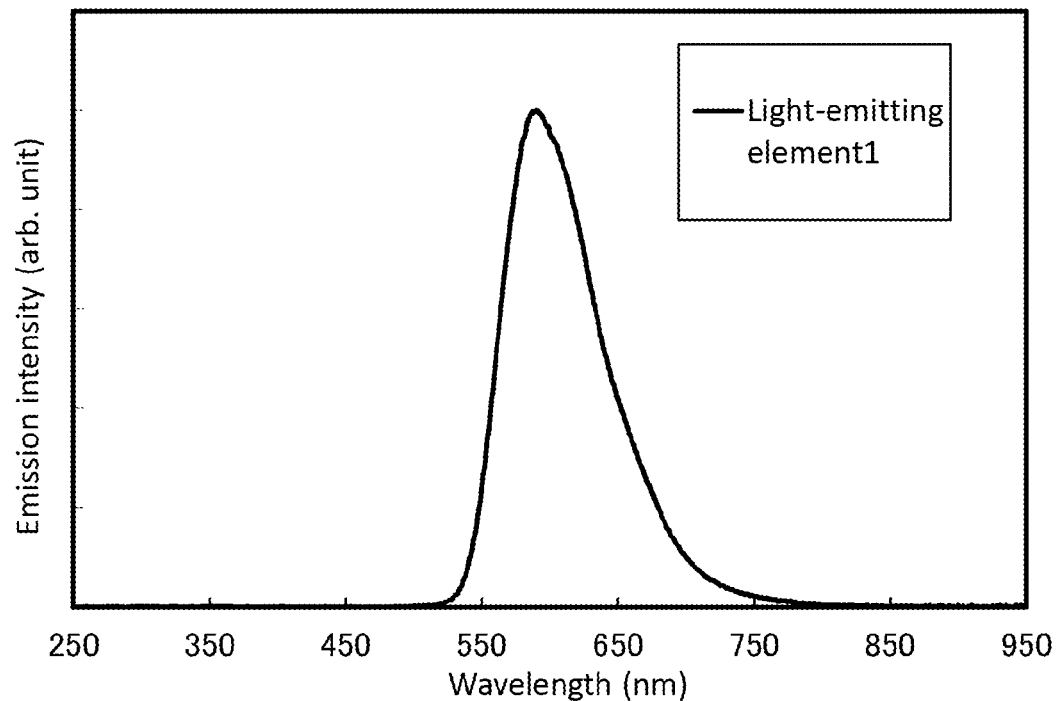
FIG. 16 is a graph showing an emission spectrum of a light-emitting element in Example 2.

FIG. 13 shows voltage-luminance characteristics of the light-emitting element 1. In FIG. 13, the horizontal axis indicates voltage (V), and the vertical axis indicates luminance (cd/m$^2$). FIG. 14 shows luminance-current efficiency characteristics. In FIG. 14, the horizontal axis indicates luminance (cd/m$^2$) and the vertical axis indicates current efficiency (cd/A). FIG. 15 shows voltage-current characteristics. In FIG. 15, the horizontal axis indicates voltage (V) and the vertical axis indicates current (mA). FIG. 16 shows an emission spectrum of the light-emitting element 1. In FIG. 16, the horizontal axis indicates a wavelength (nm) and the vertical axis indicates emission intensity (arbitrary unit). Table 2 shows the voltage (V), current density (mA/cm$^2$), CIE chromaticity coordinates (x, y), current efficiency (cd/A), power efficiency (lm/W), and external quantum efficiency (%) of the light-emitting element 1 at a luminance of 900 cd/m$^2$.

TABLE 2

| | Voltage (V) | Current density (mA/cm$^2$) | Chromaticity x | Chromaticity y | Luminance (cd/m$^2$) | Current efficiency (cd/A) | Power efficiency (lm/W) | External quantum efficiency (%) |
|---|---|---|---|---|---|---|---|---|
| Light-emitting element 1 | 3.3 | 1.3 | 0.57 | 0.43 | 900 | 69 | 66 | 29 |

The CIE chromaticity coordinates (x, y) at a luminance of 900 cd/m² of the light-emitting element 1 were (0.57, 0.43) and the light-emitting element 1 exhibited orange light emission. These results show that orange light emission originating from [Ir(dppm)₂(acac)] was provided from the light-emitting element 1.

The measurement results of the operation characteristics show that the light-emitting element 1 has high emission efficiency and a low drive voltage.

Figure 17:
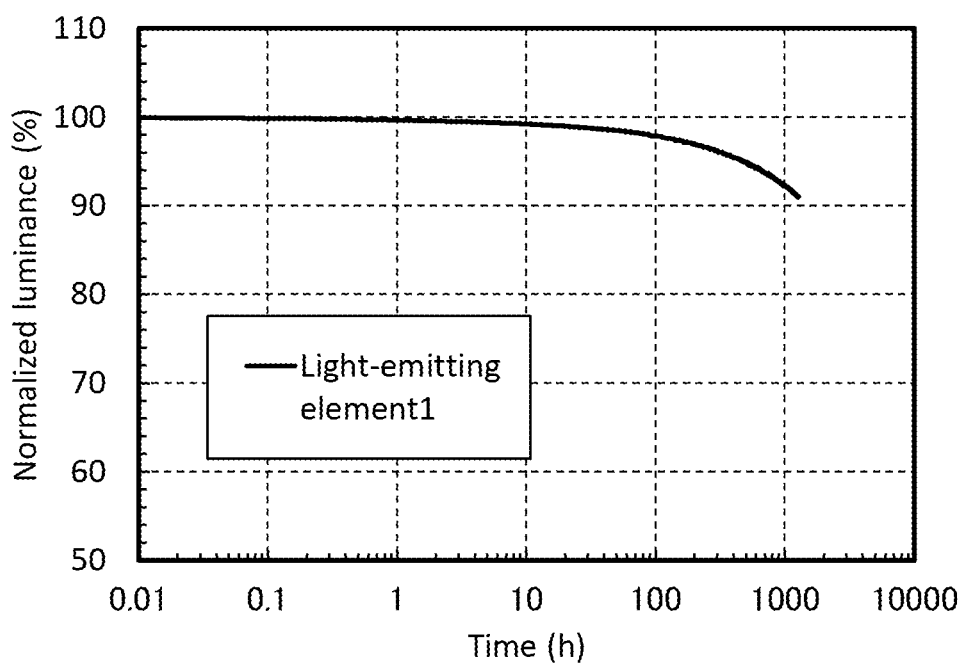
FIG. 17 shows results of a reliability test of a light-emitting element in Example 2.

A reliability test of the light-emitting element 1 was conducted. FIG. 17 shows results of the reliability test. In FIG. 17, the vertical axis indicates normalized luminance (%) with an initial luminance of 100% and the horizontal axis indicates driving time (h) of the element. In the reliability test, which was conducted at room temperature, the light-emitting element 1 was driven under the conditions different from that in the method for fabricating the light-emitting element 1 is described.

The light-emitting layer 1113 of the light-emitting element 2 was formed by co-evaporation of 2mBnf(II)BPDBq, PCBBiF, and (acetylacetonato)bis(6-tert-butyl-4-phenylpyrimidinato)iridium(III) (abbreviation: [Ir(tBuppm)₂(acac)]). Here, a 20-nm-thick layer which was formed with the weight ratio of 2mBnf(II)BPDBq to PCBBiF to [Ir(tBuppm)₂(acac)] adjusted to 0.7:0.3:0.05 (=2mBnf(II)BPDBq:PCBBiF:[Ir(tBuppm)₂(acac)]) and a 20-nm-thick layer which was formed with the weight ratio adjusted to 0.8:0.2:0.05 (=2mBnf(II)BPDBq:PCBBiF:[Ir(tBuppm)₂(acac)]) were stacked.

Table 3 shows the element structure of the light-emitting element fabricated as described above in this example.

TABLE 3

| | First electrode | Hole-injection layer | Hole-transport layer | Light-emitting layer | Electron-transport layer | | Electron-injection layer | Second electrode |
|---|---|---|---|---|---|---|---|---|
| Light-emitting element 2 | ITSO 110 nm | DBT3P-II: MoO$_x$ (=4:2) 20 nm | BPAFLP 20 nm | 2mBnf(II)BPDBq:PCBBiF: [Ir(tBuppm)₂(acac)] (=0.7:0.3:0.05) (=0.8:0.2:0.05) 20 nm     20 nm | 2mBnf(II)BPDBq 20 nm | BPhen 10 nm | LiF 1 nm | Al 200 nm | where the initial luminance was set to 5000 cd/m² and the current density was constant. FIG. 17 shows that the light-emitting element 1 kept 91% of the initial luminance after 1300 hours. The results of the reliability test show that the light-emitting element 1 has a long lifetime.

EXAMPLE 3

In this example, the light-emitting element of one embodiment of the present invention was fabricated and a preservation test was conducted. The results of the preservation test are described. A chemical formula of a material used in this example is shown below. Note that the chemical formulae of the materials which are shown above are omitted.

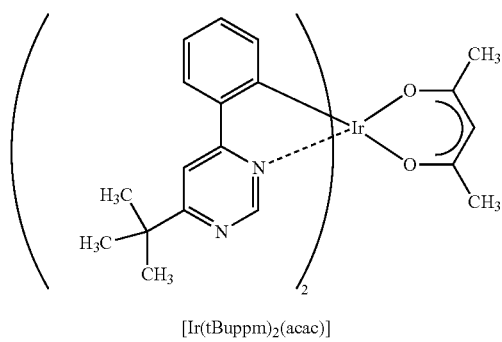

[Ir(tBuppm)₂(acac)]

A method for fabricating a light-emitting element 2 of this example will be described below. FIG. 12 can be referred to for the structure of the light-emitting element in this example.

(Light-Emitting Element 2)

In the light-emitting element 2, components other than the light-emitting layer 1113 were formed in the same manners as those of the light-emitting element 1. Here, only the step In this example, the fabricated light-emitting element was preserved in a thermostatic oven maintained at 100° C., and after a predetermined time elapsed, the operation characteristics were measured. Note that the operation characteristics were measured at room temperature (in an atmosphere kept at 25° C.) after the light-emitting element was taken out of the thermostatic oven.

Figure 18:
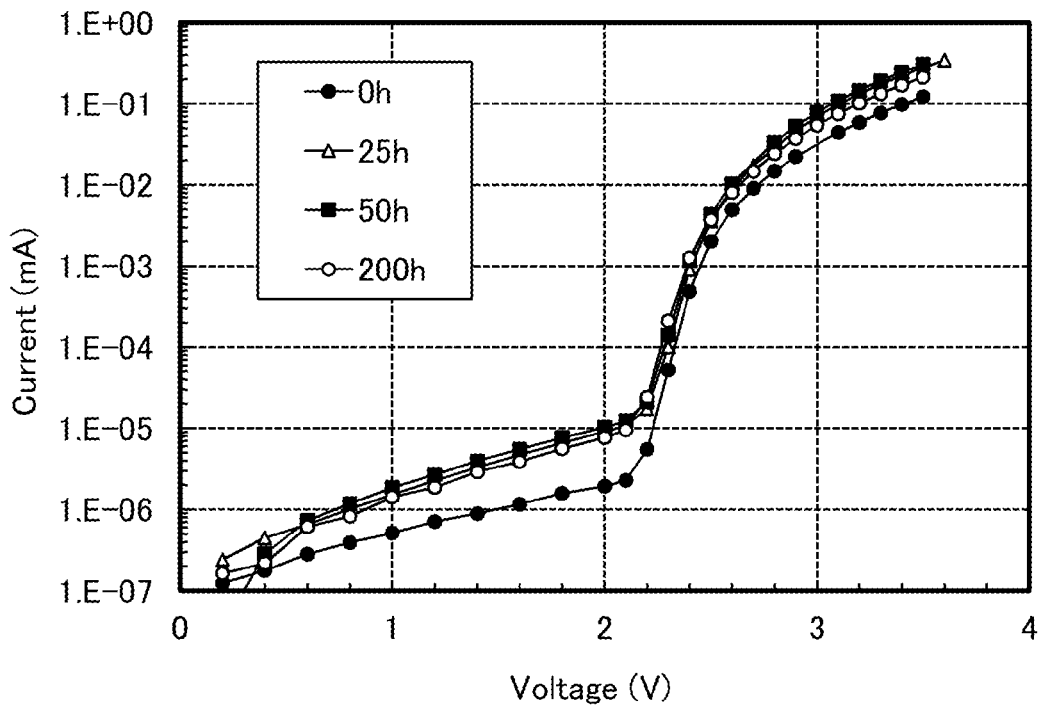
FIG. 18 is a graph showing voltage-current characteristics of a light-emitting element in Example 3.
Figure 19:
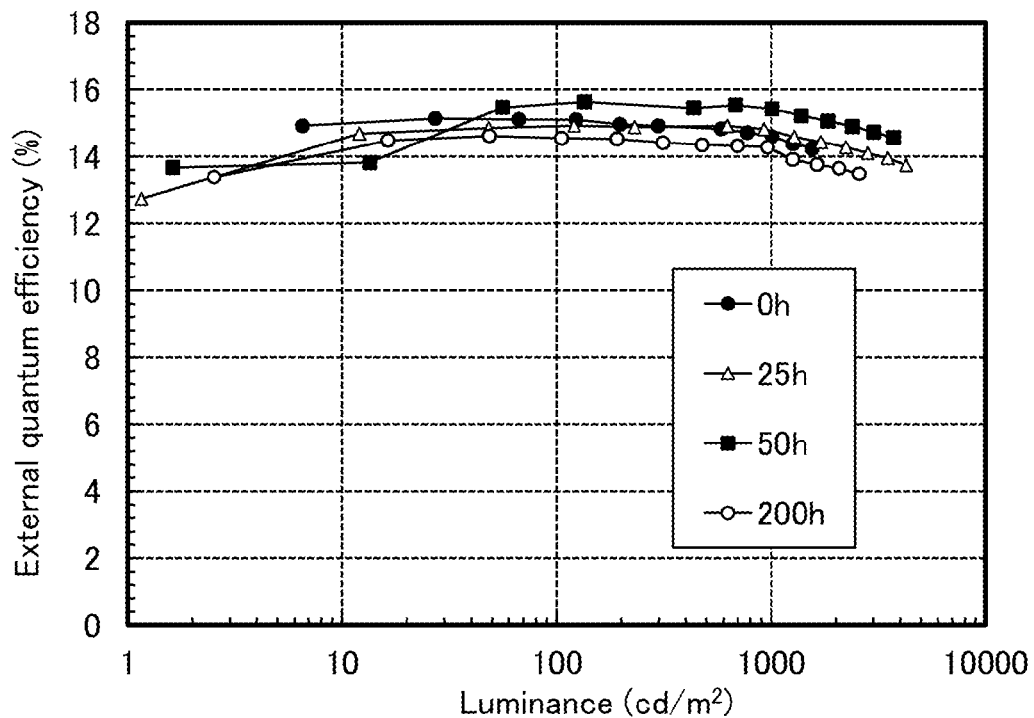
FIG. 19 is a graph showing luminance-external quantum efficiency characteristics of a light-emitting element in Example 3.

FIG. 18 shows the voltage-current characteristics of the light-emitting element after preservation at 100° C. for 200 hours, and FIG. 19 shows the luminance-external quantum efficiency characteristics thereof. Note that FIGS. 18 and 19 also show the characteristics of the light-emitting element before the preservation test, those after 25-hour preservation, and those after 50-hour preservation.

As can be seen in FIGS. 18 and 19, the light-emitting element in this example suffered only a small change in the voltage-current characteristics and luminance-external quantum efficiency characteristics even after preservation at 100° C. for 200 hours, and the element characteristics hardly deteriorated. Accordingly, with the use of the compound of one embodiment of the present invention, a highly heat-resistant and highly reliable light-emitting element can be obtained.

This application is based on Japanese Patent Application serial no. 2014-095159 filed with the Japan Patent Office on May 2, 2014, the entire contents of which are hereby incorporated by reference.

What is claimed is:

1. A compound represented by Formula (G0):

A¹-Ar-A²     (G0)

wherein:
A¹ represents a dibenzo[f,h]quinoxalinyl group;
A² represents a benzo[b]naphtho[2,3-d]furanyl group;
Ar represents an arylene group having 6 to 25 carbon atoms; and
the dibenzo[f,h]quinoxalinyl group, the benzo[b]naphtho[2,3-d]furanyl group, and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

2. The compound according to claim 1,
wherein:
the compound is represented by Formula (G1);

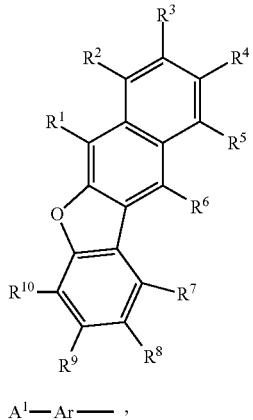

(G1)

A¹—Ar—— ,  (G1-1)

one of $R^7$ to $R^{10}$ represents a substituent represented by Formula (G1-1); and
$R^1$ to $R^6$ and the others of $R^7$ to $R^{10}$ separately represent any one of hydrogen, an alkyl group having 1 to 6 carbon atoms, a cycloalkyl group having 3 to 6 carbon atoms, and an aryl group having 6 to 13 carbon atoms.

3. The compound according to claim 2,
wherein:
the compound is represented by Formula (G2), (G2)

4. A light-emitting element comprising, between a pair of electrodes, a layer containing the compound according to claim 1.

5. A light-emitting device comprising:
the light-emitting element according to claim 4; and
a transistor or a substrate.

6. An electronic device comprising:
the light-emitting device according to claim 5; and
a microphone, a speaker, or an external connection terminal.

7. A lighting device comprising:
the light-emitting device according to claim 5; and
a support, a housing, or a cover.

8. A compound represented by Formula (G3):

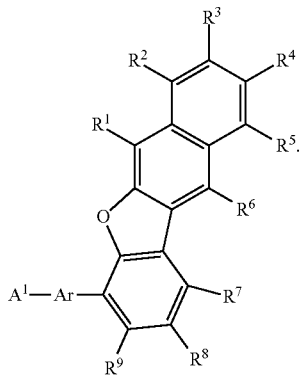

(G3)

wherein:
$R^1$ to $R^9$ and $R^{11}$ to $R^{19}$ separately represent any one of hydrogen, an alkyl group having 1 to 6 carbon atoms, a cycloalkyl group having 3 to 6 carbon atoms, and an aryl group having 6 to 13 carbon atoms;
Ar represents an arylene group having 6 to 25 carbon atoms; and
the aryl group and the arylene group are separately unsubstituted or substituted by any one of an alkyl group having 1 to 6 carbon atoms, a cycloalkyl group having 3 to 6 carbon atoms, and an aryl group having 6 to 13 carbon atoms.

9. The compound according to claim 8,
wherein the compound is represented by Formula (101), (101)

10. A light-emitting element comprising, between a pair of electrodes, a layer containing the compound according to claim 8.

11. A light-emitting device comprising:
the light-emitting element according to claim 10; and
a transistor or a substrate.

12. An electronic device comprising:
the light-emitting device according to claim 11; and
a microphone, a speaker, or an external connection terminal.

13. A lighting device comprising:
the light-emitting device according to claim 11; and
a support, a housing, or a cover.

14. A light-emitting element comprising, between a pair of electrodes, a layer containing a compound,
wherein the compound comprises a dibenzo[f,h]quinoxaline skeleton and a benzo[b]naphtho[2,3-d]furan skeleton.

15. The light-emitting element according to claim 14,
wherein the dibenzo[f,h]quinoxaline skeleton and the benzo[b]naphtho[2,3-d]furan skeleton are bonded through an arylene skeleton.

16. A light-emitting device comprising:
the light-emitting element according to claim 15; and
a transistor or a substrate.

17. An electronic device comprising:
the light-emitting device according to claim 16; and
a microphone, a speaker, or an external connection terminal.

18. A lighting device comprising:
the light-emitting device according to claim 16; and
a support, a housing, or a cover.

\* \* \* \* \*